United States Patent
Wu

(10) Patent No.: US 11,649,233 B2
(45) Date of Patent: May 16, 2023

(54) HALO-ALLYLAMINE SSAO/VAP-1 INHIBITOR AND USE THEREOF

(71) Applicant: Nanjing Transthera Biosciences Co., Ltd., Nanjing (CN)

(72) Inventor: Frank Wu, Nanjing (CN)

(73) Assignee: NANJING TRANSTHERA BIOSCIENCES CO., LTD., Nanjing (CN)

( * ) Notice: Subject to any disclaimer, the term of this patent is extended or adjusted under 35 U.S.C. 154(b) by 156 days.

(21) Appl. No.: 15/733,125

(22) PCT Filed: Nov. 21, 2018

(86) PCT No.: PCT/CN2018/116606
§ 371 (c)(1),
(2) Date: Nov. 16, 2020

(87) PCT Pub. No.: WO2019/101086
PCT Pub. Date: May 31, 2019

(65) Prior Publication Data
US 2021/0070750 A1  Mar. 11, 2021

(30) Foreign Application Priority Data

Nov. 21, 2017 (CN) .......................... 201711163324.7
Jan. 29, 2018 (CN) .......................... 201810081619.8
Jul. 30, 2018 (CN) .......................... 201810854213.9

(51) Int. Cl.
| C07D 471/04 | (2006.01) |
| C07D 209/08 | (2006.01) |
| C07D 209/46 | (2006.01) |
| C07D 213/82 | (2006.01) |
| C07D 217/24 | (2006.01) |

(52) U.S. Cl.
CPC ......... *C07D 471/04* (2013.01); *C07D 209/08* (2013.01); *C07D 209/46* (2013.01); *C07D 213/82* (2013.01); *C07D 217/24* (2013.01)

(58) Field of Classification Search
None
See application file for complete search history.

(56) References Cited

U.S. PATENT DOCUMENTS

| 9,302,986 | B2 | 4/2016 | Deodhar et al. |
| 2007/0293548 | A1 | 12/2007 | Wang et al. |
| 2018/0296560 | A1 | 10/2018 | Fan et al. |
| 2018/0297987 | A1 | 10/2018 | Coates et al. |

FOREIGN PATENT DOCUMENTS

| CN | 104520268 A | 4/2015 |
| WO | WO-2007120528 A2 | 10/2007 |
| WO | 2013163675 A1 | 11/2013 |
| WO | WO-2018028517 A1 | 2/2018 |
| WO | WO-2018151985 A1 | 8/2018 |
| WO | WO-2018196677 A1 | 11/2018 |
| WO | WO-2019101086 A1 | 5/2019 |

OTHER PUBLICATIONS

Extended European Search Report issued for European Patent Application No. 18881966.8 dated Oct. 23, 2020, 8 pages.
"International Application No. PCT/CN2018/116606, International Preliminary Report on Patentability dated Apr. 30, 2020", (dated Apr. 30, 2020), 57 pgs.
"International Application No. PCT/CN2018/116606, International Search Report and Written Opinion dated Jan. 29, 2019", (dated Jan. 29, 2019), 16 pgs.

*Primary Examiner* — Samantha L Shterengarts
(74) *Attorney, Agent, or Firm* — Rothwell, Figg, Ernst & Manbeck, P.C.

(57) ABSTRACT

The present invention belongs to the pharmaceutical technical field, and specifically relates to a haloallylamine compound represented by formula I, a pharmaceutically acceptable salt, an ester or a stereoisomer thereof, $R_1$, $R_2$, $R_3$, $R_4$, $R_5$, $R_6$, $L_1$, $C_{y1}$, $R_7$ are defined as in the specification; the present invention also relates to pharmaceutical preparations and pharmaceutical compositions containing these compounds, and their use in preventing and/or treating the SSAO/VAP-1 protein-related or SSAO/VAP-1 protein-mediated disease.

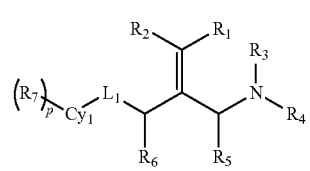

I

11 Claims, No Drawings

HALO-ALLYLAMINE SSAO/VAP-1 INHIBITOR AND USE THEREOF

PRIORITY CLAIM TO RELATED APPLICATIONS

This application is a U.S. national stage filing under 35 U.S.C. § 371 from International Application No. PCT/CN2018/116606, filed on 21 Nov. 2018, and published as WO2019/101086 on 31 May 2019, which claims the benefit under 35 U.S.C. 119 to Chinese Application No. 201711163324.7, filed on 21 Nov. 2017, and claims the benefit under 35 U.S.C. 119 to Chinese Application No. 201810081619.8, filed on 29 Jan. 2018, and claims the benefit under 35 U.S.C. 119 to Chinese Application No. 201810854213.9, filed on 30 Jul. 2018, the benefit of priority of each of which is claimed herein, and which applications and publication are hereby incorporated herein by reference in their entirety.

TECHNICAL FIELD

The present invention belongs to the pharmaceutical technical field, and relates to a haloallylamine compound, a pharmaceutically acceptable salt, an ester or a stereoisomer thereof, and pharmaceutical preparations and pharmaceutical compositions containing these compounds, and use thereof in preventing and/or treating the SSAO/VAP-1 protein-related or SSAO/VAP-1 protein-mediated disease.

BACKGROUND

Semicarbazide-sensitive amine oxidases (SSAO) are a class of amine oxidases that are particularly sensitive to semicarbazides, and are widely distributed in the body, both on cell membranes and in plasma. In endothelial cells, SSAO exists in the form of Vascular Adhesion Protein-1 (VAP-1). At present, its physiological function in the body is considered to be mainly involved in the metabolism of amine, i.e., catalyzing the oxidative deamination of the short-chain primary amine such as methylamine and aminoacetone to generate the corresponding aldehyde, hydrogen peroxide and ammonia. The SSAO structure contains one divalent copper ion with a quinonyl group as a coenzyme. SSAO has no specific substrate, and mainly acts on aliphatic and aromatic primary amines.

At present, no SSAO/AP-1 inhibitor is on the market, and the SSAO/VAP-1 inhibitor of the present invention can be used for effectively relieving the symptoms and pathological changes in the disorders relevant to the SSAO/VAP-1 overexpression and the like under various disease states, and therefore has a huge application prospect.

SUMMARY OF THE INVENTION

The technical problem to be solved by the present invention is to provide a novel SSAO/VAP-1 inhibitor, which has strong inhibitory activity on SSAO/VAP-1 protein and can be used for preventing and/or treating the SSAO/VAP-1 protein-related or SSAO/VAP-1 protein-mediated disease. In addition, the haloallylamine compound of the present invention shows excellent specific selectivity for SSAO/VAP-1 protein, thereby avoiding other side effects while preventing and/or treating the SSAO/VAP-1 protein-related or SSAO/VAP-1 protein-mediated disease.

Specifically, the present invention provides the following technical solutions.

In an embodiment of the present invention, there is provided a compound represented by formula I, a pharmaceutically acceptable salt, an ester or a stereoisomer thereof (hereinafter, sometimes also called "the compound of the present invention"):

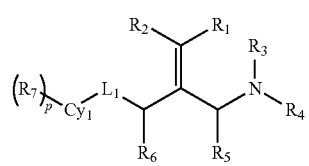

I wherein, $R_1$ and $R_2$ are each independently selected from hydrogen, and halogen atom, and $R_1$ and $R_2$ are not hydrogen at the same time;

$R_3$ and $R_4$ are each independently selected from hydrogen or $C_{1-6}$alkyl, or together with the N atom to which they are attached form a nitrogen-containing 5-10-membered heterocyclic ring optionally substituted with a substituent;

$R_5$ and $R_6$ are each independently selected from hydrogen or $C_{1-6}$ alkyl;

$L_1$ is a bond, —CR'R"—, —N—, —O—, —S—, —SO$_2$—, —S(O)—, —SONR'—, —SO$_2$NR'—, or —NR'CONR'—, R' and R" are each independently selected from hydrogen or $C_{1-6}$ alkyl;

$C_{y1}$ is 3-12 membered cycloalkyl optionally substituted with a substituent, 3-12 membered cycloalkenyl optionally substituted with a substituent, 3-12 membered heterocyclyl optionally substituted with a substituent, 5-14 membered heteroaryl optionally substituted with a substituent, said substituents are each independently selected from hydroxy, amino, carboxyl, cyano, nitro, halogen atom, $C_{1-6}$alkyl, $C_{1-6}$alkoxyl, $C_{1-6}$alkoxylC$_{1-6}$alkoxyl, $C_{1-6}$alkylamino, ($C_{1-6}$alkyl)$_2$amino, $C_{1-6}$alkylcarbonylamino, $C_{1-6}$alkylsulfonylamino, haloC$_{1-6}$alkyl, haloC$_{1-6}$alkoxyl, $C_{1-6}$alkylsulfonyl, $C_{1-6}$alkylthio, 3-8-membered cycloalkyl, aryl, 4-6-membered heterocyclyl, 5-10-membered heteroaryl or oxo, and when two substituents are present at the same site, two substituents may form a 3-6 membered ring with the atom to which they are attached; when two substituents are present at the different sites, two substituents may form a 3-6 membered ring with the atoms to which they are attached; the atom(s) on $C_{y1}$ may also form a 4-7-membered ring together with the atoms in $R_6$ and $L_1$;

p is an integral number of 1-4, $R_7$ is each independently selected from hydrogen, hydroxy, amino, carboxyl, cyano, nitro, halogen atom, $C_{1-6}$alkyl, haloC$_{1-6}$alkyl,

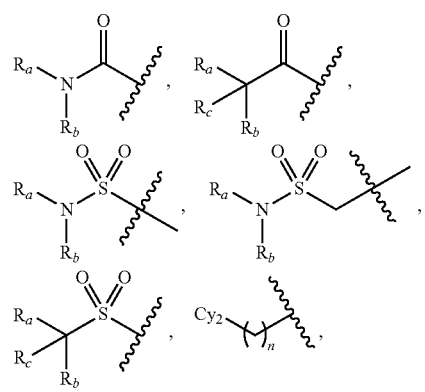

-continued

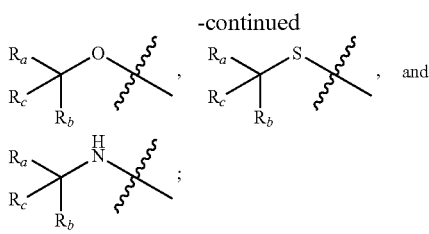

$R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 3-12-membered heterocyclyl optionally substituted with a substituent, 5-10-membered heteroaryl optionally substituted with a substituent, or, $R_a$ and $R_b$ may form a 3-8 membered ring with the atom to which they are attached; $C_{y2}$ is aryl optionally substituted with a substituent, 3-12-membered heterocyclyl optionally substituted with a substituent, 5-10-membered heteroaryl optionally substituted with a substituent, n is an integral number of 0-4; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl, 5-10-membered heteroaryl or oxo.

In another embodiment of the present invention, there is provided the compound represented by the above formula I, a pharmaceutically acceptable salt, an ester or a stereoisomer thereof:
wherein,
$C_{y1}$ is a group represented by the following formula a or b:

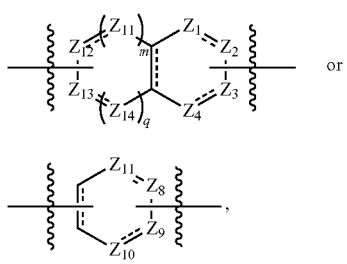

a b wherein, $Z_1$, $Z_2$, $Z_3$, $Z_4$, $Z_8$, $Z_9$, $Z_{10}$, $Z_{12}$, $Z_{13}$ and $Z_{14}$ are each independently selected from $CR_eR_f$, $NR_g$, $CR_e$, N, O or S, and $Z_8$, $Z_9$, $Z_{10}$, and $Z_{11}$ are not CH at the same time,
--- represents a single bond or a double bond, provided that the valences of the bonded atoms are not violated, $R_e$, $R_f$, $R_g$ are each independently selected from hydrogen, hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl, 5-10-membered heteroaryl, or, $R_e$ and $R_f$ may form a 3-6 membered ring with the atom to which they are attached, or $R_e$ and $R_f$ together form an oxo group;
m is 0, 1 or 2, q is 0, 1 or 2.

In another embodiment of the present invention, in formula a, when $Z_1$, $Z_2$, $Z_3$, $Z_4$ are all $CR_eR_f$ or $CR_e$, and the ring formed by $Z_1$, $Z_2$, $Z_3$ and $Z_4$ is bonded to the $R_7$ group, at least one of $Z_{11}$, $Z_{12}$, $Z_{13}$ and $Z_{14}$ is N or $NR_g$, and the ring formed by $Z_1$, $Z_2$, $Z_3$ and $Z_4$ is bonded to the $L_1$ group.

In another embodiment of the present invention, in formula a, when at least one of $Z_1$, $Z_2$, $Z_3$ and $Z_4$ is NR or N and they are not $NR_g$ or N at the same time, the ring formed by $Z_1$, $Z_2$, $Z_3$ and $Z_4$ is bonded to the $L_1$ group.

In another embodiment of the present invention, in formula a, when $Z_1$, $Z_2$, $Z_3$ and $Z_4$ are all $CR_eR_f$ or $CR_e$, and the ring formed by $Z_1$, $Z_2$, $Z_3$ and $Z_4$ is bonded to the $L_1$ group, and m+q=1, at least one of $Z_{11}$, $Z_{12}$, $Z_{13}$ and $Z_{14}$ is $NR_g$, and $R_g$ is each independently selected from hydroxy, cyano, halogen atom, $C_{1-6}$alkyl, $C_{1-6}$alkoxyl, $C_{1-6}$alkoxyl $C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl or 5-10-membered heteroaryl, preferably, $R_g$ is each independently selected from hydroxy, cyano, halogen atom, branched $C_{1-6}$alkyl, 3-membered cycloalkyl or 4-membered cycloalkyl.

In another embodiment of the present invention, in formula a, when $Z_1$, $Z_2$, $Z_3$ and $Z_4$ are all $CR_eR_f$ or $CR_e$, and the ring formed by $Z_1$, $Z_2$, $Z_3$ and $Z_4$ is bonded to the $L_1$ group, and m+q≥2, at least one of $Z_{11}$, $Z_{12}$, $Z_{13}$ and $Z_{14}$ is $NR_g$, and $R_g$ is each independently selected from hydroxy, cyano, halogen atom, branched $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-membered cycloalkyl or 4-membered cycloalkyl, preferably $R_g$ is each independently selected from hydroxy, cyano, halogen atom, branched $C_{1-6}$alkyl, 3-membered cycloalkyl or 4-membered cycloalkyl.

In another embodiment of the present invention, in formula I, q is 1, $Z_{14}$ represents C=O.

In another embodiment of the present invention, a situation where two or more carbonyl groups (C=O) are directly bonded is not present in the structural formula of the compound represented by Formula I.

In another embodiment of the present invention, in formula I, m+q=2, at least one of $Z_{12}$ and $Z_{14}$ represents C=O.

In another embodiment of the present invention, in formula I, $Z_{11}$, $Z_{12}$, $Z_{13}$ and $Z_{14}$ are not N or $NR_g$ at the same time.

In another embodiment of the present invention, in formula I, $Z_8$, $Z_9$, $Z_{10}$ and $Z_{11}$ are not N or $NR_g$ at the same time.

In another embodiment of the present invention, in formula I, at least one of $Z_{11}$, $Z_{12}$, $Z_{13}$ and $Z_{14}$ represents $NR_g$, and at least one of them represents C=O.

In another embodiment of the present invention, in formula I,
said $C_{y1}$ is the following group optionally substituted with a substituent:

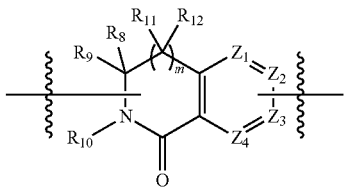

i

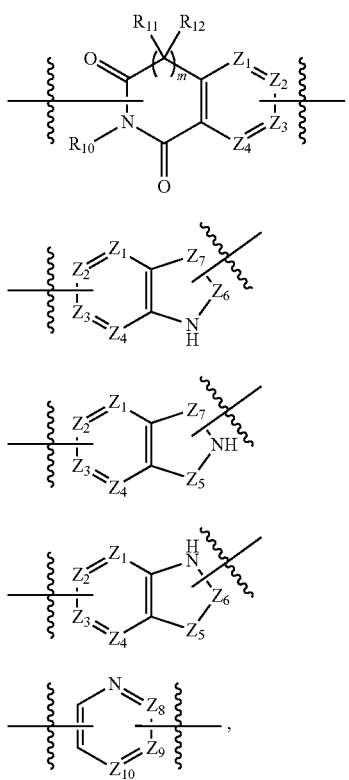

wherein, $Z_1$, $Z_2$, $Z_3$ and $Z_4$ are each independently selected from CH or N, $Z_5$, $Z_6$ and $Z_7$ are each independently selected from $CH_2$ or NH, $Z_8$, $Z_9$, and $Z_{10}$ are each independently selected from CH or N, and not N at the same time, $R_8$, $R_9$, $R_{11}$ and $R_{12}$ are each independently selected from hydrogen, hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl, 5-10-membered heteroaryl, or, at least one pair of $R_8$ and $R_9$, and $R_{11}$ and $R_{12}$ may form a 3-6 membered cycloalkyl with the atom to which they are attached, or, either $R_8$ or $R_9$, and, either $R_{11}$ or $R_{12}$ may form a 3-6 membered ring with the atoms to which they are attached; or, the atom(s) on $C_{y1}$ may also form a 4-7-membered ring together with the atoms in $R_6$ and $L_1$; or at least one pair of $R_8$ and $R_9$, and $R_{11}$ and $R_{12}$ may form an oxo group;

$R_{10}$ is selected from hydrogen, hydroxy, cyano, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl, and 5-10-membered heteroaryl, m is 0 or 1;

$R_7$ is each independently selected from hydrogen, hydroxy, amino, carboxyl, cyano, nitro, halogen atom, $C_{1-6}$alkyl, $R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 4-6-membered heterocyclyl optionally substituted with a substituent or 5-6-membered heteroaryl optionally substituted with a substituent, or, $R_a$ and $R_b$ may form a 4-6-membered ring with the atom to which they are attached; $C_{y2}$ is phenyl optionally substituted with a substituent, 4-6-membered heterocyclyl optionally substituted with a substituent, 5-6-membered heteroaryl optionally substituted with a substituent, n is an integral number of 0-3; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, 3-8-membered cycloalkyl, phenyl, 4-6-membered heterocyclyl, 5-6-membered heteroaryl.

In another embodiment of the present invention, in formula i and in formula ii, when at least one of $Z_1$, $Z_2$, $Z_3$ and $Z_4$ is N, and they are not N at the same time, the ring formed by $Z_1$, $Z_2$, $Z_3$ and $Z_4$ is bonded to the $L_1$ group.

In another embodiment of the present invention, in formula i, when the ring formed by $Z_1$, $Z_2$, $Z_3$ and $Z_4$ is bonded to the $L_1$ group, and m is 0, $R_{10}$ is selected from hydroxy, cyano, halogen atom, $C_{1-6}$alkyl, $C_{1-6}$alkoxyl, $C_{1-6}$alkoxyl $C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl or 5-10-membered heteroaryl, preferably $R_{10}$ is selected from hydroxy, cyano, halogen atom, branched $C_{1-6}$alkyl, 3-membered cycloalkyl or 4-membered cycloalkyl.

In another embodiment of the present invention, in formula i, when the ring formed by $Z_1$, $Z_2$, $Z_3$ and $Z_4$ is bonded to the $L_1$ group, and m is 1, $R_{10}$ is selected from hydroxy, cyano, halogen atom, branched $C_{1-6}$alkyl, $C_{1-6}$alkoxyl, $C_{1-6}$alkoxyl$C_{1-6}$alkoxyl, $C_{1-6}$alkylamino, $(C_{1-6}$ alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-membered cycloalkyl or 4-membered cycloalkyl, preferably $R_{10}$ is selected from hydroxy, cyano, halogen atom, branched $C_{1-6}$alkyl, 3-membered cycloalkyl or 4-membered cycloalkyl.

In another embodiment of the present invention, in formula iii, formula iv and formula v, the 5-membered ring is bonded to the $L_1$ group, and the 6-membered ring is bonded to $R_7$.

In another embodiment of the present invention, the compound represented by the above formula I is a compound represented by the following formula II, a pharmaceutically acceptable salt, an ester or a stereoisomer thereof:

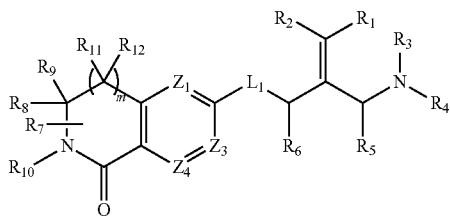

wherein, $R_1$ and $R_2$ are each independently selected from hydrogen, fluorine, chlorine, bromine, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is a bond, —CR'R''—, —O— and —S—, R' and R'' are each independently selected from hydrogen or $C_{1-6}$ alkyl;

$Z_1$, $Z_3$ and $Z_4$ are each independently selected from CH or N;

$R_8$, $R_9$, $R_{11}$ and $R_{12}$ are each independently selected from hydrogen, hydroxy, amino, carboxyl, cyano, nitro, halogen atom or $C_{1-6}$alkyl, or, at least one pair of $R_8$ and $R_9$, and R and $R_{12}$ may form a 3-6 membered cycloalkyl with the atom to which they are attached; or, either $R_8$ or $R_9$, and, either $R_{11}$ or $R_{12}$ may form a 3-6 membered cycloalkyl with the atoms to which they are attached; or $R_8$ and $R_9$ together may form an oxo group;

$R_{10}$ is selected from hydrogen, hydroxy, cyano, halogen atom, $C_{1-6}$alkyl or 3-6-membered cycloalkyl, m is 0 or 1;

$R_7$ is selected from hydrogen, hydroxy, amino, carboxyl, cyano, nitro, halogen atom or $C_{1-6}$alkyl.

In another embodiment of the present invention, at least one of $Z_1$, $Z_3$ and $Z_4$ is N.

In another embodiment of the present invention, in the compound represented by formula II, in case that m in the left ring carrying a carbonyl is 0. $R_{10}$ is selected from hydroxy, cyano, halogen atom, $C_{1-6}$alkyl or 3-6-membered cycloalkyl, preferably $R_{10}$ is selected from branched $C_{1-6}$alkyl, 3-membered cycloalkyl or 4-membered cycloalkyl.

In another embodiment of the present invention, in the compound represented by formula II, in case that m in the left ring carrying a carbonyl is 1, $R_{10}$ is selected from hydroxy, cyano, halogen atom, branched C-alkyl, 3-membered cycloalkyl or 4-membered cycloalkyl, preferably $R_{10}$ is selected from branched $C_{1-6}$alkyl, 3-membered cycloalkyl or 4-membered cycloalkyl.

In another embodiment of the present invention, there is provided the compound represented by the above formula II, a pharmaceutically acceptable salt, an ester or a stereoisomer thereof:

wherein, $R_1$ and $R_2$ are each independently selected from hydrogen, fluorine, and $R_1$ and $R_2$ are not hydrogen at the same time;

$R_3$ and $R_4$ are each independently selected from hydrogen or $C_{1-6}$ alkyl;

$R_5$ and $R_6$ each are hydrogen;

$L_1$ is —CR'R''— or —O—, R' and R'' are each independently selected from hydrogen or $C_{1-6}$alkyl;

$Z_1$, $Z_3$ and $Z_4$ are each independently selected from CH or N;

$R_8$, $R_9$, $R_{11}$ and $R_{12}$ are each independently selected from hydrogen or $C_{1-6}$alkyl, or, $R_8$ or $R_9$, with the atom to which they are attached, may form cyclopropane, cyclobutane, cyclopentane; or $R_8$ and $R_9$ together may form an oxo group;

$R_{10}$ is selected from branched $C_{1-6}$alkyl, 3-membered cycloalkyl or 4-membered cycloalkyl;

m is 0 or 1;

$R_7$ is hydrogen.

In another embodiment of the present invention, the compound represented by the above formula I is a compound represented by the following formula III, a pharmaceutically acceptable salt, an ester or a stereoisomer thereof:

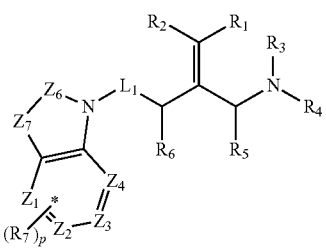

wherein, $R_1$ and $R_2$ are each independently selected from hydrogen, fluorine, chlorine, bromine, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is a bond, —CR'R''—, —O— and —S—, R' and R'' are each independently selected from hydrogen or $C_{1-6}$ alkyl;

$Z_1$, $Z_2$, $Z_3$ and $Z_4$ are each independently selected from CH or N, and not N at the same time;

$Z_6$ and $Z_7$ are each independently selected from $CH_2$ or NH;

p is an integral number of 1-4.

$R_7$ is each independently selected from hydrogen, hydroxy, amino, carboxyl, cyano, nitro, halogen atom, $C_{1-6}$alkyl,

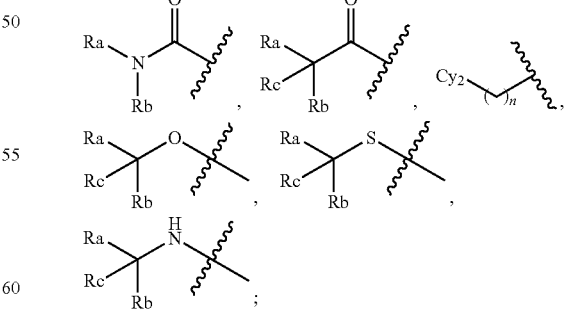

$R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 4-6-membered heterocyclyl optionally substituted with a substituent, 5-6-membered heteroaryl optionally substituted with a substituent, or, $R_a$ and $R_b$ may form a 4-6-membered ring with the atom to which they are attached; $C_{y2}$ is phenyl optionally substituted with a substituent, 4-6-membered heterocyclyl optionally substituted with a substituent, 5-6-membered heteroaryl optionally substituted with a substituent, n is an integral number of 0-3; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, 3-8-membered cycloalkyl, phenyl, 4-6-membered heterocyclyl, 5-6-membered heteroaryl.

In another embodiment of the present invention, there is provided the compound represented by the above formula III, a pharmaceutically acceptable salt, an ester or a stereoisomer thereof:

wherein, $R_1$ and $R_2$ are each independently selected from hydrogen, fluorine, and $R_1$ and $R_2$ are not hydrogen at the same time;

$R_3$ and $R_4$ are each independently selected from hydrogen or $C_{1-6}$ alkyl;

$R_5$ and $R_6$ each are hydrogen;

$L_1$ is a bond;

$Z_1$, $Z_2$, $Z_3$ and $Z_4$ are each independently selected from CH or N, and not N at the same time;

$Z_6$ and $Z_7$ are each independently selected from $CH_2$ or NH;

p is 1 or 2, $R_7$ is each independently selected from hydrogen, hydroxy, amino, carboxyl, cyano, nitro, halogen atom, $C_{1-6}$alkyl,

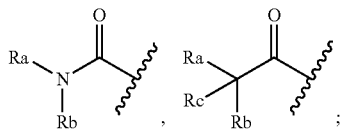

$R_a$, $R_b$ and $R_c$ are each independently selected from hydrogen, $C_{1-6}$alkyl optionally substituted with a substituent, said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, 3-8-membered cycloalkyl, phenyl, 4-6-membered heterocyclyl, 5-6-membered heteroaryl;

or, $R_a$ and $R_b$ may form a 4-6-membered ring with the atom to which they are attached.

In another embodiment of the present invention, in formula III, $Z_1$, $Z_2$, $Z_3$ and $Z_4$ are all CH.

In another embodiment of the present invention, in formula III, at most one of $Z_1$, $Z_2$, $Z_3$ and $Z_4$ is N.

In another embodiment of the present invention, the compound represented by the above formula I is a compound represented by the following formula IV, a pharmaceutically acceptable salt, an ester or a stereoisomer thereof:

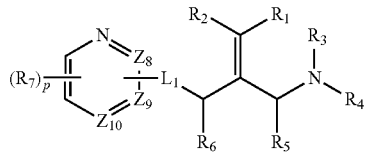

IV wherein, $R_1$ and $R_2$ are each independently selected from hydrogen, fluorine, chlorine, bromine, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is —CR'R"—, —O— and —S—, R' and R" are each independently selected from hydrogen or $C_{1-6}$ alkyl;

$Z_8$, $Z_9$ and $Z_{10}$ are each independently selected from CH or N, and not N at the same time; the atom(s) on the group

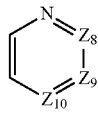

may also form a 4-7-membered ring with the atoms in $R_6$ and $L_1$;

p is an integral number of 1-4, $R_7$ is each independently selected from hydrogen, hydroxy, amino, carboxyl, cyano, nitro, halogen atom, $C_{1-6}$alkyl,

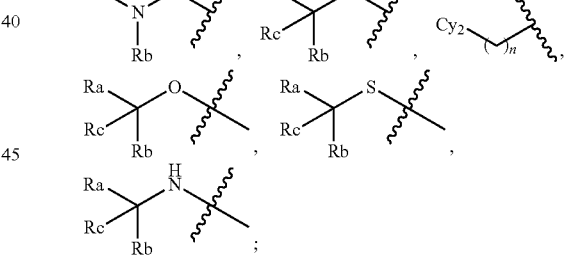

$R_a$, $R_b$ and $R_c$ are each independently selected from hydrogen, or $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 4-6-membered heterocyclyl optionally substituted with a substituent, 5-6-membered heteroaryl optionally substituted with a substituent, or, $R_a$ and $R_b$ may form a 4-6-membered ring with the atom to which they are attached; $C_{y2}$ is phenyl optionally substituted with a substituent, 4-6-membered heterocyclyl optionally substituted with a substituent, 5-6-membered heteroaryl optionally substituted with a substituent, n is an integral number of 0-3; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, ($C_{1-6}$alkyl)$_2$amino, $C_{1-6}$alkylcarbonylamino, $C_{1-6}$alkylsulfonylamino, 3-8-membered cycloalkyl, phenyl, 4-6-membered heterocyclyl, 5-6-membered heteroaryl.

In another embodiment of the present invention, there is provided the compound represented by the above formula IV, a pharmaceutically acceptable salt, an ester or a stereoisomer thereof:

wherein, $R_1$ and $R_2$ are each independently selected from hydrogen, fluorine, and $R_1$ and $R_2$ are not hydrogen at the same time;

$R_3$ and $R_4$ are each independently selected from hydrogen or $C_{1-6}$ alkyl;

$R_5$ and $R_6$ each are hydrogen;

$L_1$ is —CR'R"— or —O—, R' and R" are each independently selected from hydrogen or $C_{1-6}$ alkyl;

$Z_8$, $Z_9$ and $Z_{10}$ are each independently selected from CH;

p is 1 or 2, $R_7$ is each independently selected from hydrogen, hydroxy, amino, carboxyl, cyano, nitro, halogen atom, $C_{1-6}$alkyl,

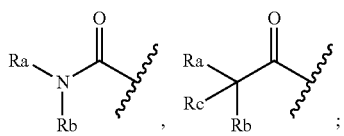

$R_a$, $R_b$ and $R_c$ are each independently selected from hydrogen, $C_{1-6}$alkyl optionally substituted with a substituent, said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, ($C_{1-6}$alkyl)$_2$amino, $C_{1-6}$alkylcarbonylamino, $C_{1-6}$alkylsulfonylamino, 3-8-membered cycloalkyl, phenyl, 4-6-membered heterocyclyl, 5-6-membered heteroaryl;

or, $R_a$ and $R_b$ may form a 4-6-membered ring with the atom to which they are attached.

In another embodiment of the present invention, there is provided the following compound, a pharmaceutically acceptable salt, an ester or a stereoisomer thereof:

| No | Structural Formula |
|----|-------------------|
| 2 | |
| 4 | |
| 5 | |
| 6 | |
| 7 | |
| 8 | |
| 9 | |
| 13 | |
| 14 | |

-continued
| No | Structural Formula |
|---|---|
| 15 | 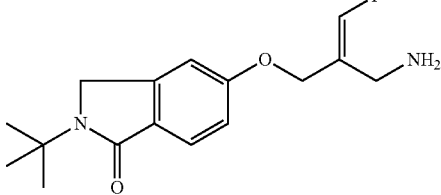 |
| 16 | 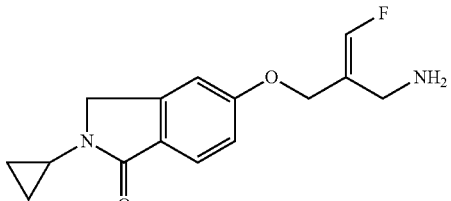 |
| 17 | 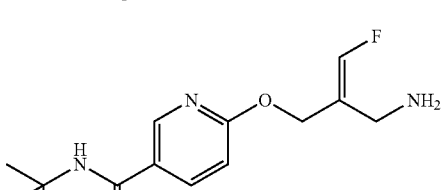 |
| 18 | 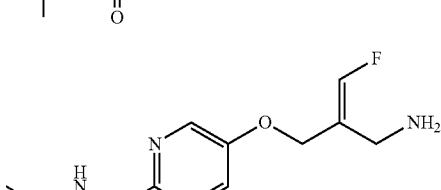 |
| 19 | 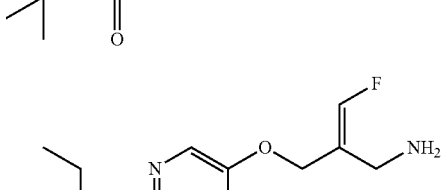 |
| 20 | 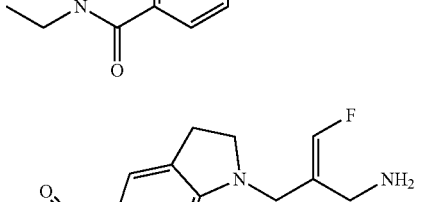 |
| 21 | 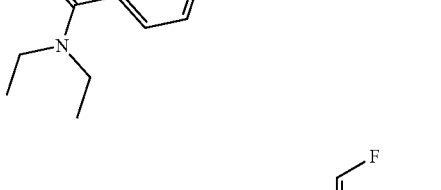 |
-continued
| No | Structural Formula |
|---|---|
| 22 | 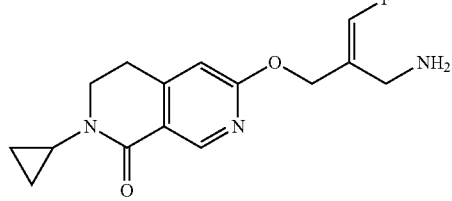 |
| 23 | 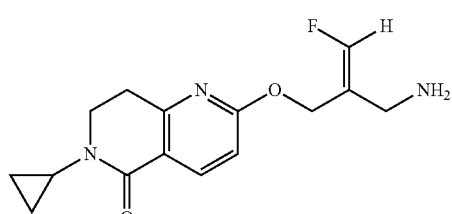 |
| 24 | 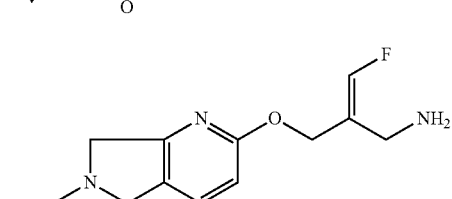 |
| 25 | 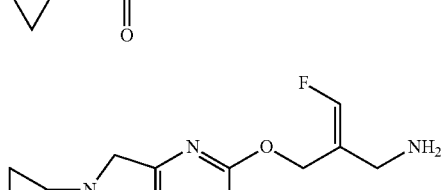 |
| 26 | 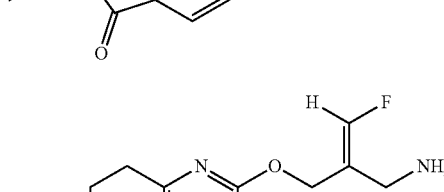 |
| 27 | 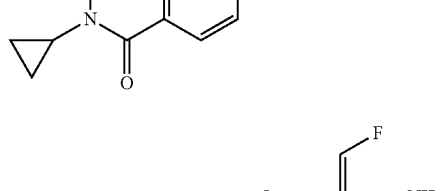 |
| 28 | 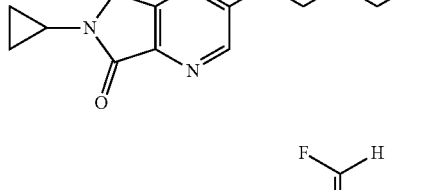 |

| No | Structural Formula |
|---|---|
| 29 | (cyclopropyl-isoindolinone with -O-CH2-C(=CHF)-CH2-NH2 substituent) |
| 30 | (cyclopropyl-phthalimide with -O-CH2-C(=CHF)-CH2-NH2 substituent) |
| 31 | (cyclopropyl-phthalimide isomer with -O-CH2-C(=CHF)-CH2-NH2 substituent) |
| 32 | (cyclopropyl tetrahydronaphthyridinone with -O-CH2-C(=CHF)-CH2-NH2 substituent) |
| 33 | (cyclopropyl pyrrolopyridinone with -O-CH2-C(=CHF)-CH2-NH2 substituent) |
| 34 | (cyclopropyl dihydroisoquinolinone with -O-CH2-C(=CHF)-CH2-NH2 substituent) |

In another technical solution of the present invention, there is provided a pharmaceutical composition containing a compound represented by formula I, II, III or IV, a pharmaceutically acceptable salt, an ester or a stereoisomer thereof, in which the composition may optionally contain one or more pharmaceutically acceptable supports.

In another technical solution of the present invention, the pharmaceutical composition may be administered by any suitable means known in the art, for example, orally, parenterally (including subcutaneously, intramuscularly, intravenously, intraarterially, intradermally, intrathecally and epidurally), transdermally, rectally, nasally, transpulmonarily, topically (including orally and sublingually), vaginally, intraperitoneally, intrapulmonarily and intranasally, to a patient or a subject in need of such prevention and/or treatment.

In another technical solution of the present invention, the pharmaceutical composition can be made into conventional solid preparations, such as tablets, capsules, pills, and granules; or can also made into oral liquid preparations, such as oral solutions, oral suspensions, and syrups. For making into oral preparations, one or more of bulking agent, binder, disintegrant, lubricant and the like can be suitably added. For parenteral administration, the pharmaceutical composition can be made into injections, including injection liquid, sterile powder for injection and concentrated solution for injection. Upon making into injections, the conventional production methods known in the pharmaceutical field can be used, and upon formulating the injection, an additional agent may not be added, or a suitable additional agent can be added according to the drug properties. For rectal administration, the pharmaceutical composition can be made into suppositories and the like. For transpulmonary administration, the pharmaceutical composition can be made into inhalations or aerosols and the like.

In another technical solution of the present invention, there is provided use of a compound represented by formula I, II, III or IV, a pharmaceutically acceptable salt, an ester or a stereoisomer thereof in manufacture of a medicament for preventing and/or treating the SSAO/VAP-1 protein-related or SSAO/VAP-1 protein-mediated disease.

In another technical solution of the present invention, there is provided a method of preventing and/or treating the SSAO/VAP-1 protein-related or SSAO/VAP-1 protein-mediated disease, in which the method comprises administrating a compound represented by formula I, II, III or IV, a pharmaceutically acceptable salt, an ester or a stereoisomer thereof to a subject.

In another technical solution of the present invention, there is provided a compound represented by formula I, II, III or IV, a pharmaceutically acceptable salt, an ester or a stereoisomer thereof for preventing and/or treating the SSAO/VAP-1 protein-related or SSAO/VAP-1 protein-mediated disease.

In another technical solution of the present invention, there is provided use of the above pharmaceutical composition in preventing and/or treating the SSAO/VAP-1 protein-related or SSAO/VAP-1 protein-mediated disease.

Effects of the Invention

The present invention provides a novel haloallylamine compound, which is effective in treating and/or preventing the SSAO/VAP-1 protein-related or SSAO/VAP-1 protein-mediated disease. Specifically, the compound represented by formula I, II, III or IV according to the present invention, a pharmaceutically acceptable salt, an ester or a stereoisomer thereof shows a strong inhibition activity to the SSAO/VAP-1 protein. Moreover, the compound of the present invention shows an excellent specific selectivity for the SSAO/VAP-1 protein compared with the monoamine oxidase (MAO).

Therefore, the present invention may provide a medicament for specifically preventing and/or treating the SSAO/VAP-1 protein-related or SSAO/VAP-1 protein-mediated disease.

DETAILED DESCRIPTION OF THE INVENTION

The embodiments of the present invention will be described in more detail below with reference to the specific embodiments, but those skilled in the art will understand that the specific embodiments described below are only used to illustrate the invention, and should not be regarded as the limit to the protection scope of the present invention. Rather, the invention is intended to cover all alternatives, modifications and equivalents, which are included in the scope of the invention as defined by the appended claims. Embodiments of the invention may be combined in any manner, unless otherwise stated. Conversions, variations, and modifications of the technical solutions thus obtained are also included in the scope of the resent invention and do not depart from the scope of the present invention.

Definition

In the present invention, the expression "$C_{a-b}$ group" (a and b represent integers of one or more, a<b) means that the "group" has a-b carbon atoms, for example, $C_{1-4}$alkyl represents an alkyl having 1-4 carbon atoms, $C_{1-4}$alkoxy represents an alkoxy having 1-4 carbon atoms, $C_{3-10}$cycloalkyl represents a cycloalkyl having 3-10 carbon atoms, and $C_{1-4}$alkoxy$C_{1-4}$alkyl represents a group formed by attaching an alkoxy having 1-4 carbon atoms to an alkyl having 1-4 carbon atoms.

As mentioned in the present invention, "halogen" or "halogen atom" refers to a fluorine atom, a chlorine atom, a bromine atom, or an iodine atom. It is preferably a fluorine atom, or a chlorine atom.

According to the present invention, "halo" refers to such a condition, in which the hydrogen atom(s) on any carbon atom in a group is/are substituted by one or more same or different halogens or halogen atoms. "Halogen" or "halogen atom" are as defined above. Fluoro or chloro is preferable.

As mentioned in the present invention, "$C_{1-6}$alkyl" refers to a linear or branched alkyl obtained derivatively by removing one hydrogen atom from an alkane containing 1-6 carbon atoms, which comprises linear $C_{1-6}$alkyl and branched $C_{1-6}$alkyl. In fact, it is well known by those skilled in the art that, in case that $C_{1-6}$alkyl has a branched chain (branched $C_{1-6}$alkyl), it has at least three carbon atoms. As an example of "$C_{1-6}$alkyl", for example, methyl, ethyl, n-propyl, isopropyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like can be exemplified. Said "$C_{1-4}$alkyl" refers to those containing 1-4 carbon atoms in the above-mentioned examples.

As mentioned in the present invention, "$C_{2-6}$alkenyl" refers to a linear or branched alkenyl obtained derivatively by removing one hydrogen atom from an alkene containing at least one C—C double bond and 2-6 carbon atoms, for example, ethenyl, 1-propenyl, 2-propenyl, 1-butenyl, 2-butenyl, 1,3-butadiene-1-yl, 1-pentene-3-yl, 2-pentene-1-yl, 3-pentene-1-yl, 3-pentene-2-yl, 1,3-pentadiene-1-yl, 1,4-pentadiene-3-yl, 1-hexene-3-yl, 1,4-hexadiene-1-yl can be exemplified. Preferably, "$C_{2-6}$alkenyl" contains one C—C double bond.

As mentioned in the present invention, "$C_{2-6}$alkynyl" refers to a linear or branched alkynyl obtained derivatively by removing one hydrogen atom from an alkyne containing at least one C—C triple bond and 2-6 carbon atoms, for example, ethynyl, propynyl, 2-butyn-1-yl, 2-pentyn-1-yl, 3-pentyn-1-yl, 4-methyl-2-pentyn-1-yl, 2-hexyn-1-yl, 3-hexyn-2-yl, 3-hexyn-1-yl, 3-hexyn-2-yl and the like can be exemplified. Preferably, "$C_{2-6}$alkynyl" contains one C—C triple bond.

As mentioned in the present invention, "$C_{1-6}$alkoxy" refers to the group obtained from the above-defined "$C_{1-6}$alkyl" by attaching to the parent group via an oxygen atom, i.e. the group "$C_{1-6}$alkyl-O—", for example, methoxy, ethoxy, n-propoxy, iso-propoxy, n-butoxy, tert-butoxy, n-pentyloxy, neo-pentyloxy and n-hexyloxy, and the like can be exemplified. "$C_{1-4}$alkoxy" refers to those containing 1-4 carbon atoms in the above-mentioned examples, i.e. the group "$C_{1-4}$alkyl-O—". Said "$C_{1-6}$alkoxyl$C_{1-6}$alkoxyl" refers to a group formed by replacing one or more hydrogen atoms of $C_{1-6}$alkoxyl with $C_{1-6}$alkoxyl group(s).

As mentioned in the present invention, "$C_{1-6}$alkylamino", "($C_{1-6}$alkyl)$_2$amino", "$C_{1-6}$alkylcarbonylamino", "$C_{1-6}$alkylsulfonylamino", "$C_{1-6}$alkylsulfonyl", and "$C_{1-6}$alkylthio" refer to the groups formed by attaching $C_{1-6}$alkyl to —NH$_2$, —CO—NH$_2$—, —SO$_2$NH$_2$—, —SO$_2$—, and —S— respectively. For example, those formed by attaching the groups exemplified in the above "$C_{1-6}$alkyl" to —NH$_2$, —CO—NH$_2$—, —SO$_2$NH$_2$—, —SO$_2$—, and —S— respectively can be exemplified.

As mentioned in the present invention, "polycyclic ring" refers to a polycyclic ring system formed from two or more cyclic structures and in form of fused ring, bridged ring and spiro ring. Said fused ring refers to a polycyclic ring structure formed from two or more cyclic structures, wherein each two cyclic structure shares two adjacent ring-forming atoms (i.e. commonly uses one bond). Said bridged ring refers to a polycyclic ring structure formed from two or more cyclic structures, wherein each two cyclic structure shares two non-adjacent ring-forming atoms. Said spiro ring refers to a polycyclic ring structure formed from two or more cyclic structures, wherein each two cyclic structure shares one ring-forming atom.

As mentioned in the present invention, "cycloalkyl" refers to a monovalent group or a divalent (as required) formed from a cycloalkane. Said cycloalkane comprises a monocyclic cycloalkane or a polycyclic cycloalkane. For example, it can have 3, 4, 5, 6, 7, 8, 9, 10, 11 or 12 carbon atoms. The cycloalkyl can be a 3-12-membered monovalent or divalent (as required) group, a 3-8-membered monovalent or divalent (as required) group, a 3-6-membered monovalent or divalent (as required) group, or a 5-7-membered monovalent or divalent (as required) group.

The monocyclic cycloalkyl can be 3-12-membered cycloalkyl, 3-8-membered cycloalkyl, 3-6-membered cycloalkyl, or 5-7-membered cycloalkyl. Its example includes but is not limited to cyclopropyl, cyclobutyl, cyclopentyl, cyclohexyl, cycloheptyl, cyclooctyl, cyclopentane-1,3-diyl, cyclohexane-1,4-diyl, cycloheptane-1,4-diyl and the like.

The polycyclic cycloalkyl comprises fused cycloalkyl, bridged cycloalkyl, and spiro cycloalkyl.

As mentioned in the present invention, "cycloalkenyl" refers to the group derivable from the above-mentioned cycloalkyl but having at least one double bond, preferably one double bond.

The fused cycloalkyl can be 6-12-membered fused cycloalkyl, or 7-10-membered fused cycloalkyl. Its example includes but is not limited to bicyclo[3.1.1]heptane, bicyclo

[2.2.1]heptane, bicyclo[2.2.2]octane, bicyclo[3.2.2]nonane, bicyclo[3.3.1]nonane and bicyclo[4.2.1]nonane.

"Cycloalkyl" and "cycloalkenyl" may also be a monovalent group formed by removing one hydrogen atoms from 6-12-membered spiro ring or 7-11-membered spiro ring, or as required, a divalent group formed by removing one hydrogen atom respectively from two different carbon atoms. The example of said spiro ring includes but is not limited to

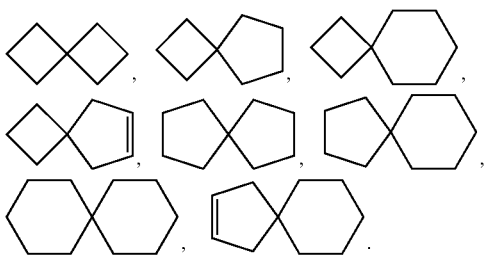

"Cycloalkyl" and "cycloalkenyl" may also be a monovalent group formed by removing one hydrogen atoms from 6-12-membered bridge ring or 7-11-membered bridge ring, or as required, a divalent group formed by removing one hydrogen atom respectively from two different carbon atoms. The example of said bridge ring includes but is not limited to

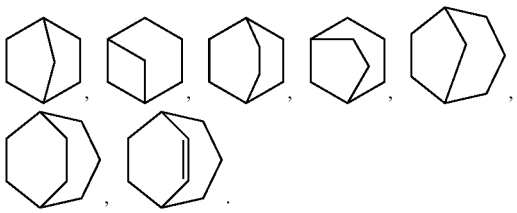

Therefore, as mentioned in the present invention, "3-12-membered cycloalkenyl", unless otherwise specified, comprises all possible monocyclic and polycyclic rings (including fused ring, spiro ring and bridged ring). It is a group derivable from the above-mentioned/exemplified 3-12-membered monovalent or divalent (as required) cycloalkyl but having at least one double bond. It can be a monovalent or divalent group derivable from 3-8-membered cycloalkene, 7-11-membered sprio-ring cycloalkene, 7-11-membered fused-ring cycloalkene, 6-11-membered bridged-ring cycloalkane and the like. The example of cycloalkenyl includes but is not limited to cyclobutenyl, cyclopentenyl, cyclohexenyl, 1,4-cyclohexadiene-1-yl, cycloheptenyl, 1,4-cycloheptadiene-1-yl, cyclooctenyl, 1,5-cyclooctadiene-1-yl and the like.

As mentioned in the present invention, "heterocyclyl" refers to a non-aromatic monovalent or divalent cyclic group obtained derivatively by replacing at least one ring-forming carbon atom of the above-mentioned cycloalkyl with at least one heteroatom selected from a group consisting of O, S and N, preferably 1-3 heteroatoms, preferably having 0 or 1 carbon-carbon double bond. In addition, the heterocyclyl also comprises such a situation, in which the ring-forming carbon atom or the ring-forming sulfur atom is oxidized or nitridized, for example, the carbon or sulfur atom is replaced with C(=O), S(=O), S(=O)$_2$, or S(=O)(=N).

Specifically, the "heterocyclyl" may be a group having 3, 4, 5, 6, 7, 8, 9, 10, 11 or 12 ring-forming atoms. It can be 3-12-membered heterocyclyl, 4-12-membered heterocyclyl, 5-10-membered heterocyclyl, including a monocyclic heterocycyl or a polycyclic heterocycyl. The monocyclic heterocycyl can be 3-12-membered heterocyclyl, 3-8-membered heterocyclyl, 3-8-membered saturated heterocyclyl, 3-6-membered heterocyclyl, 4-12-membered heterocyclyl, 4-7-membered heterocyclyl, 4-6-membered heterocyclyl, 5-10-membered heterocyclyl, 5-7-membered heterocycyl, 5-6-membered heterocyclyl, 5-6-membered oxygen-containing heterocyclyl, 5-6-membered nitrogen-containing heterocyclyl, 5-6-membered saturated heterocyclyl, 5-7-membered saturated heterocyclyl and the like, which may be saturated, partially saturated or unsaturated, but not aromatic. Its example includes but is not limited to: aziridinyl, 2H-aziridinyl, diaziridinyl, 3-diazirinyl, azetidinyl, 1,4-dioxanyl, 1,3-dioxanyl, 1,3-dioxolanyl, 1,4-diox adienyl, tetrahydrofuryl, diliydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, piperidinyl, piperazinyl, morpholinyl, hexahydropyrimidyl, hexahydropyridazinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-onyl, 3,4-dihydro-2H-pyranly, 1-dioxotetrahydrothiopyranyl, 1-dioxoletrahydrothiothienyl, 1-imino-1-oxo-tetrahydrothiacyclobutanyl, 1-imino-1-oxo-tetrahydrtothiothienyl, 1-imino-1-oxo-hexahydrothiopyranyl, and the like.

The polycyclic heterocycyl comprises fused heterocyclyl, spiro heterocyclyl, bridged heterocyclyl, which may be saturated, partially saturated or unsaturated, but not aromatic.

Said fused heterocyclyl can be 6-12-membered fused heterocyclyl, 7-10-membered fused heterocyclyl, 6-12-membered saturated fused heterocyclyl, 7-8-membered saturated fused heterocyclyl, 8-membered saturated fused heterocyclyl, its example concludes but is not limited to: 3-azabicyclo[3.1.0]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuran-3-yl, indoline-1-yl, indoline-2-yl, indoline-3-yl, 2,3-dihydrobenzothiophene-2-yl, octahydro-1H-indolyl, octahydrobenzofuranyl, octahydrocyclopenta[c]pyrrolyl, hexahydrocyclopenta[c]furanyl, 2,2-dioxohexahydrocyclopenta[c]thienyl, 2-imino-2-oxo-octahydrocyclopenta[c]thienyl.

Said spiro heterocyclyl can be a monvalent group obtained by removing one hydrogen atom from 6-12-membered spiro heterocycle, 7-11-membered spiro heterocycle, 6-12-membered saturated spiro heterocycle, or 7-membered saturated spiro heterocycle, or as required, a divalent group obtained by removing one hydrogen atom respectively from two different carbon atoms of the spiro heterocycle. The example of the spiro heterocycle includes but is not limited to

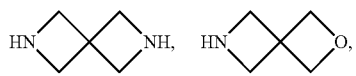

-continued

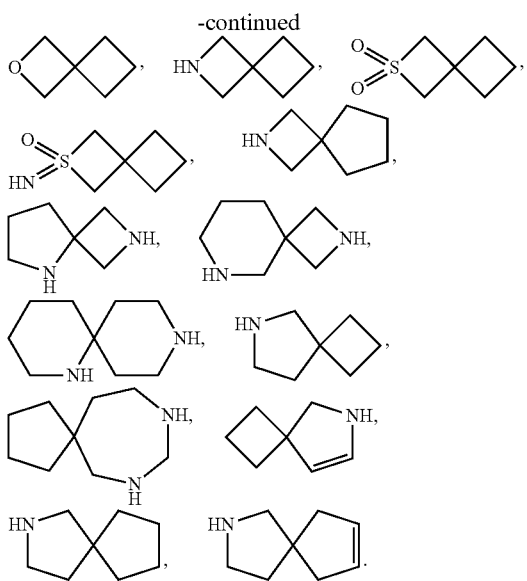

Said bridged heterocyclyl can be a monvalent group obtained by removing one hydrogen atom from 6-12-membered bridged heterocycle, 7-11-membered bridged heterocycle, 6-12-membered saturated bridged heterocycle, or 7-8-membered saturated bridged heterocycle, or as required, a divalent group obtained by removing one hydrogen atom respectively from two different carbon atoms of the bridged heterocycle. The example of the bridged heterocycle includes but is not limited to:

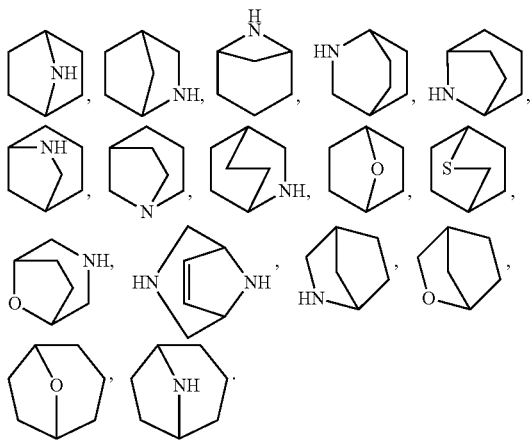

As mentioned in the present invention, "aryl" refers to monovalent or divalent group (as required) obtained derivatively from aromatic carboneous cyclic hydrocarbon, which comprises 6-8-membered monocyclic aromatic hydrocarbon, or 8-14-membered polyocyclic aromatic hydrocarbon. 6-8-membered monocyclic aryl is for example phenyl. 8-14-membered polyocyclic aryl is for example naphthalenyl, phenanthrenyl, and anthracenyl and the like. When it is a divalent group, phenylene, naphthalenediyl and the like can be exemplified.

As mentioned in the present invention, "heteroaryl" can be 5-14-membered heteroaryl, 5-10-membered heteroaryl, 5-6-membered heteroaryl. It refers to an aromatic monovalent or divalent cyclic hydrocarbyl containing at least one, preferably 1-3 heteroatoms selected from a group consisting of O, S and N and having a ring-forming atom number of 5, 6, 7, 8, 9, 10, 11, 12, 13 or 14. In addition, heteroaryl also comprises such a situation, in which the ring-forming carbon atom or the ring-forming sulfur atom is oxidized or nitridized, for example, the carbon or sulfur atom is replaced with $C(=O)$, $S(=O)$, $S(=O)_2$, or $S(=O)(=N)$. Heteroaryl comprises nonocyclic heteroaryl and polycyclic heteroaryl. The monocyclic heteroaryl can be 5-7-membered heteroaryl, 5-6-membered heteroaryl, and its example includes but is not limited to furanyl, imidazolyl, soxazolyl, thiazolyl, isothiazolyl, oxadiazolyl, oxazolyl, isoxazolyl, pyridinyl, pyridonyl, pyridazinyl, pyrimidinyl, pyrazinyl, pyrazolyl, pyrrolyl, tetrazolyl, thiadiazolyl, thiazolyl, thienyl, triazolyl and triazinyl. Polycyclic heteroaryl can be 8-12-membered fused heteroaryl, or 9-10-membered fused heteroaryl, and its example concludes but is not limited to benzoimidazolyl, benzofuranyl, benzothienyl, benzothienyl, benzooxadiazolyl, benzothiazolyl, cinnolinyl, indazolyl, indolyl, isoindolyl, isoquinolinyl, naphthyridinyl, purinyl, quinolinyl. Said heteroaryl can also be the divalent group derived from the above-mentioned groups.

The "3-6 membered ring", 3-8 membered ring", "4-6 membered ring", "4-7 membered ring" in the present invention refers to a chemically feasible cyclic structure of 3-6 ring-forming atoms, 3-8 ring-forming atoms, 4-6 ring-forming atoms, 4-7 ring-forming atoms, which may be optionally selected from C, N, O, S, $C(=O)$, $S(=O)_2$, $S(=O)(=NH)$, and the formed cyclic structure may be a monocyclic ring, a fused polycyclic ring, a saturated ring, a partially saturated ring, or an aromatic ring. Specifically, the above-mentioned cycloalkyl, cycloalkenyl, heterocyclyl, aryl and heteroaryl can be exemplified.

The term "pharmaceutically acceptable salt" as used herein refers to pharmaceutically acceptable acid or base addition salts of the compounds of formulae I, II, III and IV. When an acidic functional group (e.g., —COOH, —OH, —SO$_3$H, etc.) is present in the compound, salts formed with suitable inorganic or organic cations (bases) include salts formed with alkali or alkaline earth metals, ammonium salts, and salts formed with nitrogen-containing organic bases. When a basic functional group (e.g., —NH$_2$, etc.) is present in the compound, salts formed with suitable inorganic or organic anions (acids) include salts formed with inorganic acids, and salts formed with organic acids. Such "pharmaceutically acceptable salts" include, but are not limited to, salts of acids: salts with hydrochloric acid, trifluoroacetic acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acids such as acetic acid, HOOC—(CH$_2$)$_n$—COOH (wherein n is 0 to 4), and the like; salts of bases: sodium salt, potassium salt, calcium salt, ammonium salt, magnesium salt, and the like.

According to the present invention, during the reaction procedure, the N atom of the amino group may be optionally protected with an amino protecting group. "Amino protecting group" refers to a chemical group attached to an amino group and readily removed under certain conditions, and includes, but is not limited to, alkoxycarbonyl, acyl, alkyl; for example, t-butoxycarbonyl, benzyloxycarbonyl, fluorenylmethyloxycarbonyl, allyloxycarbonyl, phthaloyl, benzyl, p-methoxybenzyl, trityl and the like. Those skilled in the art can make appropriate selections and operations with reference to the textbook Greene's Protective Groups in Organic Synthesis (4$^{th}$ edition) commonly used in the art.

The term "optionally substituted" means that any part of the moiety known to those skilled in the art to be available for substitution may be unsubstituted or substituted with a substituent as described herein, wherein if more than one substituent is present, each substituent is independently selected.

The phrase "pharmaceutically acceptable" means that the substance or composition must be pharmaceutically and/or toxicologically compatible with the other ingredients included in the formulation and/or pharmaceutical composition.

The "isomer" of the present invention means that when an asymmetric atom exists in the compounds of the formulae I, II, III and IV, enantiomers will be generated; when carbon-carbon double bond or cyclic structure is present in the compound, cis and trans isomers will be generated; when a compound is present as ketone or oxime, tautomers will be generated. All of enantiomers, diastereomers, racemates, cis-trans isomers, tautomers, geometric isomers, epimers and mixtures thereof of the compounds of formulae I, II, III and IV are included within the scope of the present invention.

The pharmaceutical compositions of the present invention comprise at least one of the compounds represented by formulae I, II, III and IV, pharmaceutically acceptable salts, esters or stereoisomers thereof, and optionally one or more pharmaceutically acceptable supports.

The pharmaceutical composition of the present invention can be administered by any suitable means known in the art, for example, orally, parenterally (including subcutaneously, intramuscularly, intravenously, intraarterially, intradermally, intrathecally and epidurally), transdermally, rectally, nasally, transpulmonarily, topically (including orally and sublingually), vaginally, intraperitoneally, intrapulmonarily and intranasally, to a patient or a subject in need of such prevention and/or treatment.

The pharmaceutical composition of the present invention can be made into conventional solid preparations, such as tablets, capsules, pills, and granules; or can also made into oral liquid preparations, such as oral solutions, oral suspensions, and syrups. For making into oral preparations, one or more of excipient, diluent, sweetener, solubilizer, lubricant, binder, tablet disintegrant, stabilizer, preservative or encapsulating material can be suitably added. For parenteral administration, the pharmaceutical composition can be made into injections, including injection liquid, sterile powder for injection and concentrated solution for injection. Upon making into injections, the conventional production methods known in the pharmaceutical field can be used, and upon formulating the injection, an additional agent may not be added, or a suitable additional agent can be added according to the drug properties. For rectal administration, the pharmaceutical composition can be made into suppositories and the like. For trans pulmonary administration, the pharmaceutical composition can be made into inhalations or aerosols and the like. According to the present invention, suitable solid supports include, but are not limited to, for example, cellulose, glucose, lactose, mannitol, magnesium stearate, magnesium carbonate, sodium carbonate, sodium saccharin, sucrose, dextrin, talc, starch, pectin, gelatin, tragacanth, acacia, sodium alginate, parabens, methylcellulose, sodium carboxymethylcellulose, low melting wax, cocoa butter and the like. Suitable liquid support includes but is not limited to water, ethanol, polyol (e.g. glycerol, propylene glycol, liquid polyethylene glycol and the like), vegetable oil, glyceride and mixture thereof.

Methods for preparing the pharmaceutical composition of the present invention are generally known. The preparation of the pharmaceutical composition of the present invention in a known manner includes conventional methods of mixing, granulating, tableting, coating, dissolving or lyophilizing.

The pharmaceutical formulation is preferably in unit dosage form. In this form, the formulation is subdivided into unit dosages containing appropriate quantities of the active ingredient. The unit dosage form can be packaged in a package containing discrete quantities of the formulation, such as a packaged tablet, a capsule, or a powder in a vial or ampule.

The dosage of the drug to be administered depends on various factors including the age, weight and condition of the patient and the route of administration. The precise dosages to be administered will be determined based on the judgment of the treating physician. Typical dosages for administration of the active compound would be, for example, from about 0.01 to about 100 mg per day, from about 0.05 to about 75 mg per day, from about 0.1 to about 50 mg per day, or from about 5 to about 10 mg per day per day. The desired dosage will also depend on the particular compound employed, the severity of the disease, the route of administration, the weight and condition of the patient, and the judgment of the treating physician.

The compound of the present invention may further contain a compound in which one or more of a hydrogen atom, a fluorine atom, a carbon atom, a nitrogen atom, an oxygen atom, and a sulfur atom is/are replaced with a radioisotope or a stable isotope. These labeled compounds are useful for metabolic or pharmacokinetic studies, biological analyses as ligands for receptors, and the like.

The compound of the present invention may be used for treating and/or preventing the SSAO/VAP-1 protein-related or SSAO/VAP-1 protein-mediated disease, comprising administering to a subject the compound of the present invention.

The pharmaceutical composition containing the compound of the present invention may be used for treating and/or preventing the SSAO/VAP-1 protein-related or SSAO/VAP-1 protein-mediated disease, comprising administering to a subject the compound of the present invention.

EXAMPLES

In case that the specific reaction conditions are not indicated in the examples, these examples are carried out according to the conventional conditions or the conditions recommended by the manufacturer. In case that the manufacturer of the reagents or instruments used are not indicated, these reagents or instruments are conventional products which are commercially available.

In the present invention, unless otherwise stated, wherein: (i) the temperature is expressed in degrees Celsius (° C.), the operation is carried out at room temperature; (ii) the reaction is traced by thin layer chromatography (TLC) or LC-MS; (iii) the final products have clear proton nuclear magnetic resonance spectroscopy ($^1$H-NMR) data and the mass spectrometry (MS) data.

The abbreviations and English expressions used in the present invention have the following meanings.

DAST: diethylaminosulfur trifluoride
DCM: dichloromethane
-Boc: tert-butoxycarbonyl
TEA: triethylamine
TBSCl: tert-butyldimethylchlorosilane TBS-: tert-butyldimethylsilyl
DMSO: dimethyl sulfoxide
NaHMDS: sodium hexamethyldisilazide
TBAF: tetrabutylammonium fluoride
MsCl: methanesulfonyl chloride
TEA: trifluoroacetic acid
DMF: N,N-dimethylformamide
Pd₂(dba)₃: Tris(dibenzylideneacetone)dipalladium
conc.HCl: concentrated hydrochloric acid
NBS: N-bromosuccinimide
AIBN: azodiisobutyronitrile
TH: tetrahydrofuran
TMSCN: Trimethylsilyl cyanide
CPBA: m-chloroperoxybenzoic acid
TMSI: trimethylsilyl imidazole
BHT: dibutylhydroxytoluene
Pd(PPh₃)₂Cl₂: bis(triphenylphosphine) dichloropalladium
EA: ethyl acetate
MTBE: methyltert-butyl ether
PE: petroleum ether
HATU: 2-(7-azabenzotriazole-1-yl)-tetramethyluronium hexafluorophosphate
reflux: reflux Example 1: Synthesis of Intermediate (E)-tert-butyl (2-(bromomethyl)-3-fluoroallyl)carbamate Flow chart:

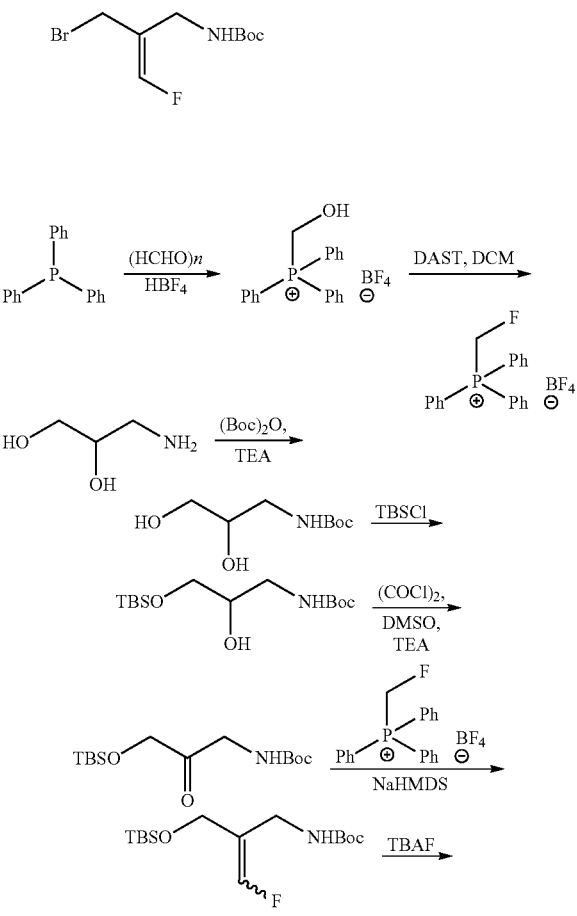

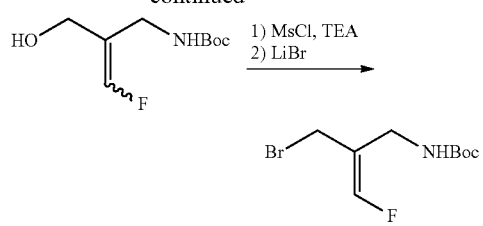

Step 1: Synthesis of tert-butyl (2,3-dihydroxypropyl)carbamate

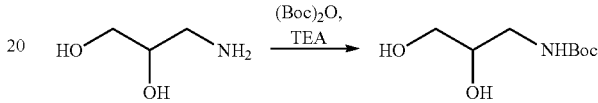

3-aminopropane-1,2-diol (30 g, 0.33 mol, 1.0 eq) was dissolved in methanol (600 mL), and triethylamine (69 mL, 0.51 mol, 1.5 eq) and di-tert-butyl dicarbonate (79.2 g, 0.36 mol, 1.1 eq) were added successively to react at room temperature for 5 hours. After the completion of the reaction indicated by ¹H-NMR detection, the reaction was concentrated to obtain a crude product (63 g, crude) as a pale yellow oil, which was used in the next step without purification.

¹H-NMR (300 MHz, CDCl₃) δ ppm: 1.41 (s, 9H), 3.33-3.18 (m, 4H), 3.68-3.48 (m, 2H), 3.82-3.69 (m, 1H), 4.10 (brs, 2H), 5.41 (br, 1H).

Step 2: Synthesis of tert-butyl (3-((tert-butyldimethylsilyl)oxy)-2-hydroxypropyl)carbamate

Tert-butyl (2,3-dihydroxypropyl)carbamate (63 g crude) was dissolved in dichloromethane (600 mL). The mixture was cooled to 0° C. Imidazole (33.6 g, 0.50 mol, 15 eq) and TBSCl (47.2 g, 0.315, 0.95 eq) were added successively. The temperature was maintained at 0° C. and the reaction was performed for 2 hours. After the completion of the reaction indicated by ¹H-NMR detection, water (500 mL) and dichloromethane (500 mL) were added. The liquid separation was performed. The organic phase was dried over anhydrous sodium sulfate and concentrated to obtain a crude product, which was purified by silica gel column chromatography (100-200 mesh silica gel, petroleum ether/ethyl acetate=0-10%) to obtain a colorless oil (78 g, yield: 78%).

¹H-NMR (400 MHz, CDCl₃) δ ppm: 0.07 (s, 6H), 0.90 (s, 9H), 1.44 (s, 9H), 2.48 (brs, 1H), 3.12 (ddd, J=14.1, 6.7, 5.3 Hz, 1H), 3.30-3.43 (m, 1H), 3.54 (dd, J=10.1, 6.2 Hz, 1H), 3.66 (dd, J=10.1, 4.5 Hz, 1H), 3.70-3.76 (m, 1H), 5.00 (brs, 1H).

Step 3: Synthesis of tert-butyl (3-((tert-butyldimethylsilyl)oxy)-2-oxopropyl)carbamate

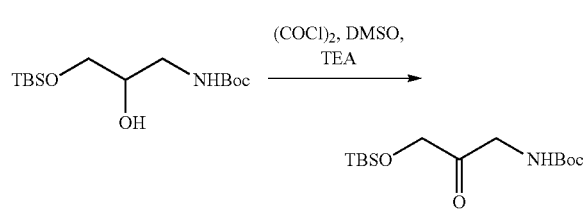

Under the nitrogen protection, oxalyl chloride (18.5 mL, 0.21 mmol, 1.5 eq) was dissolved in dichloromethane (250 mL). The temperature was reduced to −78° C. DMSO (21 mL, 0.28 mol, 2.0 eq) was added dropwise. After the completion of the dropwise addition, the temperature was maintained for 1 hour. Tert-butyl (3-((tert-butyldimethylsilyl)oxy)-2-hydroxypropyl)carbamate (44 g, 0.14 mol, 1.0 eq) was dissolved in dichloromethane (50 mL), and the resulting mixture was slowly added dropwise to the reaction system. After the completion of the dropwise addition, the temperature was maintained for 1 hour. Triethylamine (81 mL, 0.56 mmol, 4.0 eq) was added dropwise. After the completion of the dropwise addition, the temperature was slowly raised to room temperature. After the completion of the reaction indicated by TLC detection, water (400 mL) was added. The liquid separation was performed. The aqueous phase was extracted three times with dichloromethane. The organic phases were combined, dried, and concentrated to obtain a crude product, which was purified by silica gel column chromatography (100-200 mesh silica gel, petroleum ether/ethyl acetate=0-10%) to obtain an oily viscous liquid (28 g, yield: 64%).

$^1$H-NMR (400 MHz, CDCl$_3$) δ ppm: 0.10 (s, 6H), 0.93 (s, 9H), 1.47 (s, 9H), 4.25 (m, 4H), 5.21 (brs, 1H).

LC-MS (m/z)=325.0 [M+Na$^+$].

Step 4: Synthesis of (hydroxymethyl)triphenylphosphonium tetrafluoroborate

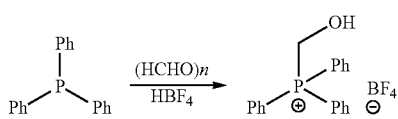

Triphenylphosphine (26.2 g, 01 mol, 1.0 eq) and paraformaldehyde (3 g, 0.1 mol, 1.0 eq) were dissolved in anhydrous diethyl ether (100 mL) at room temperature. The compound tetrafluoroboric acid (45 mL, 0.25 mol, 2.5 eq) was slowly added dropwise. The reaction was performed at room temperature for 5 days. After completion of the reaction indicated by $^1$H-NMR detection, the suction filtration was performed. The filter cake was washed with diethyl ether (100 mL), washed with cold water (100 mL) and dried to obtain a white solid (20 g, yield: 52%).

$^1$H-NMR (300 MHz; CDCl$_3$) δ ppm: 4.48 (brs, 1H), 5.36 (s, 2), 7.66-7.70 (m, 12H), 7.80-7.81 (m, 3H).

Step 5: Synthesis of (fluoromethyl)triphenylphosphonium tetrafluoroborate

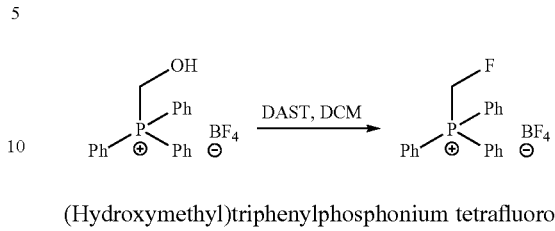

(Hydroxymethyl)triphenylphosphonium tetrafluoroborate (11.4 g, 0.03 mol, 1.0 eq) was dissolved in anhydrous dichloromethane (100 mL). The mixture was cooled to 0° C. DAST (7.2 mL, 0.06 mol, 2.0 eq) was slowly added dropwise. After the completion of the dropwise addition, the temperature was recovered to room temperature, and the reaction was performed for 1 hour. After the completion of the reaction indicated by TLC detection, the temperature was reduced to 0° C. Water (30 mL) was slowly added dropwise to quench the reaction. The liquid separation was performed. The organic phase was dried and concentrated to obtain a crude product, which was purified by silica gel column chromatography (100-200 mesh silica gel, methanol/dichloromethane=0-10%) to obtain another crude product, which was recrystallized with diethyl ether/dichloromethane to obtain a brown solid (5.0 g, yield: 44%).

$^1$H-NMR (300 MHz, CDCl$_3$) δ ppm: 6.30 (d, J=45 Hz, 2H), 7.72-7.76 (m, 12H), 7.85-7.87 (m, 3H).

Step 6: Synthesis of tert-butyl (2-(((tert-butyldimethylsilyl)oxy)methyl)-3-fluoroallyl)carbamate

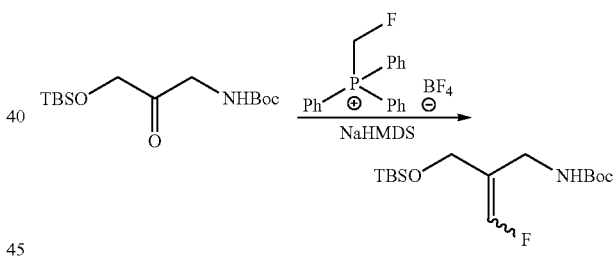

Under the nitrogen protection, (fluoromethyl)triphenylphosphonium tetrafluoroborate (5.0 g, 13.1 mmol, 1.5 eq) was dissolved in anhydrous THF (50 mL). The temperature was reduced to −20° C. NaHMDS (16M, 6.5 mL, 10.45 mmol, 1.5 eq) was slowly added dropwise. After the dropwise addition, the temperature was maintained for 10 minutes. A solution of tert-butyl (3-((tert-butyldimethylsilyl)oxy)-2-oxopropyl)carbamate (2.64 g, 8.7 mmol, 1.0 eq) in THF (5 mL) was slowly added dropwise. After the completion of the dropwise addition, the temperature was maintained for 1 hour. The temperature was recovered to room temperature. After the completion of the reaction indicated by LC-MS detection, water (10 mL) was added dropwise to quench the reaction. The reaction liquid was concentrated to a viscous liquid. Water (50 mL) was added. The mixture was extracted with diethyl ether (50 mL) for three times. The organic phases were combined, dried, and concentrated to obtain a crude product, which was purified by silica gel column chromatography (100-200-mesh silica gel, petroleum ether/ethyl acetate=0-30%) to obtain a colorless viscous liquid (cis-trans isomer mixture, 4.0 g, 97%).

¹H-NMR (300 MHz; CDCl₃) δ ppm: 0.093 (s, 6H), 0.91 (s, 9H), 1.47 (s, 9H), 3.89-3.70 (m, 2H), 4.34-4.09 (m, 2H), 5.15-4.97 (brs, 1H), 6.74-6.44 (m, 1H).

Step 7: Synthesis of tert-butyl (3-fluoro-2-(hydroxymethyl)allyl)carbamate

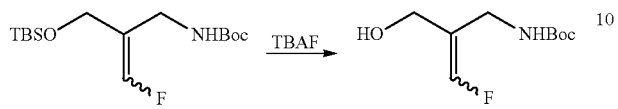

Tert-butyl (2-(((tert-butyldimethylsilyl)oxy)methyl)-3-fluoroallyl)carbamate (2.3 g, 7.2 mmol, 1.0 eq) was dissolved in anhydrous THF (30 mL) at room temperature. TBAF (2.83 g, 10.8 mmol, 1.5 eq) was added. The reaction was performed at room temperature for 2 hours. After the completion of the reaction indicated by LC-MS detection, water (50 mL) was added. The mixture was extracted with ethyl acetate (50 mL×3). The organic phases were combined, washed with a saturated saline solution, dried, and concentrated to obtain a crude product, which was purified by silica gel column chromatography (100-200 silica gel, petroleum ether/ethyl acetate=0-40%) to obtain an anhydrous oily liquid (cis-trans isomer mixture, 1.1 g, yield: 74%).

¹H-NMR (Z) (300 MHz; CDCl₃) δ ppm: 1.45 (s, 9H), 3.41 (br, 1H), 3.74 (dd, J=6.5, 3.1 Hz, 2H), 4.28 (dd, J=6.0, 2.3 Hz, 2H), 4.98 (br, 1H), 6.52 (d, J=83.4 Hz, 1H).

(E) (300 MHz; CDCl₃) δ ppm: 1.45 (s, 9H), 3.78 (t, J=6.4 Hz, 1H), 3.93-4.02 (m, 1H), 4.98 (br, 1H), 6.61 (d, J=83.7 Hz, 1H).

Step 8: Synthesis of (E)-tert-butyl (2-(bromomethyl)-3-fluoroallyl)carbamate

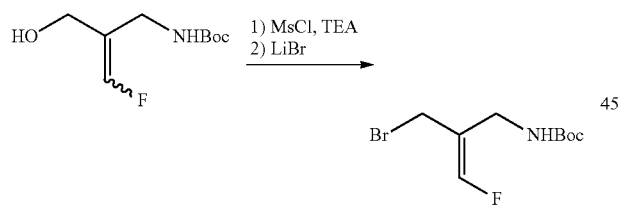

Under the nitrogen protection, tert-butyl (3-fluoro-2-(hydroxymethyl)allyl)c arbamate (1.2 g, 5.85 mmol, 1.0 eq) was dissolved in acetone (20 mL). The temperature was reduced to 0° C. Triethylamine (1.22 mL, 8.77 mmol, 1.5 eq) and methanesulfonyl chloride (0.54 mL, 7.07 mmol, 1.2 eq) were added successively. The temperature was maintained for 30 minutes. Suction filtration was performed. The filter cake was washed with acetone (10 mL). The filtrates were combined. Lithium bromide (2.54 g, 29.2 mmol, 5.0 eq) was added to the filtrate. The reaction was performed at room temperature for 1 hour. After the completion of the reaction indicated by LC-MS detection, water (25 mL) was added. The mixture was extracted with ethyl acetate (30 mL×2). The organic phases were combined, dried, and concentrated to obtain a crude product, which was purified by preparative HPLC (C18 column. H₂O:CH₃CN=55:45) to obtain a white solid (130 mg).

¹H-NMR (Z) (300 MHz; CDCl₃) δ ppm: 1.47 (s, 9H), 4.03-3.97 (m, 4H), 4.78 (br, 1H), 6.79 (d, J=80.8 Hz, 1H). LC-MS (m/z)=291.9 [M+Na]+.

Example 2: Synthesis of Intermediate (E)-tert-butyl (3-fluoro-2-(((1-oxo-1,2,3,4-tetrahydroisoquinolin-6-yl)oxy)methyl)allyl)carbamate

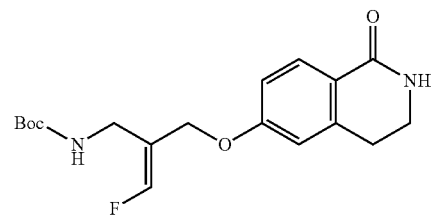 [SMILES: CC(C)(C)OC(=O)NC/C(=C\F)COc1ccc2c(c1)CCNC2=O]

Flow chart:

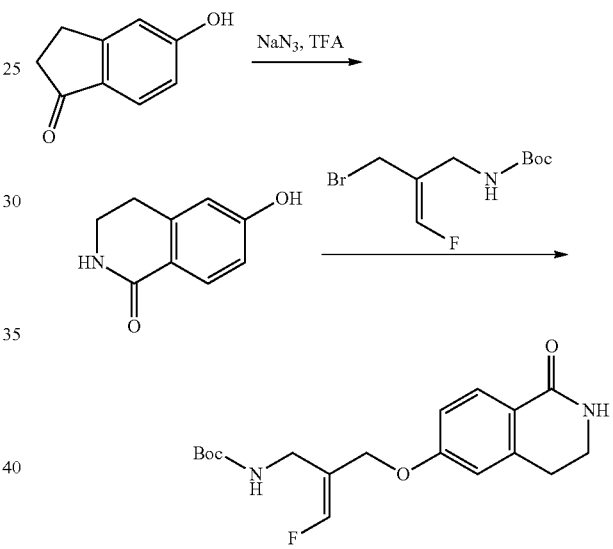

Step 1: Synthesis of Intermediate 6-hydroxy-3,4-dihydroisoquinolin-1(2H)-one

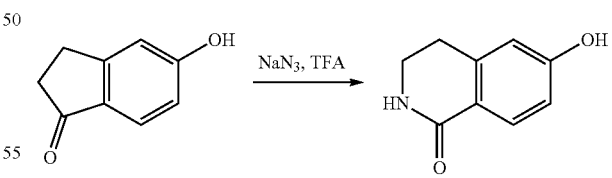

5-hydroxy-2,3-dihydro-1H-inden-1-one (2.5 g, 16.87 mmol) was dissolved in trifluoroacetic acid (0 mL). Sodium azide (1.65 g, 25.31 mmol) was added. The reaction liquid was stirred under reflux for 2 hours and then cooled to room temperature. The mixture was concentrated under reduced pressure. A saturated sodium bicarbonate solution (30 mL) was added. The resulting mixture was extracted with ethyl acetate (3×50 mL). The organic phases were combined, dried over anhydrous sodium sulfate, and concentrated under a reduced pressure. The resulting residue was purified by silica gel column chromatography (DCM:MeOH=50:1) to obtain 6-hydroxy-3,4-dihydroisoquinolin-1(2H)-one (0.7 g, 25.4%) as a pale yellow solid.

Step 2: Synthesis of (E)-tert-butyl (3-fluoro-2-(((1-oxo-1,2,3,4-tetrahydroisoquinolin-6-yl)oxy)methyl)allyl)carbamate

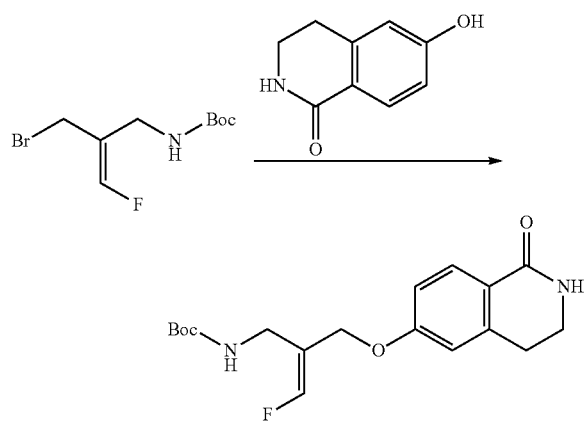

Intermediate (E)-tert-butyl (2-(bromomethyl)-3-fluoroallyl)carbamate (206.0 mg, 0.768 mmol, 1.0 eq) was dissolved in DMF (3 mL). 6-hydroxy-3,4-dihydroisoquinolin-1(2H)-one (150.5 mg, 0.922 mmol, 1.2 eq) and K₂CO₃ (159.2 mg, 0.152 mmol, 1.5 eq) were added. the reaction was performed under being stirred at room temperature under the nitrogen protection for 10 hours. After the completion of the reaction, a saturated aqueous ammonium chloride solution (30 mL) was added. The mixture was extracted with ethyl acetate (3×30 mL). The organic phases were combined, dried over anhydrous sodium sulfate, filtered, and concentrated to obtain a crude product, which was purified by silica gel column chromatography (DCM:MeOH=100:1 to 20:1) to obtain (T)-tert-butyl (3-fluoro-2-(((1-oxo-1,2,3,4-tetrahydroisoquinolin-6-yl)oxy)methyl)allyl)carbamate as a white solid (219.6 mg, yield: 77%).

Example 3: Synthesis of Intermediate 2-cyclopropyl-6-hydroxy-3,4-dihydroisoquinolin-1(2H)-one

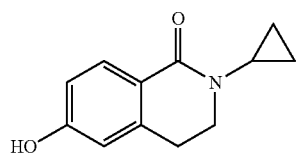 [SMILES: O=C1c2ccc(O)cc2CCN1C1CC1]

Flow chart:

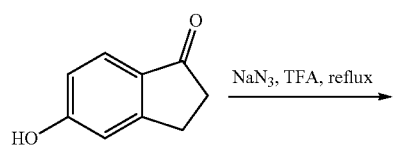

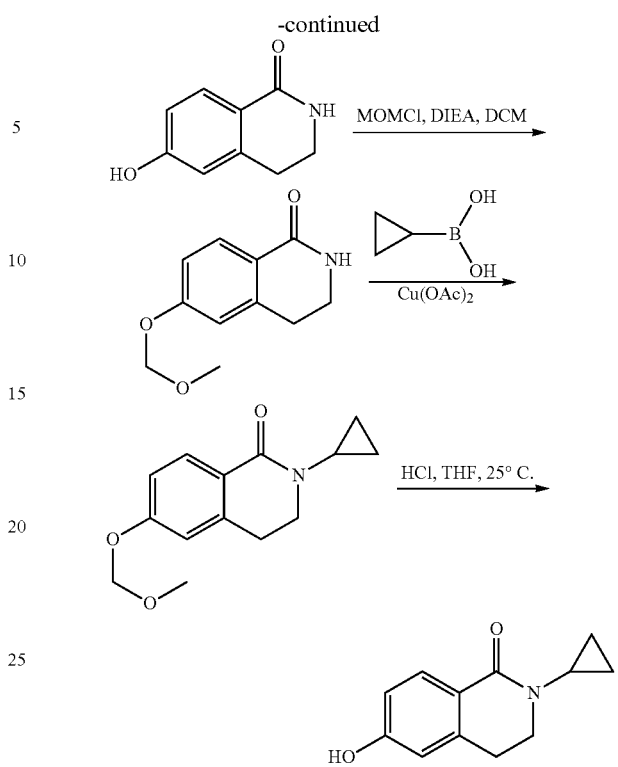

Step 1: Synthesis of 6-hydroxy-3,4-dihydroisoquinolin-1(2H)-one

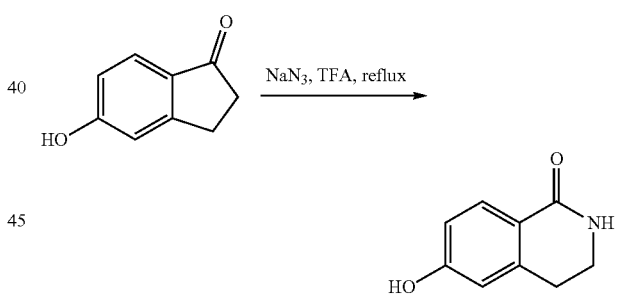

5-hydroxy-2,3-dihydro-1-inden-1-one (10 g, 67.50 mmol, 1.0 eq) was added to trifluoroacetic acid (80 mL). Sodium azide (6.6 g, 101.5 mmol, 1.5 eq) was added in batchs with the temperature being controlled below 25° C. After the completion of the addition, the mixture was reacted under reflux for 6 hours. HPLC detection showed that the raw material was not completely reacted. The temperature was reduced to 25° C. Sodium azide (6.6 g, 101.5 mmol, 1.5 eq) was supplemented. The mixture was reacted under reflux overnight. After the completion of the reaction indicated by TLC detection, the reaction was cooled to room temperature, poured into ice water (300 mL), adjusted to a pH of 6-7 with saturated sodium bicarbonate, and extracted with a mixed solvent of DCM and MeOH (10:1) (100 mL×3). The organic phases were dried and concentrated to obtain a crude product, which was purified by silica gel column chromatography (EA) to obtain a product (7.1 g, yield: 64.5%).

Step 2: Synthesis of 6-(methoxymethoxy)-3,4-dihydroisoquinolin-1(2H)-one

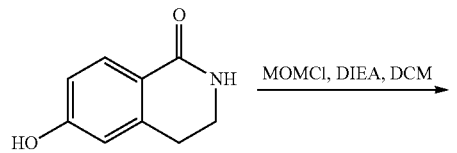

6-hydroxy-3,4-dihydroisoquinolin-1(2H)-one (6 g, 36.77 mmol, 1.0 eq) was added to DCM (120 mL). DIEA (9.5 g, 73.50 mmol, 2.0 eq) was added. The mixture was cooled to 0° C. A solution of MOMCl (3.55 g, 44.09 mmol, 1.2 eq) in DCM (36 mL) was slowly added dropwise. After the completion of the dropwise addition, the reaction was performed at 25° C. overnight. After the completion of the reaction indicated by TLC and LC-MS detection, water (100 mL) was added. The liquid separation was performed. The aqueous phase was extracted with a mixed solvent of DCM and MeOH (10:1) (50 mL×5). The organic phase was dried, concentrated to obtain a crude product, which was purified by silica gel column chromatography (PE:EA=1:1 to EA) to obtain a product (4.8 g, yield: 63%).

Step 3: Synthesis of 3-cyclopropyl-6-(methoxymethoxy)-3,4-dihydroisoquinolin-1(2)-one

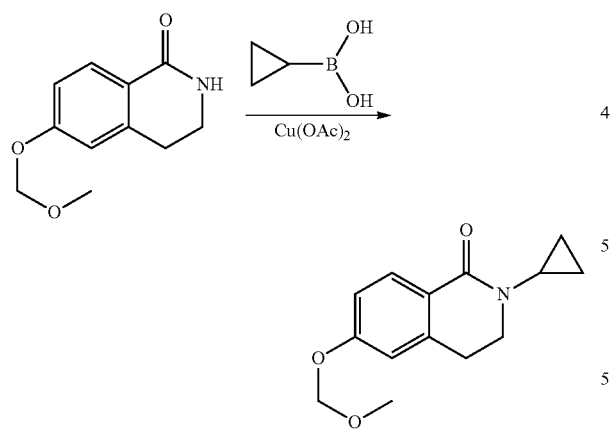

6-(methoxymethoxy)-3,4-dihydroisoquinolin-1(2H)-one (3.36 g, 16.21 mmol, 1.0 eq), sodium carbonate (2.59 g, 24.32 mmol, 1.5 eq), copper acetate (4.86 g, 24.32 mmol, 1.5 eq) and cyclopropylboric acid (2.79 g, 32.42 mmol, 2.0 eq) were added to toluene (135 mL). The substitution of oxygen was performed, the temperature was raised to 80° C., and the reaction was performed overnight. LC-MS and HPLC detections showed that 33% of the raw material remained. The temperature was reduced to 25° C. Suction filtration was performed. The filter cake was washed with DCM (50 mL×3). The filtrate was concentrated to obtain a crude product, which was purified by silica gel column chromatography (PE:EA=1:1 to EA) to obtain a product (2.48 g, yield: 62%).

Step 4: Synthesis of 2-cyclopropyl-6-hydroxy-3,4-dihydroisoquinolin-1(2H)-one

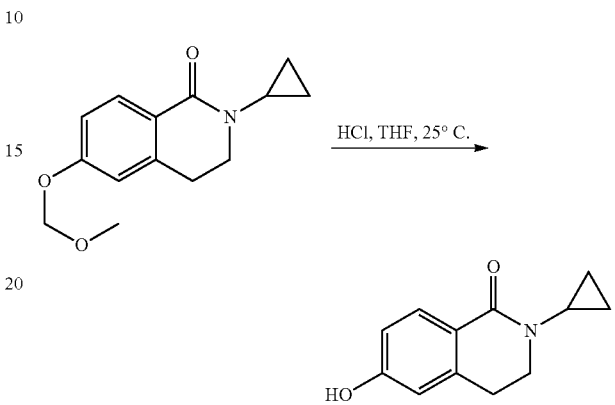

3-cyclopropyl-6-(methoxymethoxy)-3,4-dihydroisoquinolin-1 (2H)-one (2.48 g 10.03 mmol) was added to tetrahydrofuran (24.8 mL). 6 mol/L hydrochloric acid (24.8 mL, 149 mmol, 14.85 eq) was added. The reaction was performed under being stirred at 30° C. for 2 hours. After the completion of the reaction indicated by TLC and LC-MS detections, the reaction was poured into ice water (20 mL). The mixture was adjusted to a pH of 3-4 with saturated sodium bicarbonate, and extracted with ethyl acetate (30 mL×3). The organic phases were combined, washed with a saturated saline solution (50 mL×3), dried, and concentrated to obtain a product (1.85 g, yield: 70%).

$^1$H NMR (400 MHz, DMSO-$d_6$) δ(ppm): 10.05 (s, 1H), 7.76 (d, J=8.8 Hz, 1H), 6.76-6.73 (m, 1H), 6.64 (d, J=2.1 Hz, 1H), 3.46 (t, J=6.5 Hz, 2H), 2.93-2.76 (m, 3H), 0.80-0.79 (m, 2H) 0.69-0.67 (m, 2H).

Molecular formula: $C_2H_3NO_2$ Molecular weight: 203.2 LC-MS (Pos, m/z)=204.2 [M+H]$^+$.

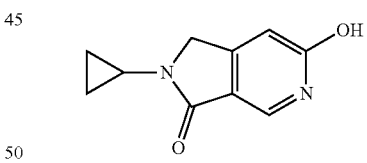

Flow chart:

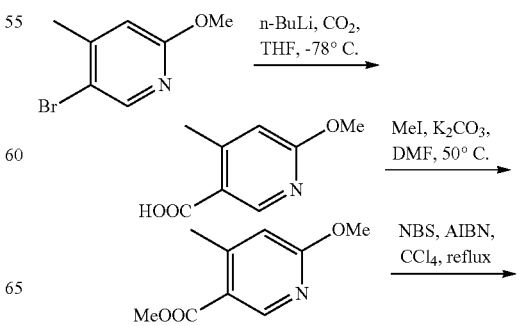

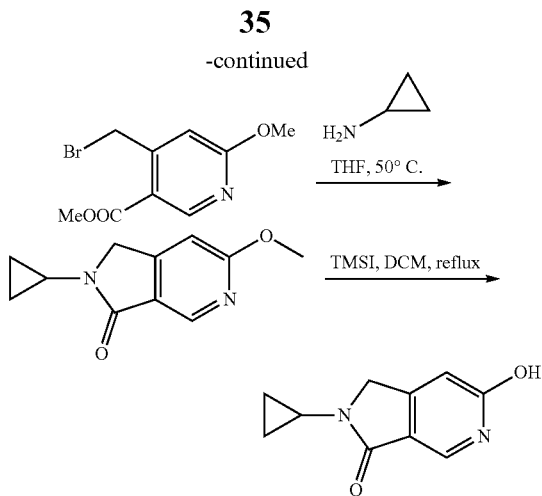

Step 1: Synthesis of Intermediate 6-methoxy-4-methylnicotinic acid

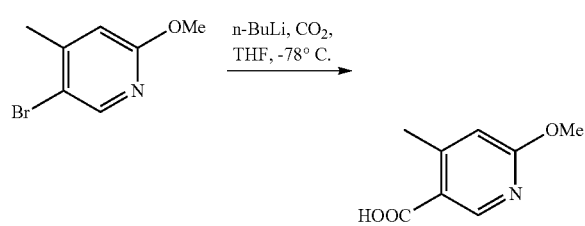

Under the nitrogen protection, 5-bromo-2-methoxy-4-methylpyridine (10 g, 49.5 mmol, 1.0 eq) was dissolved in anhydrous TH (170 mL). The temperature was reduced to −78° C. A solution of n-butyllithium in T-IF (2.4 mol/L) was slowly added dropwise. After the completion of the dropwise addition, the temperature was maintained for 10 minutes. A carbon dioxide gas was introduced until the system became bright yellow. The reaction was continued for 1 hour at −78° C. 1 mol/L of hydrochloric acid solution (25 mL) was slowly added dropwise. After the completion of the dropwise addition, the temperature was slowly recovered to room temperature. After the completion of the reaction indicated by LC-MS detection, the reaction was adjusted with 6 mol/L of hydrochloric acid solution to a pH value of 3. The system was concentrated under a reduced pressure. Most of organic solvent was removed. A solid was separated out. Suction filtration was performed. The filter cake was washed with water (100 mL×2), and dried. The filtrate was extracted with DCM (50 mL×3). The organic phases were combined, dried and concentrated to obtain a product (6.5 g, crude product), which was directly used for the next reaction without purification.

Step 2: Synthesis of Intermediate methyl 6-methoxy-4-methylnicotinate

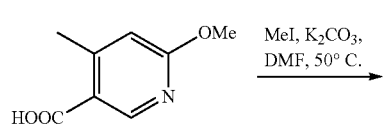

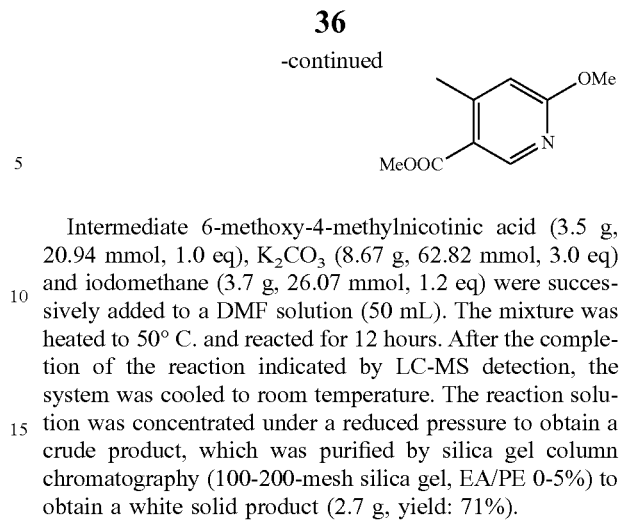

Intermediate 6-methoxy-4-methylnicotinic acid (3.5 g, 20.94 mmol, 1.0 eq), $K_2CO_3$ (8.67 g, 62.82 mmol, 3.0 eq) and iodomethane (3.7 g, 26.07 mmol, 1.2 eq) were successively added to a DMF solution (50 mL). The mixture was heated to 50° C. and reacted for 12 hours. After the completion of the reaction indicated by LC-MS detection, the system was cooled to room temperature. The reaction solution was concentrated under a reduced pressure to obtain a crude product, which was purified by silica gel column chromatography (100-200-mesh silica gel, EA/PE 0-5%) to obtain a white solid product (2.7 g, yield: 71%).

Step 3: Synthesis of Intermediate methyl 4-(bromomethyl)-6-methoxy nicotinate

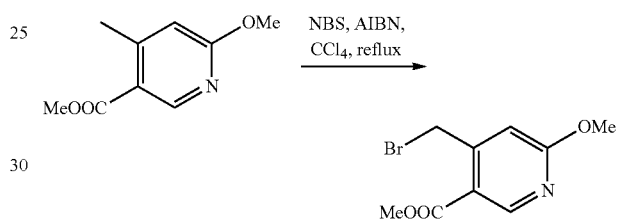

Intermediate methyl 6-methoxy-4-methylnicotinate (2.7 g, 15.0 mmol, 1.0 eq), NBS (2.67 g, 15.0 mmol, 1.0 eq) and azobisisobutyronitrile (120 mg, 0.7 mmol, 0.05 eq) were added to $CCl_4$ (30 mL). The mixture was heated and reacted under reflux for 2 hours. After LC-MS detection showed the reaction was completed, the reaction system was cooled to room temperature. The reaction liquid was concentrated under a reduced pressure. EA (30 ml) was added to the reaction mixture. Suction filtration was performed. The filtrate was concentrated to give a crude product, which was purified by silica gel column chromatography (100-200-mesh silica gel, EA/PE=0-5%) to obtain a yellow oily product (3.0 g of crude product), which was directly used for the next reaction.

Step 4: Synthesis of Intermediate 2-cyclopropyl-6-methoxy-1,2-dihydro-3H-pyrrolo-[3,4-c]pyridin-3-one

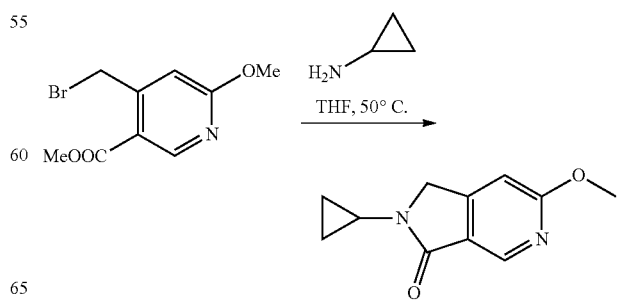

Intermediate methyl 4-(bromomethyl)-6-methoxy nicotinate (3.0 g, crude) was dissolved in TH (30 mL). Cyclopropylamine (1.98 g, 34.61 mmol, 3.0 eq) was added. The reaction mixture was heated to 50° C. in a sealed tube and reacted for 15 hours. After the completion of the reaction indicated by LC-MS detection, the temperature was reduced to room temperature. The reaction liquid was concentrated under a reduced pressure to obtain a crude product, which was purified by silica gel column chromatography (100-200 mesh silica gel, EA/PE=0-40%) to obtain a product (1.25 g, two-step yield: 40%).

Step 5: Synthesis of Intermediate 2-cyclopropyl-6-hydroxy-1,2-dihydro-3H-pyrrolo-[3,4-c]pyridin-3-one

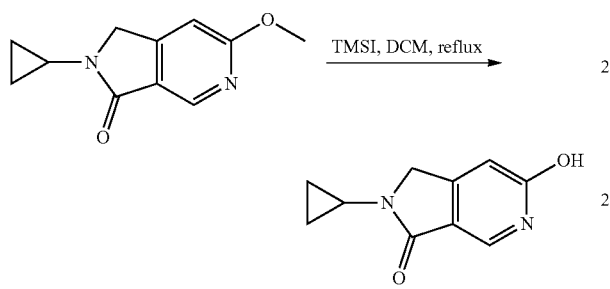

Under the nitrogen protection, 2-cyclopropyl-6-methoxy-1,2-dihydro-3H-pyrrolo-[3,4-c]pyridin-3-one (1.2 g, 5.87 mmol, 1.0 eq) and iodotrimethylsilane (3.5 g, 17.61 mmol, 3.0 eq) were added to DCM. The mixture was heated and reacted under reflux for 12 hours. After the completion of the reaction indicated by LC-MS detection, the temperature was reduced to room temperature. The reaction liquid was concentrated under a reduced pressure. A mixed solution of 10% methanol and dichloromethane (20 mL) was added, and a black insoluble solid was separated out. Suction filtration was performed. The filtrate was concentrated to obtain a crude product, which was purified by silica gel column chromatography (300-400 mesh silica gel, 0-5% MeOH/DCM) to obtain 1.05 g of impure product, and then purified by preparative thin layer chromatography to obtain a white solid product (485 mg, yield: 43%).

¹H NMR (400 MHz, DMSO-d) δ(ppm): 12.01 (brs, 1H), 7.83 (s, 1H), 6.35 (s, 1H), 4.28 (s, 2H), 2.81-2.76 (m, 1H), 0.77-0.71 (m, 4H).

Molecular formula: $C_{10}H_{10}N_2O_2$ Molecular weight: 190.2 LC-MS (Pos, m/z)=191.1 [M+H]⁺

Example 5: Synthesis of (E)-6-((2-(aminomethyl)-3-fluoroallyl)oxy)-2-isopropyl-3,4-dihydroisoquinolin-1(2H)-one (compound 4) trifluoroacetate

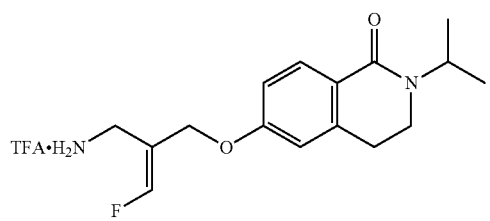

Flow chart:

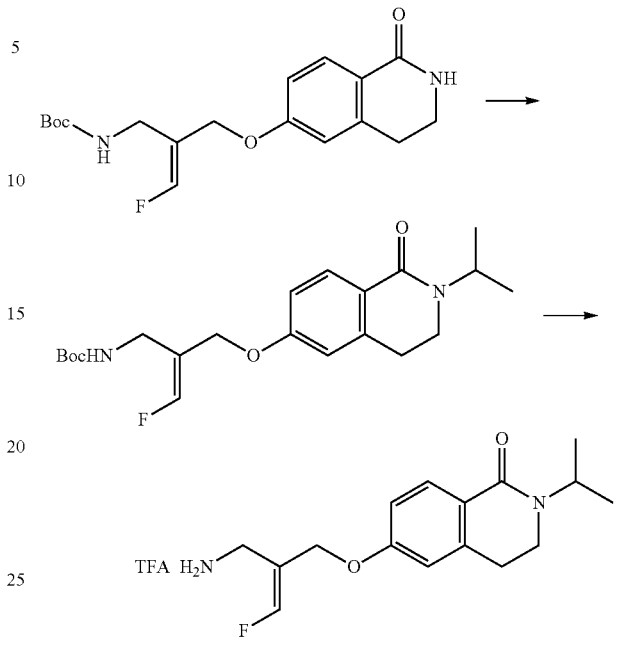

Step 1: Synthesis of (E)-tert-butyl (3-fluoro-2-(((2-isopropyl-1-oxo-1,2,3,4-tetrahydroisoquinolin-6-yl)oxy)methyl)allyl)carbamate

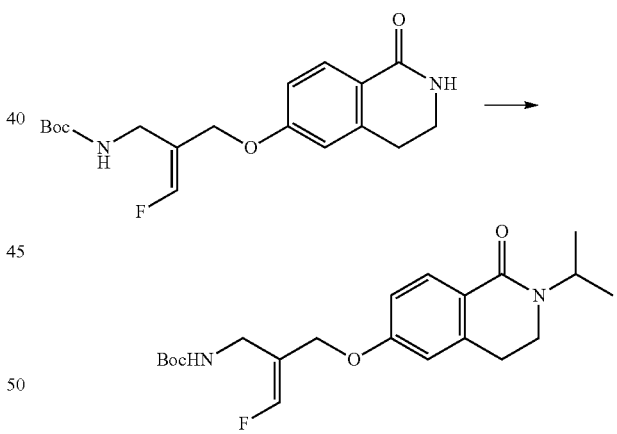

Intermediate (E)-tert-butyl (3-fluoro-2-(((1-oxo-1,2,3,4-tetrahydroisoquinolin-6-yl)oxy)methyl)allyl)carbamate (50.0 mg, 0.143 mmol, 1.0 eq) was dissolved in DMF (3 mL). The temperature was reduced to 0° C. NaH (11.4 mg, 0.286 mmol, 2.0 eq) was added. The reaction was performed under being stirred for 30 minutes. Iodoisopropane (36.4 mg. 0.214 mmol, 1.5 eq) was added. The reaction was performed at 70° C. for 2 hours. After the completion of the reaction indicated by LC-MS detection, the system was cooled to room temperature. Water (10 mL) was added. The mixture was extracted with ethyl acetate (3×10 mL), and dried with anhydrous sodium sulfate. Suction filtration was performed. The filtrate was concentrated to obtain a crude product, which was purified by preparative thin layer chromatography (PE:EA=1:1) to obtain a colorless oily substance (E)-tert-butyl (3-fluoro-2-(((2-isopropyl-1-oxo-1,2,3,4-tetrahydroisoquinolin-6-yl)oxy)methyl)allyl)carbamate (13.7 mg, yield: 24%).

Step 2: Synthesis of (E)-6-((2-(aminomethyl)-3-fluoroallyl)oxy)-2-isopropyl-3,4-dihydroisoquinolin-1(2H)-one trifluoroacetate

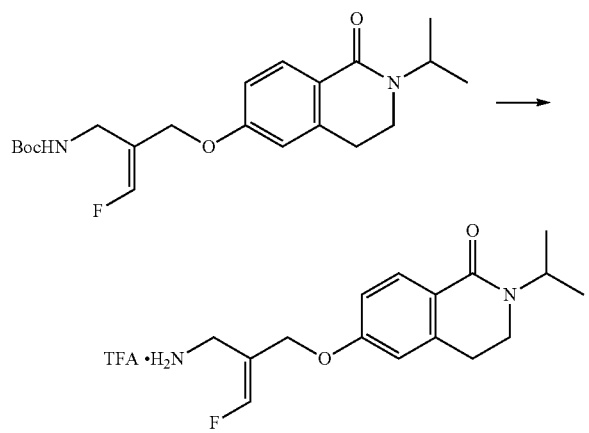

Intermediate (E)-tert-butyl (3-fluoro-2-(((2-isopropyl-1-oxo-1,2,3,4-tetrahydroisoquinolin-6-yl)oxy)methyl)allyl) carbamate (13.7 mg, 0.035 mmol, 1.0 eq) was dissolved in 1,4-dioxane (3 mL). Hydrogen chloride dioxane solution (5 mL) was added. The reaction was performed under being stirred at 30° C. for 2 hours. After the completion of the reaction indicated by LC-MS detection, the solution was directly concentrated to give a crude product, which was purified by preparative liquid chromatography (MeCN:H₂O (0.05% trifluoroacetic acid water)=1:5) to obtain (E)-6-((2-(aminomethyl)-3-fluoroallyl)oxy)-2-isopropyl-3,4-dihydroisoquinolin-1(2H)-one trifluoroacetate as a white solid (5 mg, yield: 35%).

$^1$H NMR (400 MHz, CD$_3$OD) δ(ppm): 7.88-7.92 (d, 1H), 7.12-7.35 (d, 1H, J=92 Hz), 4.75 (m, 3H), 4.63-4.69 (m, 2H), 3.90 (m, 2H), 3.83 (m, 2H), 3.50-3.66 (m, 3H), 2.95-2.98 (m, 2H), 1.23-1.25 (n, 6H).

Molecular formula: $C_{16}H_{21}FN_2O_2$ Molecular weight: 292.35 LC-MS (m/z)=293.16 [M+H]$^+$.

Example 6: Synthesis of (E)-6-((2-(aminomethyl)-3-fluoroallyl)oxy)-2-cyclopropyl-3,4-dihydroisoquinolin-1(2H)-one (Compound 5) hydrochloride

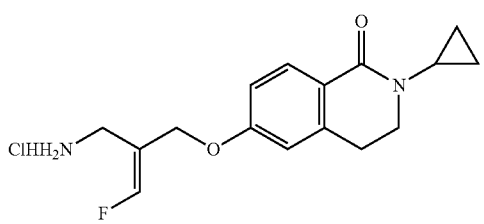

Flow chart:

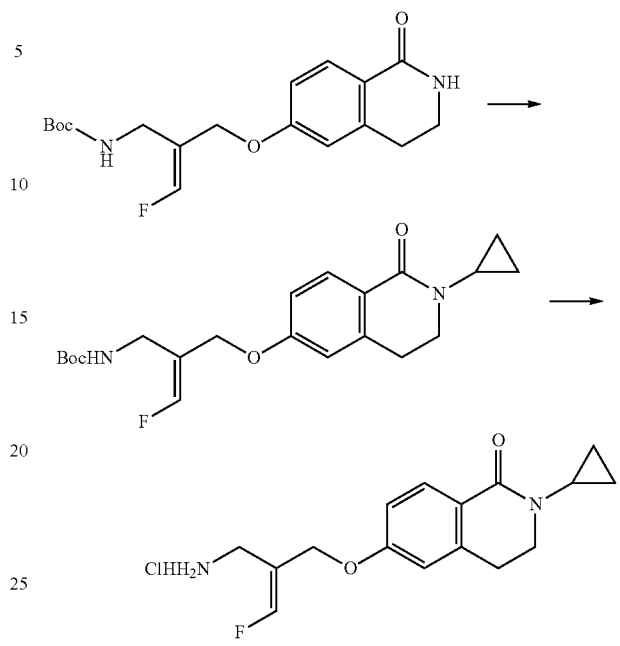

Step 1: Synthesis of (h)-tert-butyl (2-(((2-cyclopropyl-1-oxo-1,2,3,4-tetrahydroisoquinolin-6-yl)oxy)methyl)-3-fluoroallyl)carbamate

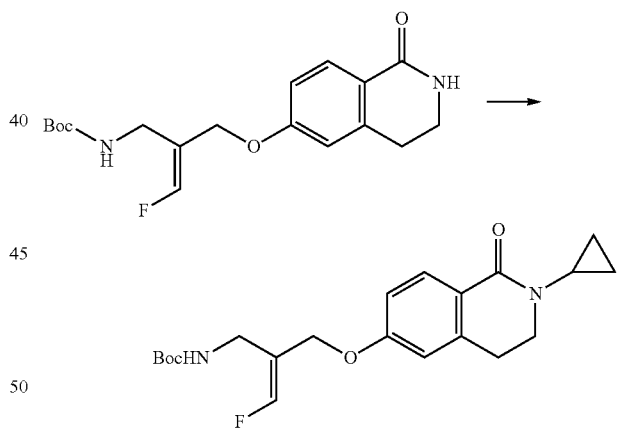

Intermediate (E)-tert-butyl (3-fluoro-2-(((1-oxo-1,2,3,4-tetrahydroisoquinolin-6-yl)oxy)methyl)allyl)carbamate (50 mg, 0.143 mmol, 1.0 eq) was dissolved in tetrahydrofuran (5 mL). Cyclopropyl boric acid (15.9 mg, 0.186 mmol, 1.3 eq), triethylamine (72.4 mg, 0.715 mmol, 5.0 eq), pyridine (90.5 mg, 1.144 mmol, 8.0 eq) and copper acetate (57.1 mg, 0.286 mmol, 2.0 eq) were added. The reaction was performed at 70° C. for 72 hours. After the completion of the reaction indicated by LC-MS detection, the reaction was cooled to room temperature. A saturated sodium bicarbonate solution (10 mL) was added. The mixture was extracted with ethyl acetate (3×15 mL), and dried over anhydrous sodium sulfate. Suction filtration was performed. The filtrate was concentrated to obtain a crude product, which was purified by preparative thin layer chromatography (PE:EA=1:1) to obtain a colorless oily product (E)-tert-butyl (2-(((2-cyclopropyl-1-oxo-1,2,3,4-tetahydroisoquinolin-6-yl)oxy)methyl)-3-fluoroallyl)carbamate (29.5 mg, yield: 53%).

Step 2: Synthesis of (E)-6-(2-(aminomethyl)-3-fluoroallyl)oxy)-2-cyclopropyl-3,4-dihydroisoquinolin-1(2H)-one hydrochloride

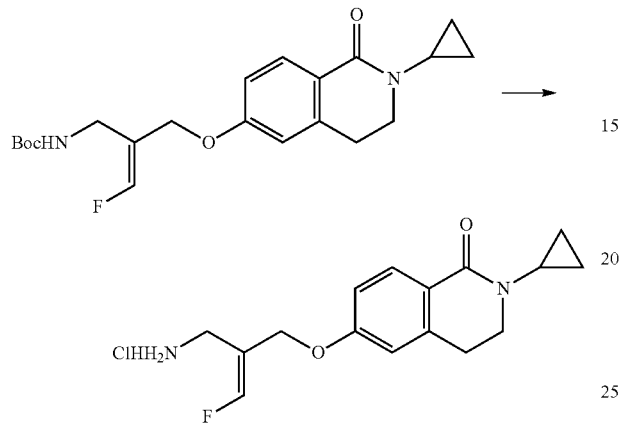

Intermediate (E)-tert-butyl (2-(((2-cyclopropyl-1-oxo-1,2,3,4-tetrahydroisoquinolin-6-yl)oxy)methyl)-3-fluoroallyl)carbamate (29.5 mg, 0.0756 mmol, 1.0 eq) was dissolved in ethanol (5 mL). Hydrogen chloride ethanol solution (8 mL) was added. The reaction was performed under being stirred for 3 hours. After the completion of the reaction indicated by LC-MS detection, the solution was directly concentrated to obtain a crude product, which was purified by reverse phase column chromatography (MeCN:H₂O (0.018% HCl)=1:4.5) to obtain a white solid (E)-6-((2-(aminomethyl)-3-fluoroallyl)oxy)-2-cyclopropyl-3,4-dihydroisoquinolin-1(2H)-one hydrochloride (12 mg, yield: 49%).

$^1$H NMR (400 MHz, DMSO-$d_6$) δ(ppm): 8.05 (m, 3H), 7.28-7.85 (d, 1H), 7.24-7.45 (d, 1H, J=81.8 Hz), 6.93-6.96 (m, 1H), 6.88-6.89 (m, 1H), 4.64 (m, 2H), 3.63 (m, 2H), 3.43-3.45 (d, 2H), 2.88-2.91 (m, 2H), 2.81 (m, 1H), 0.76-0.77 (m, 2H), 0.65-0.66 (m, 2H).

Molecular formula: $C_{16}H_{19}FN_2O_2$ Molecular weight: 290.34 LC-MS (n/z)=291.09 [M+H]$^+$.

Example 7: Synthesis of Intermediate 6-cyclopropyl-2-hydroxy-7,8-dihydro-1,6-naphthyridin-5(6H)-one

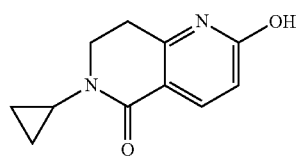 [SMILES: O=C1c2ccc(O)nc2CCN1C1CC1]

Flow chart:

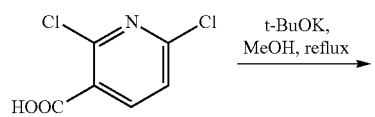

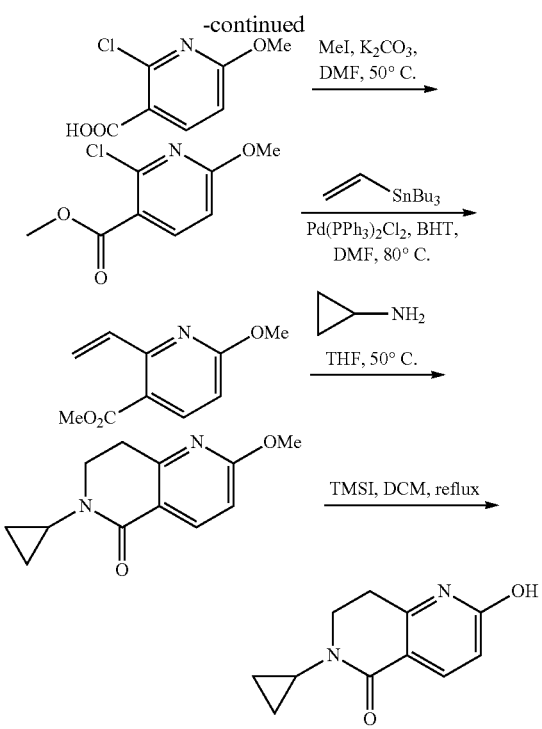

Step 1: Synthesis of Intermediate 2-chloro-6-methoxynicotinic acid

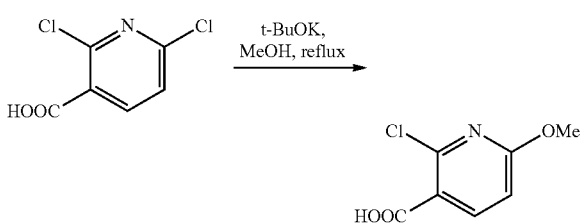

2,6-dichloronicotinic acid (10 g, 52.1 mmol, 1.0 eq) was dissolved in methanol (460 mL). Potassium tert-butoxide (23.37 g, 208.3 mmol, 4.0 eq) was added. The mixture was heated and reacted under reflux for 48 hours. After the completion of the reaction indicated by LC-MS detection, the temperature was reduced to room temperature. The reaction mixture was concentrated under reduced pressure. Water (150 mL) was added to the residue, and then an aqueous hydrochloric acid solution (6N) was slowly added dropwise. A large amount of white solid was separated out. Suction filtration was performed. The filter cake was washed by water (300 mL×3), and dried to obtain a white solid product (8.5 g, yield: 86%).

Step 2: Synthesis of Intermediate methyl 2-chloro-6-methoxynicotinate

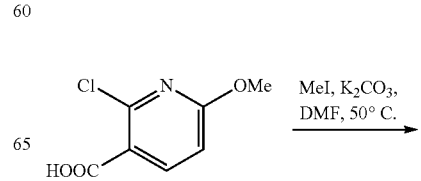

-continued

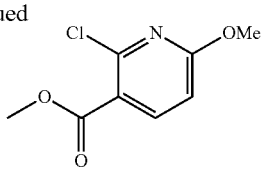

Intermediate 2-chloro-6-methoxynicotinic acid (3.0 g, 16.00 mmol, 1.0 eq), K₂CO₃ (2.48 g, 17.94 mmol, 1.1 eq) and iodomethane (3.07 g, 21.6 mmol, 1.4 eq) were added to a DMF solution (35 mL). The mixture was heated to 50° C. and reacted for 12 hours. After the completion of the reaction indicated by LC-MS detection, the temperature was reduced to room temperature. The reaction liquid was directly concentrated under reduced pressure to obtain a crude product, which was purified by silica gel column chromatography (100-200 mesh silica gel) to obtain a white solid product (1.5 g, yield: 47%).

Step 3: Synthesis of Intermediate methyl 6-methoxy-2-vinylnicotinate

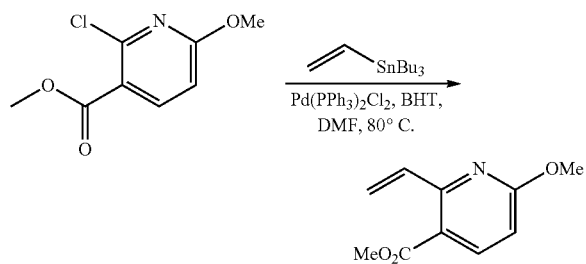

Under the nitrogen protection, Intermediate methyl 2-chloro-6-methoxynicotinate (4.0 g, 19.88 mmol, 1.0 eq), tributyl(vinyl)stannane (7.57 g, 23.86 mmol, 1.2 eq), 2,6-di-tert-butyl-4-methylphenol (219 mg, 0.99 mmol, 0.05 eq) and Pd(PPh₃)₂Cl₂ (700 mg, 0.99 mmol, 0.05 eq) were successively added to DMF (45 mL). The mixture was heated to 80° C. and reacted for 12 hours. LC-MS detection showed that there was a small amount of the raw material that was not completely reacted, and the system temperature was reduced to room temperature. The reaction liquid was concentrated under a reduced pressure to obtain a crude product, which was purified by silica gel column chromatography to obtain a yellow oily product (2.7 g, yield: 71%).

Step 4: Synthesis of Intermediate 6-cyclopropyl-2-methoxy-7,8-dihydro-1,6-naphthyridin-5(6H)-one

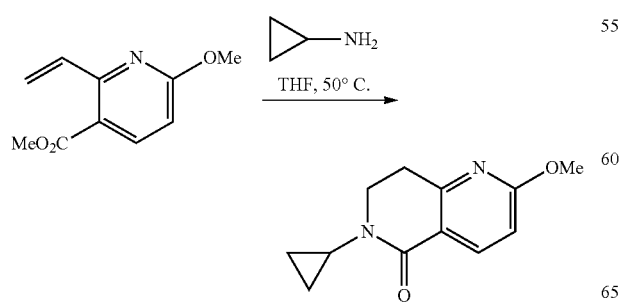

Intermediate methyl 6-methoxy-2-vinylnicoinate (2.5 g, 12.94 mmol, 1.0 eg) was added to cyclopropylamine (25 mL). The mixture was heated to 50° C. in a sealed tube and reacted for 6 hours. After the completion of the reaction indicated by LC-MS detection, the temperature was reduced to room temperature. The reaction liquid was concentrated under a reduced pressure to obtain a crude product, which was purified by silica gel column chromatography to obtain a white solid product (1.3 g, yield: 46%).

Step 5: Synthesis of Intermediate 6-cyclopropyl-2-hydroxy-7,8-dihydro-1,6-naphthyridin-5(6H)-one

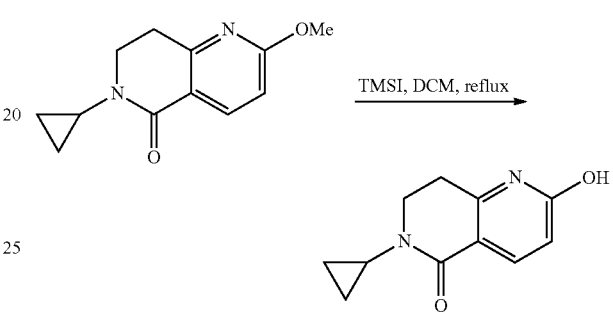

Under the nitrogen protection, Intermediate 6-cyclopropyl-2-methoxy-7,8-dihydro-1,6-naphthyridin-5(6H)-one (1.1 g, 5 mmol, 1.0 eq) and iodotrimethylsilane (3 g, 15 mmol, 3.0 eq) were added to DCM. The mixture was heated and reacted under reflux for 12 hours. LC-MS and HPLC detections showed that there was a small amount of the raw material that was not completely reacted. The system temperature was reduced to room temperature. The reaction liquid was concentrated under a reduced pressure. A mixed solution (20 mL) of 10% methanol and dichloromethane was added. Suction filtration was performed. The filtrate was concentrated to obtain a crude product, which was purified by silica gel column chromatography to obtain 890 mg of a further crude product, which was then purified by preparative thin layer chromatography to obtain a white-like solid product (450 mg, yield: 44%).

¹H NMR (400 MHz, MeOD-d4) δ(ppm): 7.97 (d, J=9.6 Hz, 1H), 6.40 (d, J=9.2 Hz, 1H), 3.63 (t, J=6.8 Hz, 2H), 2.92 (t, J=6.8 Hz, 2H), 2.72-2.70 (m, 1H), 0.88-0.86 (m, 2H), 0.72-0.70 (m, 2H).

Molecular formula: $C_{11}H_{12}N_2O_2$ Molecular weight: 204.23 LC-MS (Pos, m/z)=205.1 [M+H]⁺

Example 8 Synthesis of Intermediate 6-cyclopropyl-3-hydroxy-5,6-dihydro-7H-pyrrolo[3,4-b]pyridin-7-one

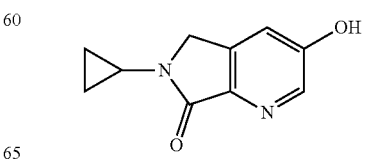

Flow chart:

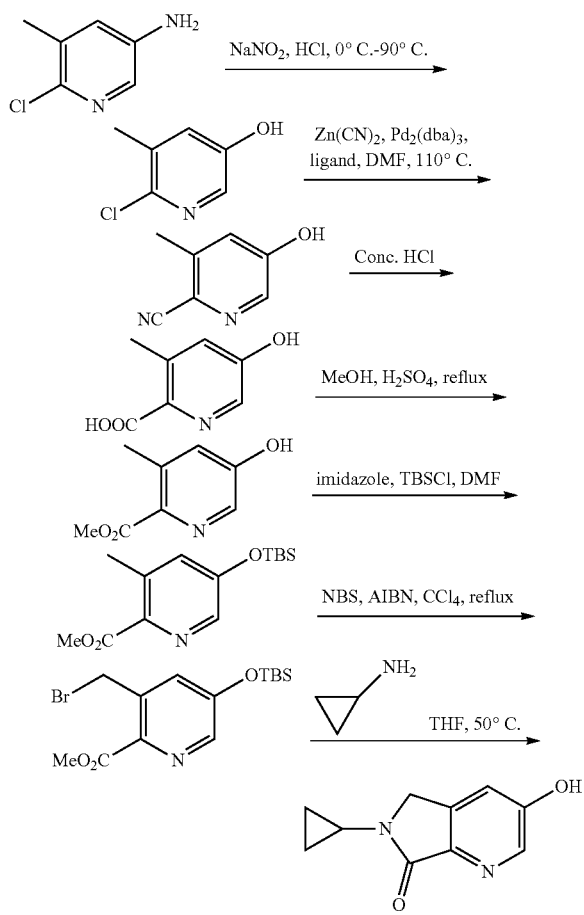

Step 1: Synthesis of 6-chloro-5-methylpyridin-3-ol

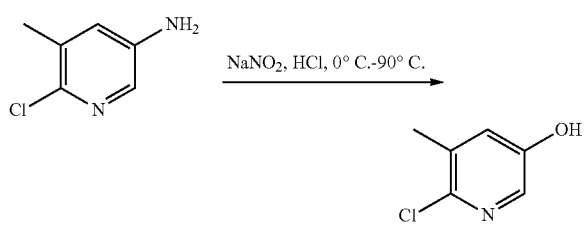

6-chloro-5-methylpyridin-3-amine (50 g, 0.352 mol, 1.0 eq) was dissolved in 6 mol/L hydrochloric acid solution (500 mL). The mixture was stirred for 30 minutes. The temperature was reduced to 0° C. A solution of sodium nitrite (29.1 g, 0.422 mol, 12 eq) in water (300 mL) was added dropwise. After the completion of the dropwise addition, the temperature was maintained for 20 minutes. The temperature was recovered to room temperature, and the mixture was stirred for 20 minutes. Then the mixture was heated to 90° C. and reacted 30 minutes. After the completion of the reaction indicated by LC-MS detection, the system temperature was reduced to room temperature. The mixture was extracted with EA (500 mL×5). The organic phases were combined, dried and concentrated to obtain a crude product, which was purified by silica gel column chromatography (100-200 mesh silica gel, PE:EA=15:1) to obtain a white solid product (17 g, yield: 34%).

Step 2: Synthesis of 5-hydroxy-3-methyl-2-cyanopyridine

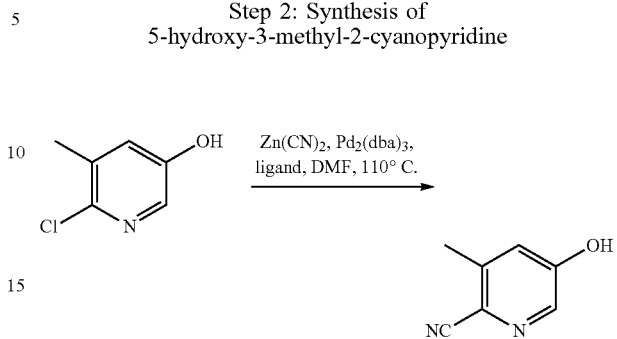

Under the nitrogen protection, 6-chloro-5-methylpyridin-3-ol (10.8 g, 75.2 mmol, 1.0 eq), zinc cyanide (10.6 g, 90.2 mmol, 1.2 eq), 2-dicyclohexylphosphine-2',6'-dimethoxybiphenyl (6.17 g, 15.0 mmol, 0.2 eq) and $Pd_2(dba)_3$ (6.87 g, 7.5 mmol, 0.1 eq) were successively added to DMF (200 mL). The mixture was heated to 110° C. and reacted for 12 hours. LC-MS detection showed that there were some raw materials that were not completely reacted. The system temperature was reduced to room temperature. Suction filtration was performed. The filtrate was concentrated under a reduced pressure to obtain a crude product, which was purified by silica gel column chromatography (100-200 mesh silica gel, EA:PE=0-50%) to obtain a white solid product (3.1 g, yield: 31%).

Step 3: Synthesis of 5-hydroxy-3-methylpicolinic acid

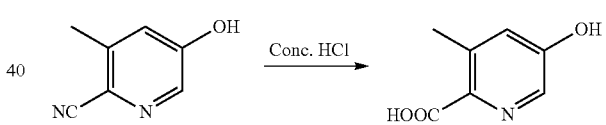

5-hydroxy-3-methyl-2-cyanopyridine (3.1 g 23.1 mmol, 1.0 eq) was dissolved in concentrated hydrochloric acid (60 mL). The mixture was heated to 100° C. and reacted for 24 hours. LC-MS detection showed that there was some raw materials that were not completely reacted. The system was concentrated to obtain a yellowish brown solid product (3.8 g crude product), which was used in the next step without purification.

Step 4: Synthesis of methyl 5-hydroxy-3-methylpicolinate

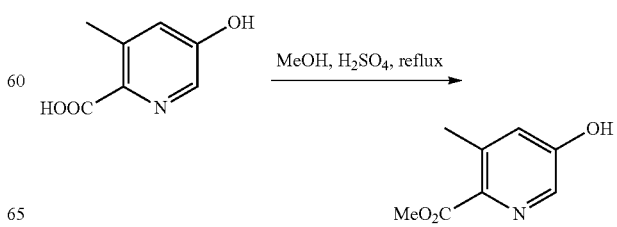

5-hydroxy-3-methylpicolinic acid (3.8 g crude product) was dissolved in methanol (30 mL). Concentrated sulfuric acid (4 mL) was added. The mixture was heated and reacted under reflux for 24 hours. After the completion of the reaction indicated by LC-MS detection, the reaction liquid was directly concentrated. The residue was adjusted with 1N sodium hydroxide solution to a pH value of 8. The mixture was extracted with EA for 8 times. The organic phases were combined, dried and concentrated to obtain a crude product, which was purified by silica gel column chromatography (100-200 mesh silica gel, EA:PE=0-10%) to obtain a white solid product (2.1 g, two-step yield: 55%).

Step 5: Synthesis of methyl 5-((tert-butyldimethyl-silyl)oxy)-3-methylpicolinate

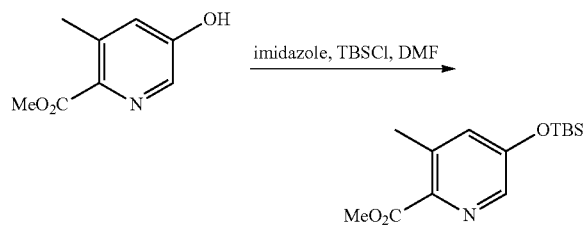

Intermediate methyl 5-hydroxy-3-methylpicolinate (2.4 g, 14.35 mmol, 1.0 eq, combined for two batches) and imidazole (1.46 g, 21.53 mmol, 1.5 eq) were dissolved in DMF (35 mL). The temperature was reduced to 0° C. TBSCl (3.25 g, 21.53 mmol, 1.5 eq) was added. The temperature was recovered to room temperature. The mixture was reacted for 12 hours. After the completion of the reaction indicated by LC-MS detection, water (50 mL) and EA (50 mL) were added. The liquid separation was performed. The organic phase was washed with an edible saturated saline solution (50 mL×2), dried, concentrated to obtain a crude product, which was purified by silica gel column chromatography (100-200-mesh silica gel, EA:PE=0-5%) to obtain a colorless oily product (3.0 g, yield: 74%).

Step 6: Synthesis of methyl 3-(bromomethyl)-5-((tert-butyldimethylsilyl)oxy)picolinate

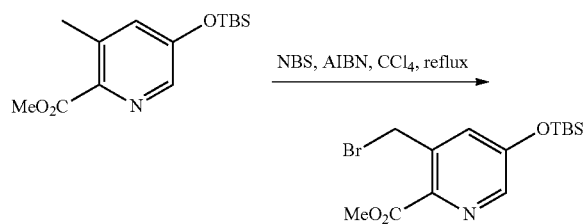

Methyl 5-((tert-butyldimethylsilyl)oxy)-3-methylpicolinate (3.0 g, 10.7 mmol, 1.0 eq) and NBS (2.47 g, 13.8 mmol, 1.3 eq) were added to a CCl₄ solution (30 mL). Azodiisobutyronitrile (175 mg, 1.07 mmol, 0.1 eq) was added. The mixture was heated to reflux and reacted for 3 hours. After the completion of the reaction indicated by LC-MS detection, the system temperature was reduced to room temperature. The reaction liquid was concentrated under a reduced pressure to obtain a crude product, which was purified by silica gel column chromatography (100-200 mesh silica gel, EA:PE=0-5%) to obtain a yellow oily product (3.0 g, crude product), which was directly used in the next step.

Step 7: Synthesis of 6-cyclopropyl-3-hydroxy-5,6-dihydro-7H pyrrolo[3,4-b]pyridin-7-one

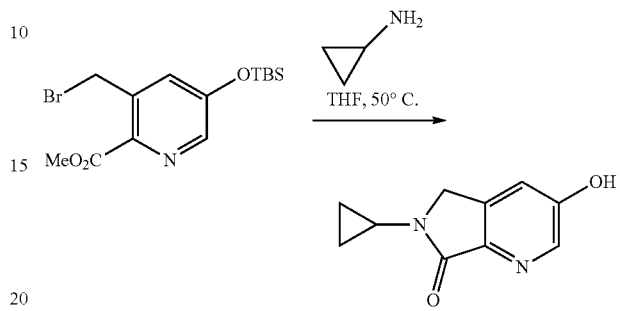

Methyl 3-(bromomethyl)-5-((tert-butyldimethylsilyl)oxy) picolinate (2.0 g, 5.55 mmol, 1.0 eq) and cyclopropylamine (0.95 g, 16.65 mmol, 3.0 eq) were added to THF (20 mL). The mixture was heated to 50° C. and reacted overnight. After the completion of the reaction indicated by LC-MS detection, the reaction liquid was concentrated under a reduced pressure to obtain a crude product, which was purified by silica gel column chromatography (300-400 mesh silica gel, MeOH:DCM=0-10%) to obtain a white solid product (415 mg, two-step yield: 30%).

¹H NMR (300 MHz, DMSO-d₆) δ(ppm): 10.60 (brs, 1H), 8.20 (d, J=2.1 Hz, 1H), 7.28 (d, J=2.1 Hz, 1H), 4.29 (s, 2H), 2.94-2.86 (m, 1H), 0.79-0.74 (m, 4H).

Molecular formula: $C_{10}H_{10}N_2O_2$ Molecular weight: 190.20 LC-MS (Pos, m/z)=191.0[M+H]⁺.

Example 9 Synthesis of Intermediate 3-hydroxy-6,7-dihydro-1,7-naphthyridin-8(5H)-one

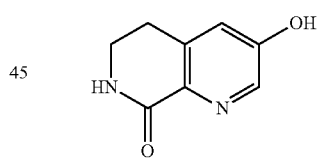

Step 1: Synthesis of methyl 3-(cyanomethyl)-5-hydroxypicolinate

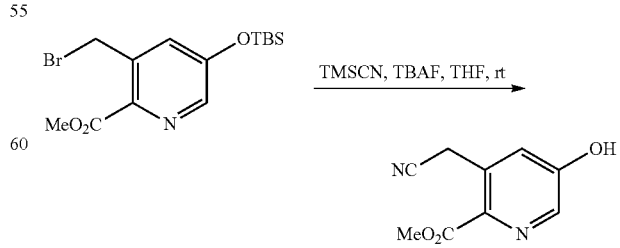

Methyl 3-(bromomethyl)-5-((tert-butyldimethylsilyl)oxy) picolinate (5.0 g, 13.9 mmol, 1.0 eq) was dissolved in THF (50 mL). TMSCN (2.76 g, 27.8 mmol, 2.0 eq) was added at room temperature. 1.0 mol/L of TBAF/THF solution (28 mL, 28 mmol, 2.0 eq) was added. The heat release was evident during the dropwise addition. The rate of the dropwise addition was controlled. After the dropwise addition, the reaction was performed for 2 hours at room temperature. LC-MS detection showed that there was some raw materials that were not completely reacted, the reaction system was directly concentrated to remove most of the solvent. The residue was added to EA (100 mL) and water (100 mL). The liquid separation was performed. The aqueous phase was extracted with EA (50 mL×5). The organic phases were combined, dried, concentrated to obtain a crude product, which was purified by silica gel column chromatography (100-200 mesh silica gel, EA:PE=1:1) to obtain a white solid product (1.5 g crude product), which was directly used in the next step reaction without further purification.

Step 2: Synthesis of Intermediate 3-hydroxy-6,7-dihydro-1,7-naphthyridin-8(5H)-one

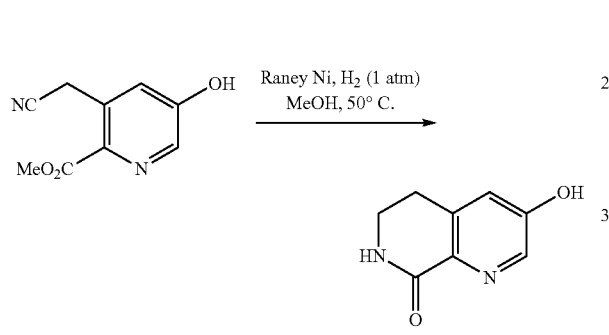

Methyl 3-(cyanomethyl)-5-hydroxypicolinate (1.4 g, 7.28 mmol, 1.0 eq) was dissolved in methanol (30 mL). Raney nickel (1.0 g) was added, and hydrogen substitution was performed for three tines. The mixture was heated to 50° C. under normal pressure, and reacted under being stirred overnight. After the completion of the reaction indicated by LC-MS detection, suction filtration was performed. The filter cake was washed with methanol. The filtrate was concentrated to obtain a crude product, which was purified by preparative HPLC (0.1% TFA, acetonitrile, water as mobile phase) to obtain a white solid product (400 mg, two-step yield: 17%).

$^1$H NMR (400 MHz, DMSO-d$_6$) δ(ppm): 11.33 (br, 1H), 8.24 (s, 1H), 8.14 (d, J=2.0 Hz, 1H), 7.39 (s, 1H), 3.41-3.39 (m, 2H), 2.99-2.96 (m, 2H).

Molecular formula: C$_8$H$_8$N$_2$O$_2$ Molecular weight: 164.16 LC-MS (Pos, m/z)=165.1 [M+H]$^+$.

Example 10 Synthesis of Intermediate 6-cyclopropyl-2-hydroxy-6,7-dihydro-5H-pyrrolo[3,4-b]pyridin-5-one

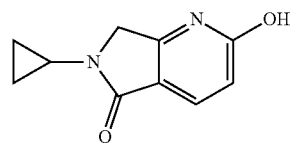 [SMILES: O=C1c2ccc(O)nc2CN1C1CC1]

Flow chart:

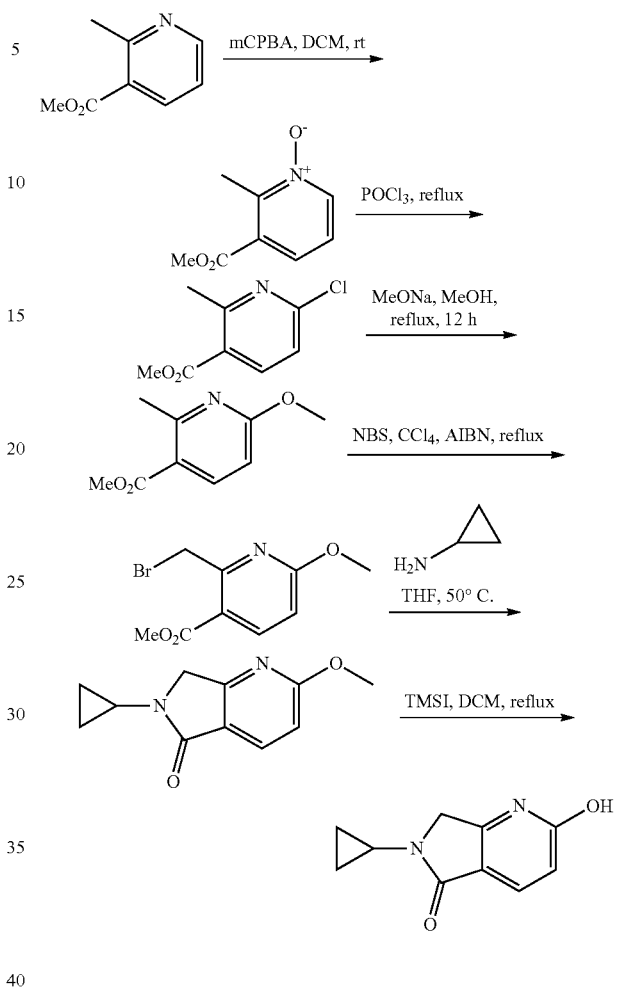

Step 1: Synthesis of 3-(methoxycarbonyl)-2-methylpyridine 1-oxide

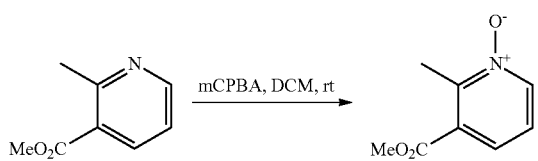

Methyl 2-methylnicotinate (12 g, 80 mmol 1.0 eq) was dissolved in dichloromethane (180 mL). m-CPBA (15.19 g 88 mmol, 1.1 eq) was added. The reaction was performed under being stirred at 25° C. for 12 hours. After the completion of the reaction indicated by LC-MS detection, a saturated mixed solution of sodium sulfite and sodium bicarbonate (100 mL) was added. The liquid separation was performed. Then the aqueous phase was extracted with EA (100 mL×3). The organic phases were combined, dried, concentrated to obtain a crude product, which was purified by silica gel column chromatography (100-200 mesh silica gel, MeOH/EA=0-10%) to obtain a yellow white solid product (9.5 g, yield: 71%).

Step 2: Synthesis of Intermediate methyl 6-chloro-2-methylnicotinate

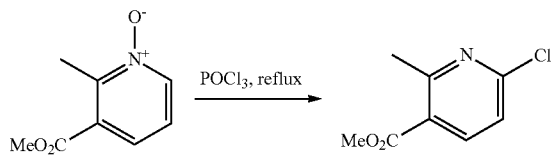

3-(methoxycarbonyl)-2-methylpyridine 1-oxide (9.5 g, 56.14 mmol, 1.0 eq) was added to phosphorus oxychloride (35 mL). The mixture was heated to reflux and reacted for 3 hours. After the completion of the reaction indicated by LC-MS detection, the system temperature was reduced to room temperature. The reaction liquid was directly concentrated under reduced pressure to remove most of the solvent. The concentrate was poured to ice water (100 mL), and adjusted with NaOH to a pH value of 7-8. The mixture was extracted with EA (100 mL×3). The organic phases were combined, dried, and concentrated to obtain a crude product, which was purified by silica gel column chromatography (200-300 mesh silica gel, EA/PE=0-5%) to obtain a a white solid product (2.5 g, yield: 24%).

Step 3: Synthesis of Intermediate methyl 6-methoxy-2-methylnicotinate

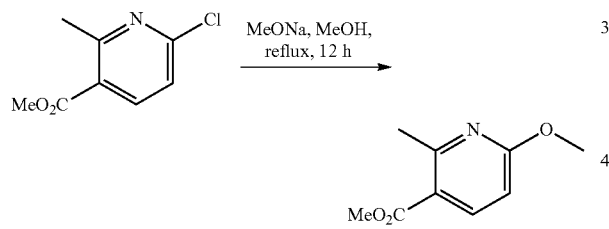

Intermediate methyl 6-chloro-2-methylnicotinate (1.9 g, 10.24 mmol, 1.0 eq) and sodium methoxide (1.1 g, 20.48 mmol, 2.0 eq) were added to methanol (35 mL). The mixture was heated and reacted under reflux for 12 hours. After the completion of the reaction indicated by LC-MS detection, the system temperature was reduced to room temperature. The reaction liquid was directly concentrated under reduced pressure to obtain a crude product, which was purified by silica gel column chromatography (100-200 mesh silica gel, EA/PE=0-2%) to obtain a colorless oily product (1.4 g, yield: 73.7%).

Step 4: Synthesis of Intermediate methyl 2-(bromomethyl)-6-methoxynicotinate

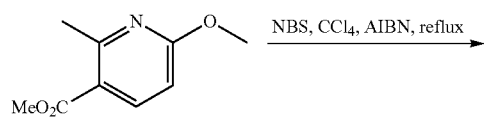

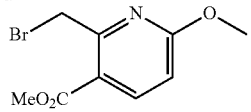

Intermediate methyl 6-methoxy-2-methylnicotinate (1.4 g, 7.73 mmol, 1.0 eq), NBS (1.53 g, 8.60 mmol, 1.2 eq) and azodiisobutyronitrile (115 mg, 0.7 mmol, 0.1 eq) were added to CCl$_4$ (30 mL). The mixture was heated and reacted under reflux for 3 hours. After the completion of the reaction indicated by LC-MS detection, the system temperature was reduced to room temperature. The reaction liquid was directly concentrated under reduced pressure. EA (30 mL) was added. Suction filtration was performed. The filtrate was concentrated to obtain a crude product, which was purified by silica gel column chromatography (100-200 mesh silica gel, EA/PE=0-2%) to obtain a a white-like solid product (2.0 g, crude product), which was directly used in the next step reaction.

Step 5: Synthesis of Intermediate 6-cyclopropyl-2-methoxy-6,7-dihydro-5H-pyrrolo[3,4-b]pyridin-5-one

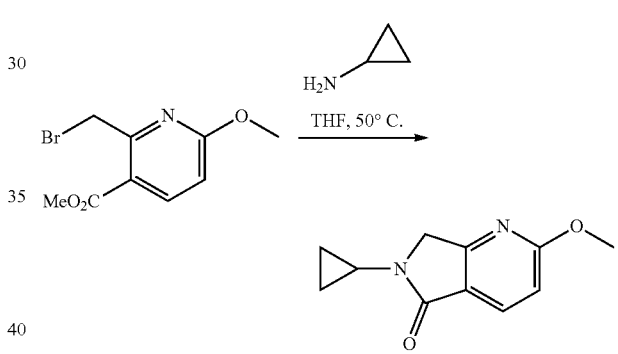

Intermediate methyl 2-(bromomethyl)-6-methoxynicotinate (2.0 g, 7.30 mmol, 1.0 eq) was dissolved in THF (20 mL). Cyclopropylamine (1.25 g, 21.90 mmol, 3.0 eq) was added. The mixture was heated in a sealed tube to 50° C. and reacted for 12 hours. After the completion of the reaction indicated by LC-MS detection, the system temperature was reduced to room temperature. The reaction liquid was directly concentrated under reduced pressure to obtain a crude product, which was purified by silica gel column chromatography (100-200 mesh silica gel, EA/PE=0-50%) to obtain a a white solid product (850 mg, two-step yield: 53.8%).

Step 6: Synthesis of Intermediate 6-cyclopropyl-2-hydroxy-6,7-dihydro-5H-pyrrolo[3,4-b]pyridin-5-one

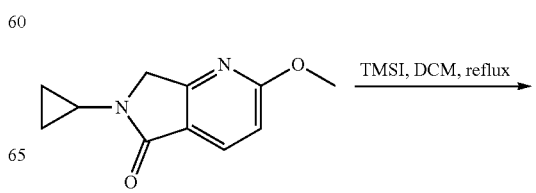

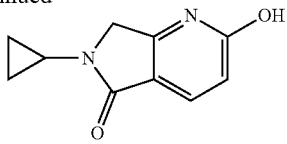

Under the nitrogen protection, Intermediate 6-cyclopropyl-2-methoxy-6,7-dihydro-5H-pyrrolo[3,4-b]pyridin-5-one (850 mg, 4.20 mmol, 1.0 eq) and iodotrimethylsilane (2.52 g, 12.60 mmol, 3.0 eq) were added to DCM (15 mL). The mixture was heated and reacted tinder reflux for 12 hours. After the completion of the reaction indicated by LC-MS detection, the system temperature was reduced to room temperature. The reaction liquid was concentrated under a reduced pressure. EA (20 mL) was added. Suction filtration was performed. The filter cake was dissolved. The mixture was firstly purified by silica gel column chromatography (300-400 mesh silica gel, MeOH/DCM=0-5%) to obtain 850 mg of an impure product, which then purified by preparative thin layer chromatography to obtain a white solid product (320 mg, yield: 40%).

$^1$H NMR (300 MHz, DMSO-$d_6$) δ(ppm): 12.37 (brs, 1H), 7.57 (d, J=8.7 Hz, 1H), 6.33 d J=9.3 Hz, 1H), 4.24 (s, 2H), 2.73-7.71 (m, 1H), 0.74-0.72 (m, 4H).

Molecular formula: $C_{10}H_{10}N_2O_2$ Molecular weight: 190.20 LC-MS (Pos, m/z)=191.1 $[M+H]^+$ Example 11 Synthesis of Intermediate 2-cyclopropyl-6-hydroxy-3,4-dihydro-2,7-naphthyridin-1(2H)-one

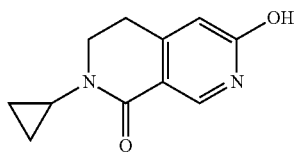 [SMILES: O=C1c2cnc(O)cc2CCN1C1CC1]

Step 1: Synthesis of Intermediate methyl 4-chloro-6-methoxynicotinate

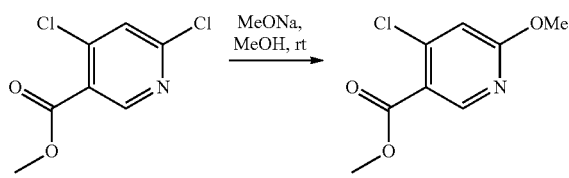

Methyl 4,6-dichloronicotinate (20 g, 97 mmol, 1.0 eq) was dissolved in methanol (80 mL). The temperature was reduced to 0° C. 0.5 mol/L of sodium methoxide methanol solution (195 mL, 97.5 mmol, 1.0 eq) was added dropwise. After the completion of the dropwise addition, the temperature was recovered to room temperature, and the reaction was performed for 2 hours. After the completion of the reaction indicated by LC-MS detection, the system was directly concentrated. DCM (200 mL) is added. The mixture was washed with water (150 mL), washed with saline solution (100 mL), dried, concentrated to obtain a crude product, which was purified by silica gel column chromatography (300-400 mesh silica gel, EA/PE=0-5%) to obtain a product (4.4 g, yield: 22%).

Step 2: Synthesis of Intermediate methyl 6-methoxy-4-vinylnicotinate

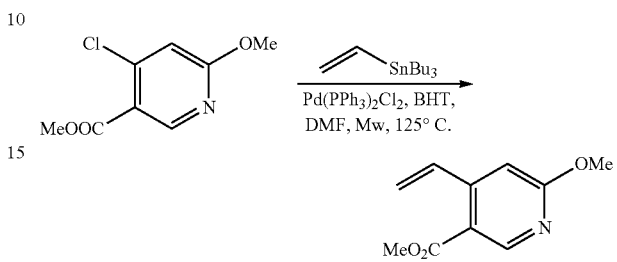

Intermediate methyl 4-chloro-6-methoxynicotinate (1.1 g, 5.47 mmol, 1.0 eq), tributyl(vinyl)stannane (2.6 g, 8.2 mmol, 1.5 eq), 2,6-di-tert-butyl-4-methylphenol (120 mg, 0.55 mmol, 0.1 eq) and Pd(PPh$_3$)Cl$_2$ (380 mg, 0.55 mmol, 0.1 eq) were successively added to DMF (11 mL). The mixture was microwave heated to 125° C. and reacted for 40 minutes. LC-MS detection showed that there was about 15% of raw material that was not completely reacted. The system was cooled to room temperature. (Parallel feeding: a total of 4.4 g of methyl 4-chloro-6-methoxynicotinate was fed, the reaction liquids were combined and post-treated). The reaction liquid was directly concentrated under reduced pressure to obtain a crude product, which was purified by silica gel column chromatography (100-200 mesh silica gel, EA/PE=0-2%) to obtain a product (2.6 g crude product), which was directly used in the next step.

Step 3: Synthesis of Intermediate 2-cyclopropyl-6-methoxy-3,4-dihydro-2,7-naphthyridin-1(2H)-one

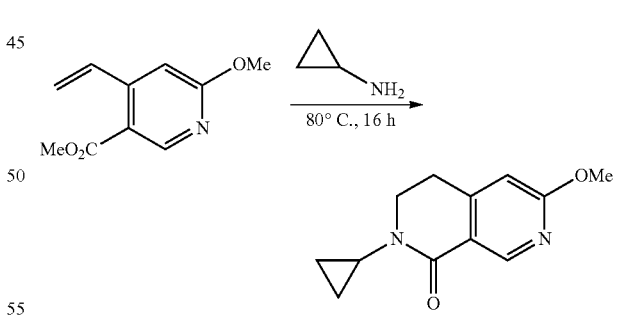

Methyl 6-methoxy-4-vinylnicotinate (2.6 g, crude product) was added to cyclopropylamine (30 mL). The mixture was heated in a sealed tube to 80° C. and reacted for 16 hours. After the completion of the reaction indicated by LC-MS detection, the temperature was reduced to room temperature. The reaction liquid was concentrated under a reduced pressure to obtain a crude product, which was purified by silica gel column chromatography (100-200 mesh silica gel, EA/PE=0-50%) to obtain a white-like solid product (860 mg, two-step yield in total: 72%).

Step 4: Synthesis of Intermediate 2-cyclopropyl-6-hydroxy-3,4-dihydro-2,7-naphthyridin-1(2H)-one

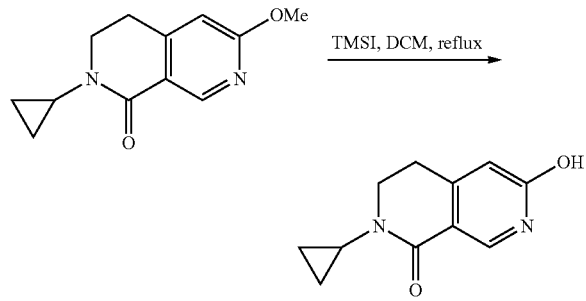

Under the nitrogen protection, Intermediate 2-cyclopropyl-6-methoxy-3,4-dihydro-2,7-naphthyridin-1(2H)-one (860 mg, 3.94 mmol, 1.0 eq) and iodotrimethylsilane (2.36 g, 11.83 mmol, 3.0 eq) were added to DCM (10 mL). The mixture was heated and reacted under reflux for 12 hours. After the completion of the reaction indicated by LC-MS detection, the system temperature was reduced to room temperature. A yellow solid was separated out. Suction filtration was performed. The solid was washed with EA (10 mL). The resulting solid was purified by preparative thin layer chromatography to obtain a white-like solid product (440 mg, yield: 55%).

$^1$H NMR (400 MHz, DMSO-$d_6$) δ(ppm): 11.84 (brs, 1H), 7.83 (s, 1H), 6.14 (s, 1H), 3.39 (t, J=6.0 Hz, 2H), 2.77-2.72 (m, 3H), 0.76-0.74 (m, 2H) 0.73-0.72 (m, 1H).

Molecular formula: $C_{11}H_{12}N_2O_2$ Molecular weight: 204.23 LC-MS (Pos, m/z)=205. [M+H]$^+$ Example 12: Synthesis of (E)-3-((2-(aminomethyl)-3-fluoroallyl)oxy)-6,7-dihydro-1,7-naphthyridin-8(5H)-one (compound 8) hydrochloride

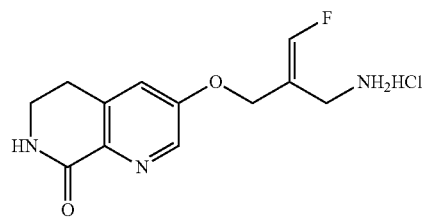

Step 1: Synthesis of (E)-tert-butyl (3-fluoro-2-(((8-oxo-5,6,7,8-tetrahydro-1,7-naphthyridine-3-yl)oxy)methyl)allyl)carbamate

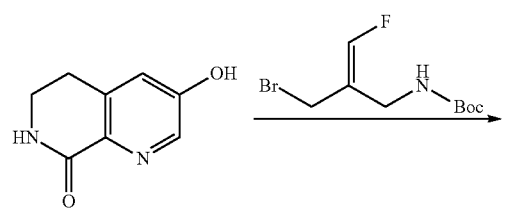

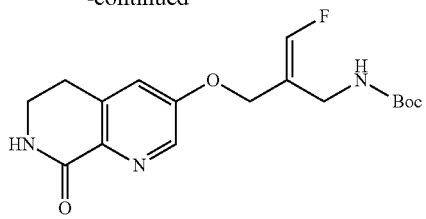

Intermediate 3-hydroxy-6,7-dihydro-1,7-naphthyridin-8(5H)-one (80.0 mg, 0.49 mmol, 1.0 eq) and (E)-tert-butyl (2-(bromomethyl)-3-fluoroallyl)carbamate (130.6 mg, 0.49 mmol, 1.0 eq) were dissolved in DMF. $K_2CO_3$ (101.0 mg, 0.73 mmol, 1.5 eq) was added. The mixture was stirred at room temperature for 12 hours. After the completion of the reaction indicated by TLC detection, water (10 mL) and EA (10 mL) were added. The mixture was stirred. The liquid separation was performed. The aqueous phase was extracted with EA (10 mL). The organic phases were combined and washed with water for three times. The organic phase was dried and concentrated to obtain a crude product, which was purified by silica gel column chromatography (DCM: MeOH=50:1-20:1) to obtain a product (80 mg, yield 46.5%).

Step 2: Synthesis of (E)-3-((2-(aminomethyl)-3-fluoroallyl)oxy)-6,7-dihydro-1,7-naphthyridin-8(5H)-one hydrochloride

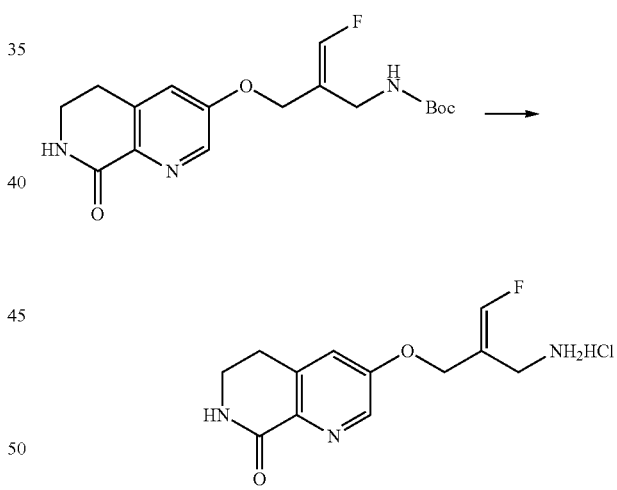

Intermediate (E)-tert-butyl (3-fluoro-2-(((8-oxo-5,6,7,8-tetrahydro-1,7-naphthyridine-3-yl)oxy)methyl)allyl)carbamate (80 mg, 0.23 mmol, 10 eq) was dissolved in EtOH. A solution of hydrogen chloride in ethanol (2 mL) was added. The mixture was stirred at room temperature for 2 hours and concentrated. MTBE (10 mL) was added. A solid was separated out. Suction filtration was performed to obtain a product (49.0 mg, yield 74.8%).

$^1$H NMR (400 MHz, DMSO-$d_6$) δ(ppm): 8.34-8.45 (m, 5H), 7.76 (s, 1H), 7.38 (d, J=84 Hz, 1H), 4.85-4.86 (d, 2H), 3.61-3.63 (m, 2H), 3.41-3.45 (m, 2H), 302-3.05 (m, 2H).

Molecular formula: $CH_{12}H_{14}FN_3O_2$ Molecular weight: 251.26 LC-MS (Pos, m/z)=252.15 [M+H]$^+$.

Example 13: Synthesis of (E)-5-((2-(aminomethyl)-3-fluoroallyl)oxy)-2-cyclopropyl isoindolin-1-one (compound 16) hydrochloride

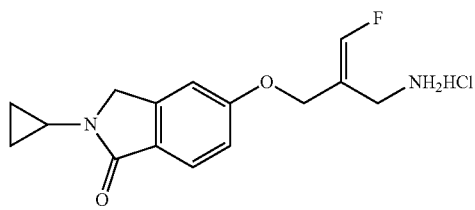

Step 1: Synthesis of (E)-tert-butyl (3-fluoro-2-(((1-oxoisoindolin-5-yl)oxy)methyl)allyl)carbamate

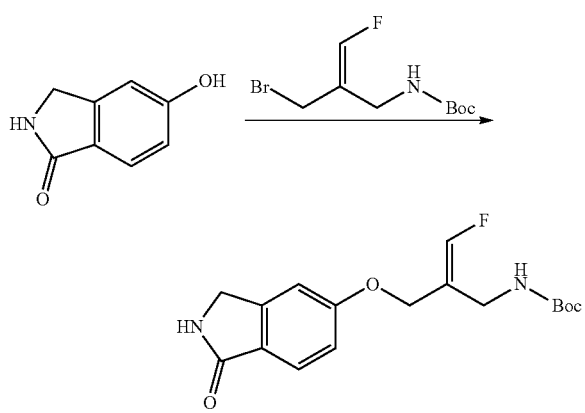

5-hydroxyisoindolin-1-one (130 ng, 0.872 mmol, 1.0 eq) and (E)-tert-butyl (9-(bromoethyl)-3-fluoroallyl)carbamate (234 mg, 0.872 mmol, 1.0 eq) was dissolved in DMF. $K_2CO_3$ (181 mg, 1.308 mmol, 1.5 eq) was added. The reaction was performed under being stirred at room temperature overnight. After the completion of the reaction indicated by TLC detection, water was added. The mixture was extracted with EA. The organic phase was concentrated to obtain a crude product, which was separated by preparative thin layer chromatography (PE:EA=1:1) to obtain a product (219 mg, yield: 74.7%).

Step 2: Synthesis of (E)-tert-butyl (2-(((2-cyclopropyl-1-oxoisoindolin-5-yl)oxy)methyl)-3-fluoroallyl-carbamate

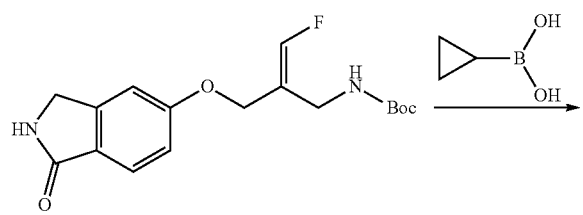

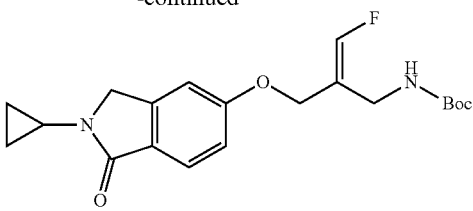

Intermediate (E)-tert-butyl (3-fluoro-2-(((1-oxoisoindolin-5-yl)oxy)methyl)allyl)carbamate (219 mg, 0.651 mmol, 1.0 eq) was dissolved in THF (10 mL). Cyclopropylboric acid (72 ng, 0.846 mmol, 1.3 eq), triethylamine (329 mg, 3.255 mmol, 5.0 eq), pyridine (412 mg, 5.209 mmol, 8.0 eq) and copper acetate (236 mg, 1.182 mmol, 1.8 eq) were added. The reaction was performed at 70° C. for 5 days, during which cyclopropylboric acid (72 mg×3) was supplemented. The reaction liquid was cooled. An aqueous saturated sodium bicarbonate solution was added. The mixture was stirred and extracted with EA. The liquid separation was performed. The organic phase was dried over anhydrous sodium sulfate, concentrated to obtain a crude product, which was separated by preparative thin layer chromatography (PE:EA=1:1) to obtain a product (152 ng, yield: 62%).

Step 3: Synthesis of (E)-5-((2-(aminomethyl)-3-fluoroallyl)oxy)-2-cyclopropyl isoindolin-1-one hydrochloride

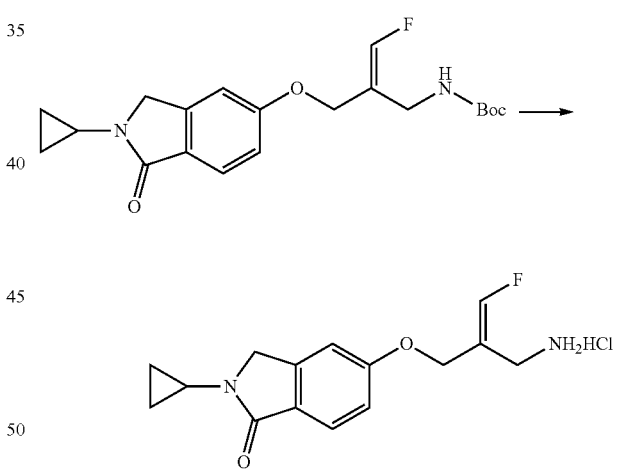

Intermediate (E)-tert-butyl (2-(((2-cyclopropyl-1-oxoisoindolin-5-yl)oxy)methyl)-3-fluoroallylcarbamate (100 mg, 0.266 mmol, 1.0 eq) was dissolved in ethanol (4 mL). Hydrogen chloride ethanol solution (0.5 mL) was added. The mixture was stirred for 12 hours. A solid was separated out. Suction filtration was performed. The filter cake was dried to obtain a product (60.0 mg, yield: 72.3%).

$^1$H NMR (400 MHz, DMSO-$d_6$) δ(ppm): 8.36 (m, 3H), 7.55-7.58 (d, J=8.4 Hz, 1H), 7.32 (d, J=82 Hz, 1H), 7.16 (s, 1H), 7.07 (d, J=8.4 Hz, 1H), 4.72 (s, 2H), 4.33 (s, 2H), 3.58-3.59 (d, 2H), 2.85-2.88 (m, 1H), 0.76-0.81 (m, 4H).

Molecular formula: $C_{15}H_{17}FN_2O_2$ Molecular weight: 276.31 LC-MS (Pos, m/z)=277.2[M+H]$^+$.

Example 14: Synthesis of (E)-5-((2-(aminomethyl)-3-fluoroallyl)oxy)-N,N-diethylpicolinamide (compound 19) hydrochloride

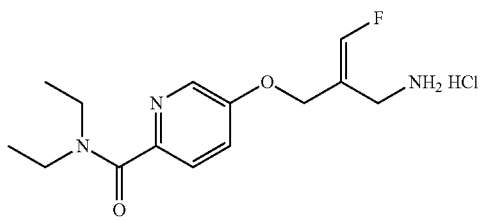

Step 1: Synthesis of N,N-diethyl-5-hydroxypicolinamide

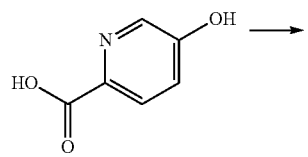

A raw material 5-hydroxypicolinic acid (200 mg, 1.580 mmol, 1.0 eq) was dissolved in DMF. HATU (708 mg, 1.868 mmol, 1.3 eq), diethylamine (156 mg, 2.156 mmol, 1.5 eq) and DIPEA (372 mg, 2.872 mmol, 2.0 eq) were successively added. Under the nitrogen protection, the reaction was performed under being stirred at room temperature overnight. After the completion of the reaction indicated by TLC detection, water was added for dilution. The mixture was extracted with EA. The liquid separation was performed. The organic phase was washed with water, dried over anhydrous sodium sulfate, concentrated to obtain a crude product, which was separated by preparative thin layer chromatography (DCM:MeOH=15:1) to obtain a product (140 mg, yield: 50.2%).

Step 2: Synthesis of (E)-tert-butyl (2-(((6-(diethylcarbamoyl)pyridin-3-yl)oxy)methyl)-3-fluoroallyl) carbamate

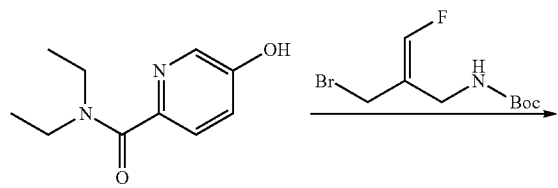

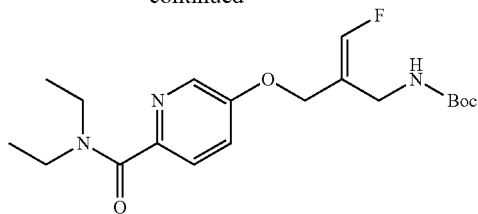

Intermediate N,N-diethyl-5-hydroxypicolinamide (140 mg, 0.721 mmol, 1.0 eq) was dissolved in DMF. (E)-tert-butyl (2-(bromomethyl)-3-fluoroallyl)carbamate (193 mg, 0.721 mmol, 1.0 eq) and K₂CO₃ (149 mg, 1.08 mmol, 1.5 eq) were added. The mixture was stirred at room temperature overnight. After the completion of the reaction indicated by TLC detection, water was added for dilution. The mixture was extracted with DCM. The organic phase was washed with water, dried over anhydrous sodium sulfate, and concentrated to obtain a crude product, which was purified by preparative thin layer chromatography (PE:EA=1:1) to obtain a product (139 mg, yield: 50.5%).

Step 3: Synthesis of (E)-5-((2-(aminomethyl)-3-fluoroallyl)oxy)-N,N-diethylpicolinamide hydrochloride

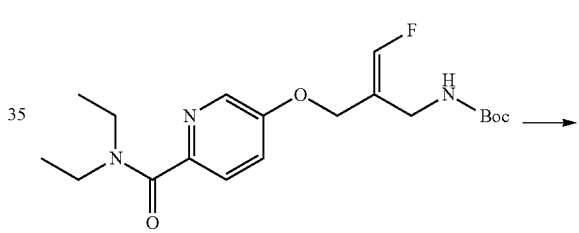

Intermediate (E)-tert-butyl (2-(((6-diethylcarbamoyl)pyridin-3-yl)oxy)methyl)-3-fluoroallyl)carbamate (139 mg) was dissolved in ethanol (4 mL). Hydrogen chloride ethanol solution (0.5 mL) was added. The mixture was stirred for 12 hours. A solid was separated out. MTBE was added. Suction filtration was performed. The filter cake was dried to obtain a product (77 mg, yield: 66.3%).

$^1$H NMR (400 MHz, DMSO-$d_6$) δ(ppm): 8.37-8.31 (m, 4), 7.57-7.55 (d, 2H), 7.35 (d, J=82 Hz, 1H), 4.77 (s, 2H), 3.61 (s, 2H), 3.43 (m, 2H), 3.31 (m, 2H), 1.13-1.07 (m, 6H).

Molecular formula: $C_{14}H_{20}FN_3O_2$ Molecular weight: 281.33 LC-MS (Pos, m/z)=282.1 [M+H]$^+$.

Example 15: Synthesis of (E)-1-(2-(aminomethyl)-3-fluoroallyl)-N,N-diethylindoline-5-carboxamide (compound 20) hydrochloride

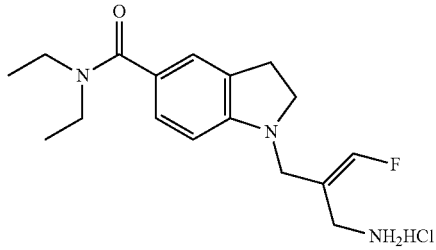

Flow chart:

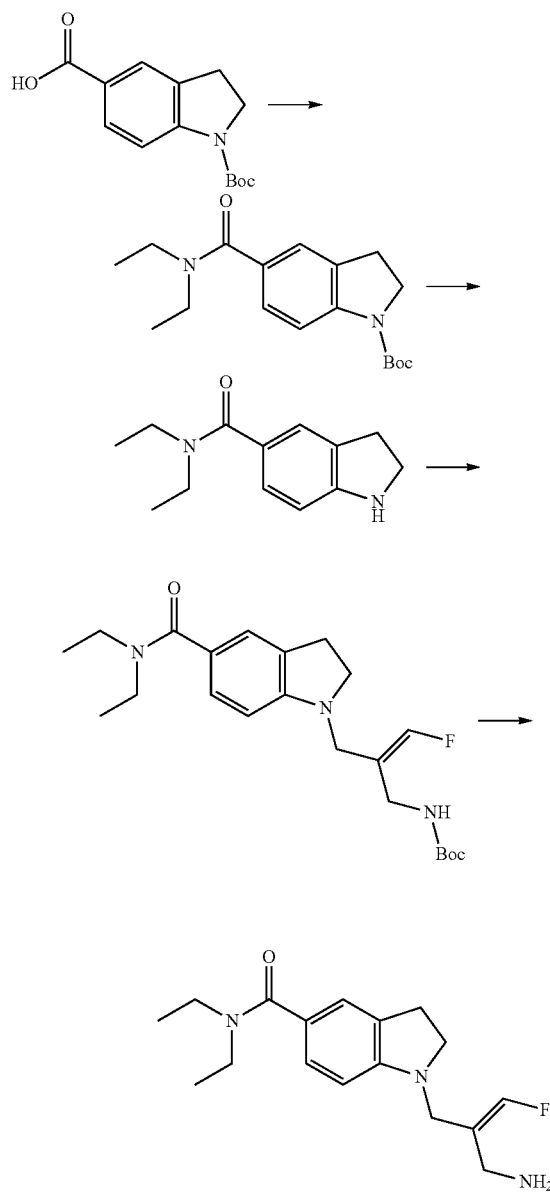

Step 1: Synthesis of Tert-butyl 5-(diethylcarbamoyl)indoline-1-carboxylate

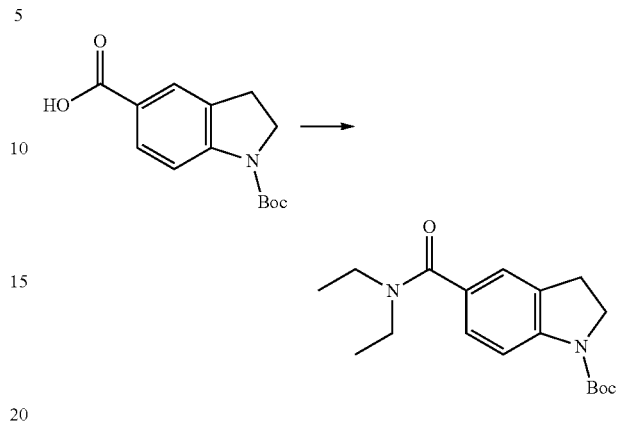

A raw material 1-(tert-butoxycarbonyl)indoline-5-carboxylic acid (230.0 mg, 0.87 mmol, 1.0 eq), HATU (498.2 ng 1.31 mmol, 1.5 eq) and triethylamine (265.2 mg, 2.62 mmol, 3.0 eq) were dissolved in DMF. The mixture was stirred for 1 hour, and then diethylamine (95.8 mg, 1.31 mmol, 1.5 eq) was added. The stirring was continued for another 2 hours. After the completion of the reaction indicated by LC-MS detection, Water (10 mL) and EA (10 mL) were added. The liquid separation was performed. The organic phase was washed with water for three times, dried, and concentrated to obtain a product (270 ng, yield: 97.1%).

Step 2: Synthesis of N,N-diethylindoline-5-carboxamide

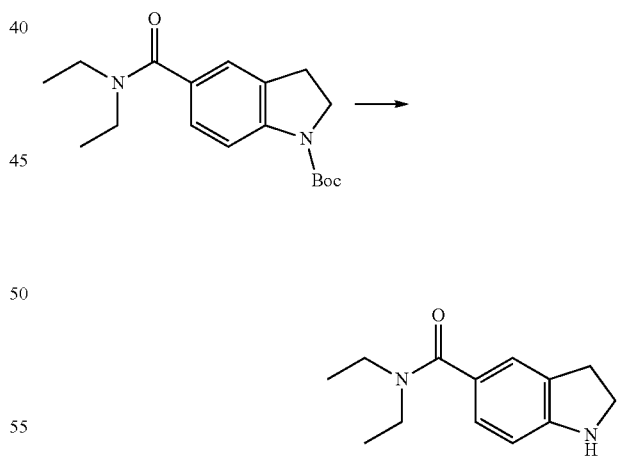

Intermediate tert-butyl 5-(diethylcarbamoyl)indoline-1-carboxylate (230.0 mg, 0.72 mmol, 1.0 eq) was dissolved in EtOH (2 mL). A solution of hydrogen chloride in ethanol (1 mL) was added. The mixture was reacted at 50° C. for 2 hour. After the completion of the reaction indicated by TLC detection, an aqueous saturated sodium bicarbonate solution (10 mL) and EA (10 mL) were added. The liquid separation was performed. The organic phase was dried and concentrated to obtain a product (134.0 mg, yield: 85.0%).

Step 3: Synthesis of (E)-tert-butyl (2-((5-(diethyl-carbamoyl)indoline-1-yl)methyl)-3-fluoroallyl)carbamate

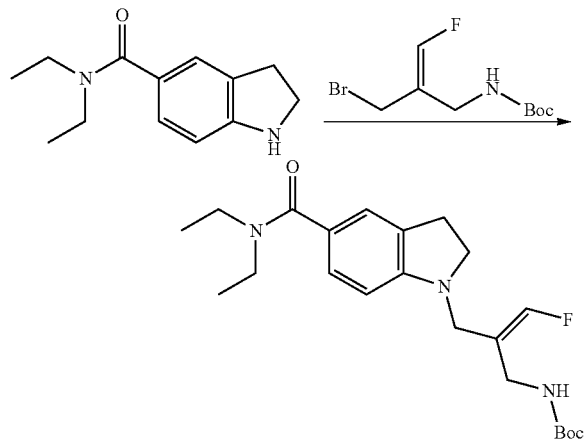

Intermediate N,N-diethylindoline-5-carboxamide (118.0 mug, 0.54 mmol, 1.0 eq) and (E)-tert-butyl (2-(bromomethyl)-3-fluoroallyl)carbamate (144.8 ng, 0.54 mmol, 1.0 eq) were dissolved in toluene. Ag$_2$CO$_3$ (178.7 mg, 0.65 mmol, 1.2 eq) was added. The mixture was reacted at 50° C. for 2 hours. DCM (10 mL) was added. Suction filtration was performed. The filtrate was concentrated to obtain a crude product, which was separated by preparative thin layer chromatography (PE:EA=1:1) to obtain a product (129.0 mg, yield 58.9%).

Step 4: Synthesis of (E)-1-(2-(aminomethyl)-3-fluoroallyl)-N,N-diethylindoline-5-carboxamide hydrochloride

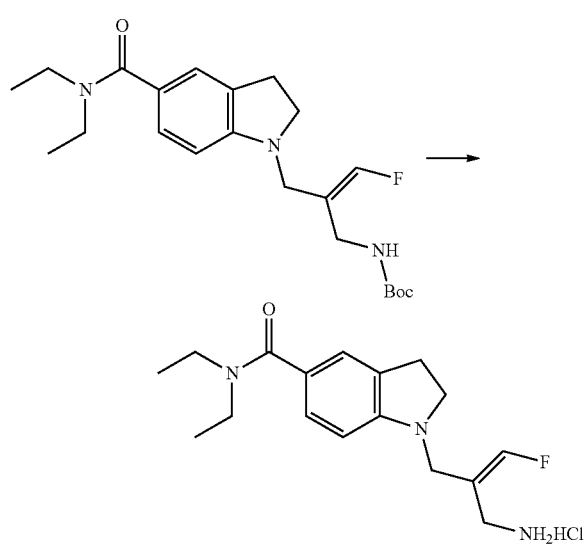

Intermediate (E)-tert-butyl (2-((5-(diethylcarbamoyl)indoline-1-yl)methyl)-3-fluoroallyl)carbamate (120.0 mg, 0.29 mmol, 1.0 eq) was dissolved in EtOH (2 mL). A solution of hydrogen chloride in ethanol (1 mL) was added. The reaction was performed at room temperature for 12 hours. After the completion of the reaction indicated by LC-MS detection, DCM (10 mL) was added and the mixture was concentrated. MTBE (10 mL) was added and the mixture was concentrated. A solid was separated out. Suction filtration was performed to obtain a product (76.0 mg, yield 76.7%).

$^1$H NMR (400 MHz, DMSO-d$_6$) δ(ppm): 8.39 (s, 3H), 7.13 (d, J=84 Hz, 1H), 7.05 (m, 2H), 6.73-6.75 (m, 1H), 3.83 (s, 2H), 3.49-3.50 (m, 2H), 3.27-3.34 (m, 6H), 2.90-2.94 (m, 2H), 1.07-1.24 (m, 6H).

Molecular formula: C$_{17}$H$_{24}$FN$_3$O Molecular weight: 305.40 LC-MS (Pos, m/z)=306.14 [M+H]$^+$.

Example 16: Synthesis of (E)-6-((2-(aminomethyl)-3-fluoroallyl)oxy)-2-cyclopropyl-1,2-dihydro-3H-pyrrolo-[3,4-c]pyridin-3-one (compound 21) trifluoroacetate

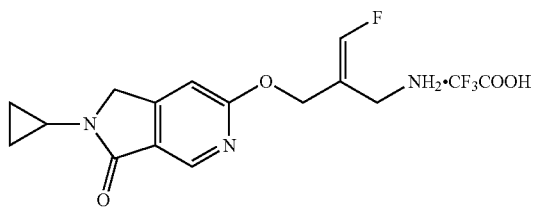

Step 1: Synthesis of (E)-tert-butyl (2-(((2-cyclopropyl-3-oxo-2,3-dihydro-1H-pyrrolo[3,4-c]pyridin-6-yl)oxy)methyl)-3-fluoroallyl)carbamate

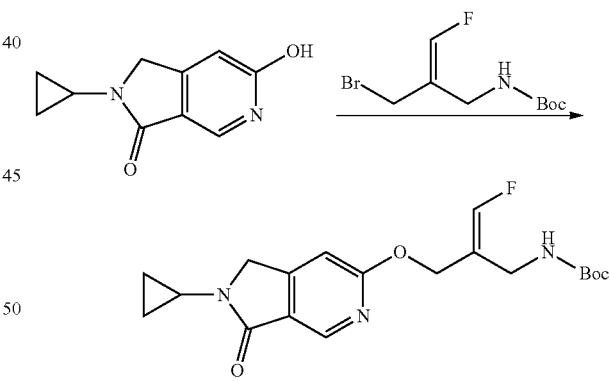

2-cyclopropyl-6-hydroxy-1,2-dihydro-3H-pyrrolo-[3,4-c]pyridin-3-one (150.0 mg, 0.79 mmol 1.0 eq) and (E)-tert-butyl (2-(bromomethyl)-3-fluoroallyl)carbamate (211.4 mg, 0.79 mmol, 1.0 eq) were dissolved in toluene. Ag$_2$CO$_3$ (260.9 mg, 0.95 mmol, 1.2 eq) was added. The mixture was stirred at 80° C. for 2 hours. After the completion of the reaction indicated by TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by preparative thin layer chromatography (PE:EA=1:1) to obtain a product (92 mg, yield: 30.8%).

Step 2: Synthesis of (E)-6-((2-(aminomethyl)-3-fluoroallyl)oxy)-2-cyclopropyl-1,2-dihydro-3H-pyrrolo-[3,4-c]pyridin-3-one trifluoroacetate

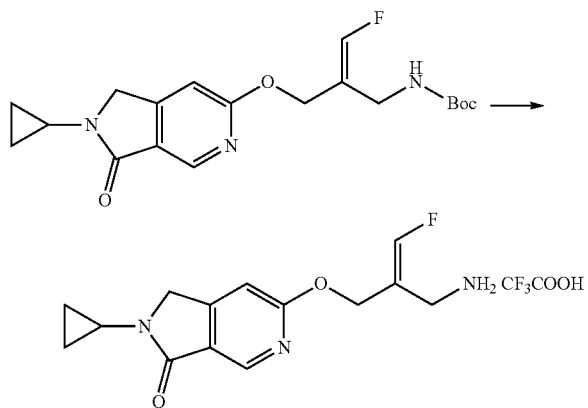

(E)-tert-butyl (2-((2-cyclopropyl-3-oxo-2,3-dihydro-1H-pyrrolo[3,4-c]pyridin-6-yl)oxy)methyl)-3-fluoroallyl)carbamate (92.0 mg, 0.24 mmol, 1.0 eq) was dissolved in DCM. CF$_3$COOH (0.5 mL) was added. The mixture was stirred for 12 hours and concentrated to obtain a crude product, which was purified by preparative thin layer chromatography (DCM:MeOH=10:1) to obtain a product (35.0 mg, yield: 37.3%).

$^1$H NMR (400 MHz, DMSO-d$_6$) δ(ppm): 8.49 (s, 1H), 7.87 (s, 3H), 7.32 (d, J=82.4 Hz, 1H), 7.03 (s, 1H), 4.91 (s, 2H), 4.42 (s, 2H), 3.61 (m, 2H), 2.88 (m, 1H), 0.78-0.82 (m, 4H).

Molecular formula: C$_{14}$H$_{16}$FN$_3$O$_2$ Molecular weight: 277.30 LC-MS (Pos, m/z)=278.16 [M+H]$^+$.

Example 17: Synthesis of (E)-6-((2-(aminomethyl)-3-fluoroallyl)oxy)-2-cyclopropyl-3,4-dihydro-2,7-naphthyridin-1(2H)-one (compound 22)

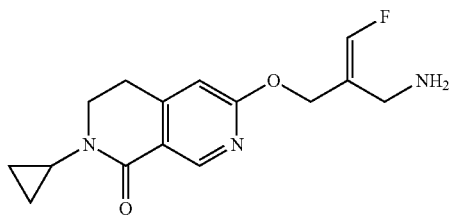 [SMILES: NC/C(=C\F)COc1cc2c(cn1)C(=O)N(C1CC1)CC2]

Step 1: Synthesis of (E)-tert-butyl (2-(((7-cyclopropyl-8-oxo-5,6,7,8-tetrahydro-2,7-naphthyridine-3-yl)oxy)methyl)-3-fluoroallyl)carbamate

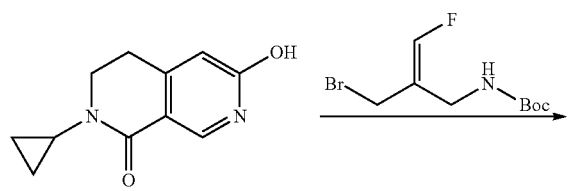

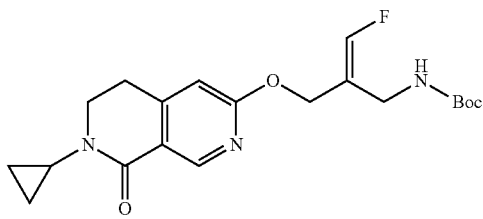

2-cyclopropyl-6-hydroxy-3,4-dihydro-2,7-naphthyridin-1(2H)-one (63.5 mg. 0.31 mmol, 1.0 eq) and (E)-tert-butyl (2-(bromomethyl)-3-fluoroallyl)carbamate (100.0 mg, 0.37 mmol, 1.2 eq) were dissolved in toluene. Ag$_2$CO$_3$ (102.8 mg, 0.37 mmol, 1.2 eq) was added. The mixture was stirred at 80° C. for 2 hours. After the completion of the reaction indicated b TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by preparative thin layer chromatography (PE:EA=1:1) to obtain a product (104.0 mg, yield: 85.9%).

Step 2: Synthesis of (E)-6-((2-(aminomethyl)-3-fluoroallyl)oxy)-2-cyclopropyl-3,4-dihydro-2,7-naphthyridin-1(2H)-one

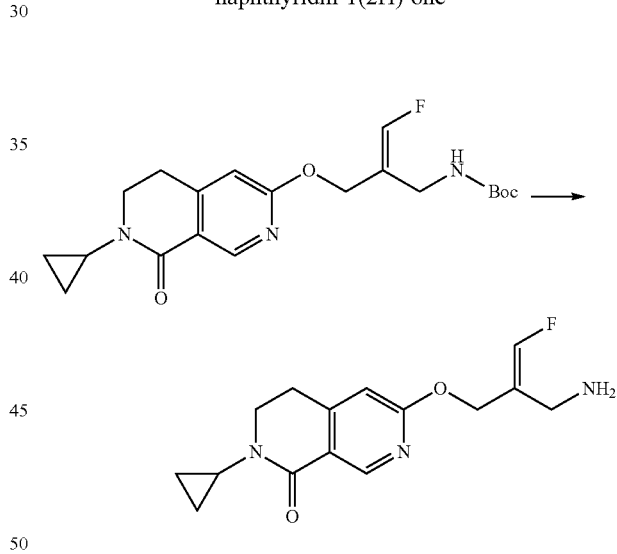

(E)-tert-butyl (2-(((7-cyclopropyl-8-oxo-5,6,7,8-tetrahydro-2,7-naphthyridine-3-yl)oxy)methyl)-3-fluoroallyl)carbamate (104.0 mg, 0.26 mmol, 1.0 eq) was dissolved in EtOH. Hydrogen chloride ethanol solution (0.5 mL) was added. The mixture was stirred at room temperature for 12 hours, and concentrated to obtain a crude product, which was purified by silica gel column chromatography (DCM:MeOH=20:1-10:1) to obtain a product (38.6 mg, yield: 44.3%).

$^1$H NMR (400 MHz, DMSO-d$_6$) δ(ppm): 8.60 (s, 1H), 7.32 (d, J=84 Hz, 1H), 6.78 (s, 1H), 4.91 (s, 2H), 3.59 (s, 2H), 3.46 (m, 2H), 3.04-3.06 (m, 2H), 2.92 (s, 2H), 2.82 (m, 1H), 0.68-0.78 (m, 4H).

Molecular formula: C$_{15}$H$_{18}$FN$_3$O$_2$ Molecular weight: 291.33 LC-MS (Pos, m/z)=292.25 [M+H]$^+$.

Example 18: Synthesis of (Z)-2-((2-(aminomethyl)-3-fluoroallyl)oxy)-6-cyclopropyl-7,8-dihydro-1,6-naphthyridin-5(6H)-one (compound 23) trifluoroacetate

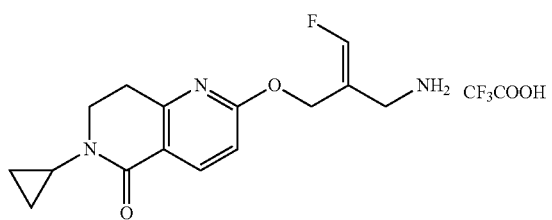 [SMILES: NC/C(=C/F)COc1ccc2c(n1)CCN(C1CC1)C2=O ; "CF3COOH"]

Step 1: Synthesis of (Z)-tert-butyl (2-(((6-cyclopropyl-5-oxo-5,6,7,8-tetrahydro-1,6-naphthyridin-2-yl)oxy)methyl)-3-fluoroallyl)carbamate

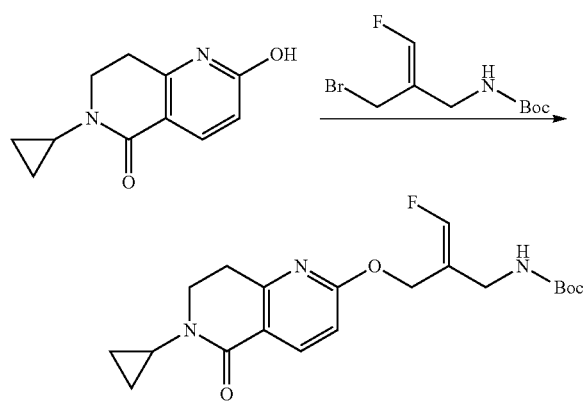

6-cyclopropyl-2-hydroxy-7,8-dihydro-1,6-naphthyridin-5(6H)-one (2.5 g, 12.2 mmol, 1.0 eq) and (Z)-tert-butyl (2-(bromomethyl)-3-fluoroallyl)carbamate (4.9 g, 18.4 mmol, 1.5 eq) were dissolved in toluene. Ag$_2$CO$_3$ (6.75 g, 24.5 mmol, 2.0 eq) was added. The mixture was stirred at 80° C. for 12 hours. After the completion of the reaction indicated by TLC detection, a mixed solvent of DCM and MeOH (10:1, 100 mL) was added. The mixture was stirred. Suction filtration was performed. The filter cake was washed with MeOH (20 mL). The filtrate was concentrated to obtain a crude product, which was purified by silica gel column chromatography (PE:EA=5:1-1:1) to obtain a product (2.0 g, yield: 41.6%).

Step 2: Synthesis of (Z)-2-((2-(aminomethyl)-3-fluoroallyl)oxy)-6-cyclopropyl-7,8-dihydro-1,6-naphthyridin-5(6H)-one trifluoroacetate

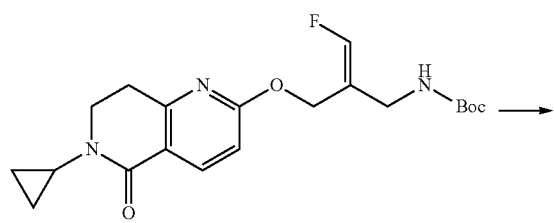

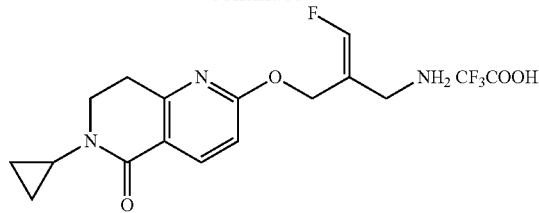

(Z)-tert-butyl (2-(((6-cyclopropyl-5-oxo-5,6,7,8-tetrahydro-1,6-naphthyridin-2-yl)oxy)methyl)-3-fluoroallyl)carbamate (2.0 g, 5.11 mmol, 1.0 eq) was dissolved in DCM. CF$_3$COOH (5 mL) was added. The mixture was stirred for 12 hours and concentrated to obtain a crude product, which was firstly purified by silica gel column chromatography (DCM:MeOH=50:1-10:1), and then lyophilized to obtain a product (1.0 g, yield: 48.3%).

$^1$H NMR (400 MHz, DMSO-d$_6$) δ(ppm): 8.04-8.12 (m, 4H), 7.20 (d, J=84 Hz, 1H), 6.82-6.84 (m, 1H) 4.92-4.98 (d, 2H), 3.52-3.57 (m, 4H), 2.95-2.99 (m, 2H), 2.79-2.82 (m, 1H), 0.65-0.79 (m, 4H).

Molecular formula: C$_{15}$H$_8$FN$_3$O$_2$ Molecular weight: 291.33 LC-MS (Pos, m/z)=29.27 [M+H]$^+$.

Example 19: Synthesis of (E)-2-((2-(aminomethyl)-3-fluoroallyl)oxy)-6-cyclopropyl-6,7-dihydro-5H-pyrrolo[3,4-b]pyridin-5-one (compound 24) trifluoroacetate

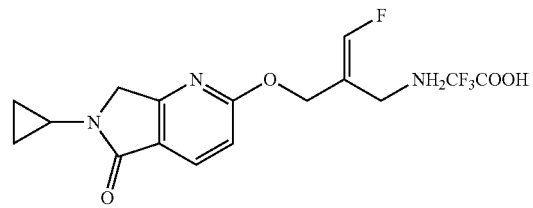

Step 1: Synthesis of (E)-tert-butyl (2-(((6-cyclopropyl-5-oxo-6,7-dihydro-5H-pyrrolo[3,4-b]pyridin-2-yl)oxy)methyl)-3-fluoroallyl)carbamate

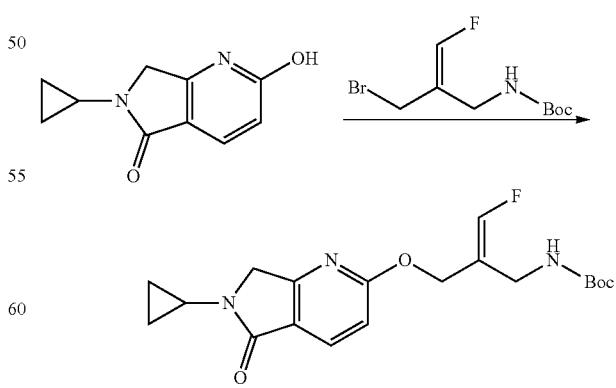

6-cyclopropyl-2-hydroxy-6,7-dihydro-5H-pyrrolo[3,4-b]pyridin-5-one (150.0 mg, 0.79 mmol, 1.0 eq) and (E)-tert-butyl (2-(bromomethyl)-3-fluoroallyl)carbamate (211.4 mg, 0.79 mmol, 1.0 eq) were dissolved in toluene. Ag₂CO₃ (260.9 mg, 0.95 mmol, 1.2 eq) was added. The mixture was stirred at 80° C. for 2 hours. After the completion of the reaction indicated by TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by preparative thin layer chromatography (PE:EA=1:1) to obtain a product (130 mg, yield: 43.6%).

Step 2: Synthesis of (E)-2-((2-(aminomethyl)-3-fluoroallyl)oxy)-6-cyclopropyl-6,7-dihydro-5H-pyrrolo[3,4-b]pyridin-5-one trifluoroacetate

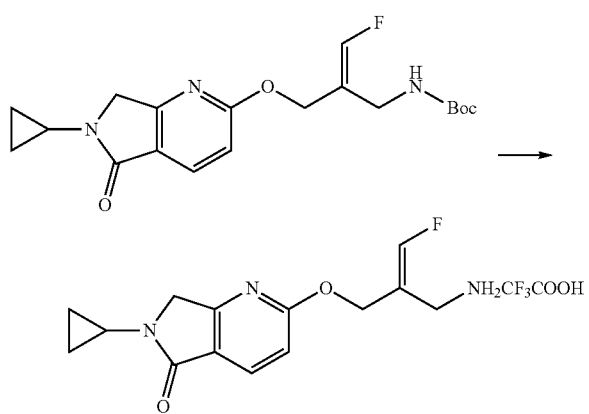

(E)-tert-butyl (2-(((6-cyclopropyl-5-oxo-6,7-dihydro-5H-pyrrolo[3,4-b]pyridin-2-yl)oxy)methyl)-3-fluoroallyl)carbamate (130.0 trig, 0.34 mmol, 1.0 eq) was dissolved in DCM. CF₃COOH (0.5 mL) was added. The mixture was stirred for 12 hours and concentrated to obtain a crude product, which was purified by preparative thin layer chromatography (DCM:MeOH=10:1) to obtain a product (54.4 mg, yield: 40.4%).

¹H NMR (400 MHz, DMSO-d₆) δ(ppm): 8.10 (brs, 3H), 7.94-7.97 (m, 1H), 7.34 (d, J=84 Hz, 1H), 6.92-6.94 (m, 1H), 4.90-4.91 (m, 2H), 4.36 (s, 2H), 3.63 (s, 2H), 2.89-2.92 (m, 1H), 0.83 (m, 4H).

Molecular formula: $C_{14}H_{16}FN_3O_2$ Molecular weight: 277.30 LC-MS (Pos, m/z)=278.20[M+H]⁺.

Example 20: Synthesis of (Z)-2-((2-(aminomethyl)-3-fluoroallyl)oxy)-6-cyclopropyl-6,7-dihydro-5H-pyrrolo[3,4-b]pyridin-5-one (compound 25)

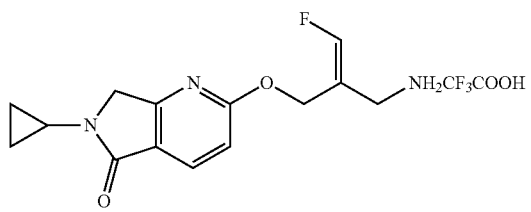

Step 1: Synthesis of (Z)-tert-butyl (2-(((6-cyclopropyl-5-oxo-6,7-dihydro-5H-pyrrolo[3,4-b]pyridin-2-yl)oxy)methyl)-3-fluoroallyl)carbamate

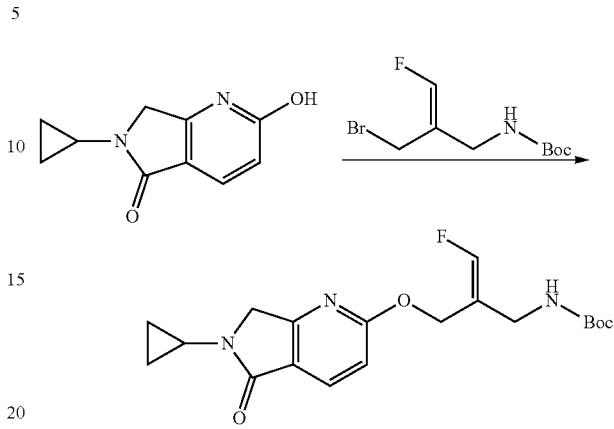

6-cyclopropyl-2-hydroxy-6,7-dihydro-5H-pyrrolo[3,4-b]pyridin-5-one (177 mg, 0.932 mmol, 1.0 eq) and (Z)-tert-butyl (2-(bromomethyl)-3-fluoroallyl)carbamate (300 mg, 1.119 mmol, 1.2 eq) were dissolved in toluene (4 mL). Ag₂CO₃ (334 mg, 1.21 mmol, 1.3 eq) was added. The mixture was stirred at 60° C. for 2 hours. After the completion of the reaction indicated by TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by preparative thin layer chromatography (PE:EA=1:1) to obtain a product (157 mg, yield: 44.7%).

Step 2: Synthesis of (Z)-2-((2-(aminomethyl)-3-fluoroallyl)oxy)-6-cyclopropyl-6,7-dihydro-5H-pyrrolo[3,4-b]pyridin-5-one trifluoroacetate

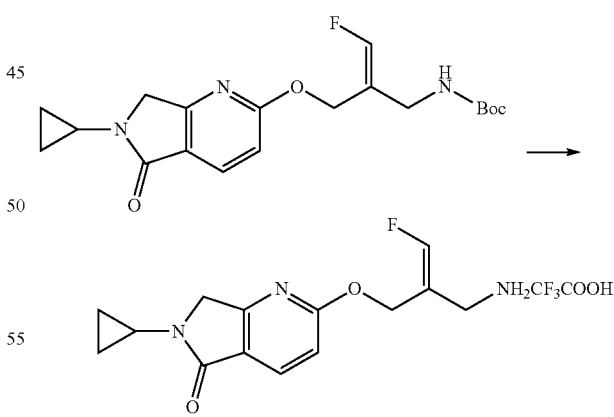

Intermediate (Z)-tert-butyl (2-(((6-cyclopropyl-5-oxo-6,7-dihydro-5H-pyrrolo[3,4-b]pyridin-2-yl)oxy)methyl)-3-fluoroallyl)carbamate (157 mg. 0.416 mmol, 1.0 eq) was dissolved in DCM (4 mL). CF₃COOH (0.5 mL) was added. The mixture was stirred for 12 hours and concentrated to obtain a crude product, which was purified by preparative thin layer chromatography (DCM:MeOH=10:1) to obtain a product (90.0 mg, yield: 55.3%).

$^1$H NMR (400 MHz, DMSO-$d_6$) δ(ppm): 8.00 (brs, 3H), 7.97 (d, J=8.4 Hz, 1H), 7.22 (d, J=82 Hz, 1H), 6.94 (d, J=8.4 Hz, 1H), 5.00-5.01 (d, 2H), 4.37 (s, 2H), 3.59 (s, 2H), 2.89-2.95 (m, 1H), 0.77-0.92 (m, 4H).

Molecular formula: $C_{14}H_{16}FN_3O_2$ Molecular weight: 277.30 LC-MS (Pos, m/z)=278.2 [M+H]$^+$.

Example 21: Synthesis of (E)-2-((2-(aminomethyl)-3-fluoroallyl)oxy)-6-cyclopropyl-7,8-dihydro-1,6-naphthyridin-5(6H)-one (compound 26) trifluoroacetate

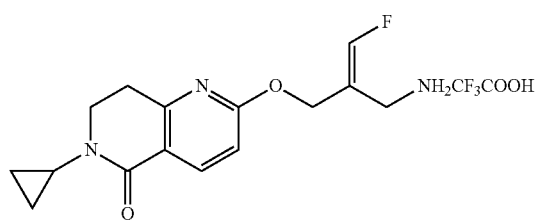

Step 1: Synthesis of (E)-tert-butyl 2-(((6-cyclopropyl-5-oxo-5,6,7,8-tetrahydro-1,6-naphthyridin-2-yl)oxy)methyl)-3-fluoroallylcarbamate

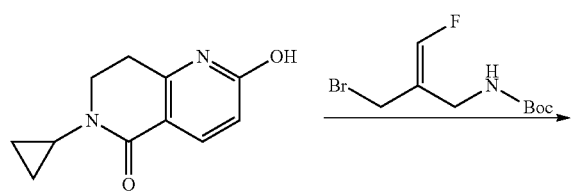

6-cyclopropyl-2-hydroxy-7,8-dihydro-1,6-naphthyridin-5(6H)-one (150 mg, 0.734 mmol, 1.0 eq) and (E)-tert-butyl (2-(bromomethyl)-3-fluoroallyl)carbamate (197 mg, 0.734 mol, 1.0 eq) was dissolved in toluene (5 mL). $Ag_2CO_3$ (243 mg, 0.881 mmol, 1.2 eq) was added. The mixture was stirred at room temperature overnight. After the completion of the reaction indicated by TLC detection, water was added for dilution. The mixture was extracted with DCM. The organic phase was washed with water, dried over anhydrous sodium sulfate, and concentrated to obtain a crude product, which was purified by preparative thin layer chromatography (PE:EA=1:1) to obtain a product (220 mg, yield: 76.6%).

Step 2: Synthesis of (E)-2-((2-(aminomethyl)-3-fluoroallyl)oxy)-6-cyclopropyl-7,8-dihydro-1,6-naphthyridin-5(6H)-one trifluoroacetate

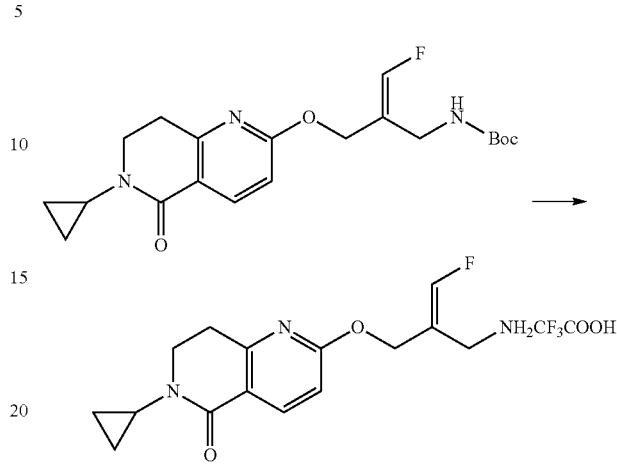

Intermediate (E)-tert-butyl 2-(((6-cyclopropyl-5-oxo-5,6,7,8-tetrahydro-1,6-naphthyridin-2-yl)oxy)methyl)-3-fluoroallylcarbamate (220 mg, 0.562 mmol, 1.0 eq) was dissolved in DCM (4 mL). $CF_3COOH$ (0.5 mL) was added. The mixture was stirred for 12 hours and concentrated to obtain a crude product, which was purified by preparative thin layer chromatography (DCM:MeOH=1:1) to obtain a product (80 mg, yield: 35.1%).

$^1$HNMR (400 MHz, DMSO-$d_6$) δ(ppm): 8.18 (brs, 3H), 8.09-8.12 (d, 1H), 7.34 (d, J=84 Hz, 1H), 7.03 (m, 1H), 4.89 (s, 2H), 3.64 (s, 2H), 3.52-3.55 (t, 2H), 2.96-2.99 (t, 2H), 2.77-2.83 (m, 1H), 0.76-0.79 (m, 2H), 0.66-0.69 (m, 2H).

Molecular formula: $C_{15}H_{18}FN_3O_2$ Molecular weight: 291.33 LC-MS (Pos, m/z)=292.2[M+H]$^+$.

Example 22: Synthesis of (E)-3-((2-(aminomethyl)-3-fluoroallyl)oxy)-6-cyclopropyl-5,6-dihydro-7H-pyrrolo[3,4-b]pyridin-7-one (compound 27) hydrochloride

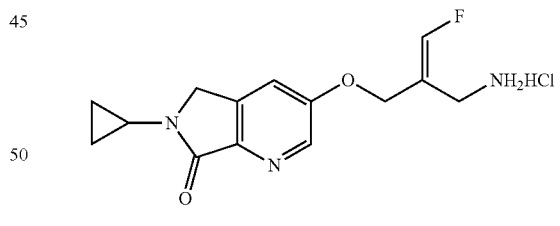

Step 1: Synthesis of (E)-tert-butyl (2-(((6-cyclopropyl-7-oxo-6,7-dihydro-5 1H-pyrrolo[3,4-b]pyridin-3-yl)oxy)methyl)-3-fluoroallyl)carbamate

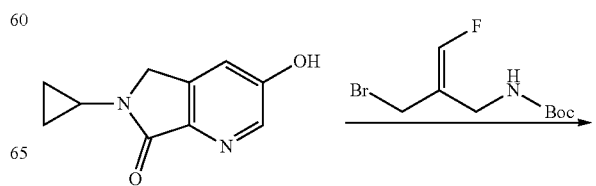

-continued

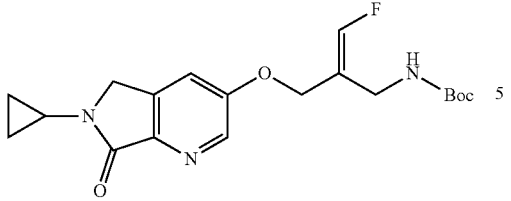

6-cyclopropyl-3-hydroxy-5,6-dihydro-7H-pyrrolo[3,4-b]pyridin-7-one (140 mg, 0.736 mmol, 10 eq) and (E)-tert-butyl (2-(bromomethyl)-3-fluoroallyl)carbamate (197 mg, 0.736 mmol, 1.0 eq) were dissolved in DMF (3 mL). K$_2$CO$_3$ (153 mg, 1.104 mmol, 1.5 eq) was added. The mixture was stirred at room temperature overnight. After the completion of the reaction indicated by TLC detection, water was added for dilution. The mixture was extracted with DCM. The organic phase was washed with water, dried over anhdrous sodium sulfate, and concentrated to obtain a crude product, which was purified by preparative thin layer chromatography (PE:EA=1:1) to obtain a product (213 mg, yield: 76.3%).

Step 2: Synthesis of (E)-3-((2-aminomethyl)-3-fluoroallyl)oxy)-6-cyclopropyl-5,6-dihydro-7H-pyrrolo[3,4-b]pyridin-7-one hydrochloride

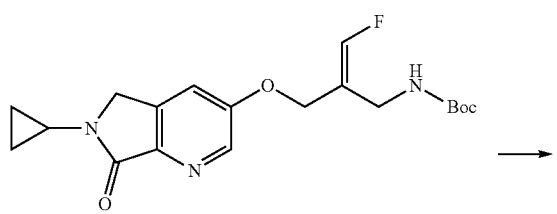

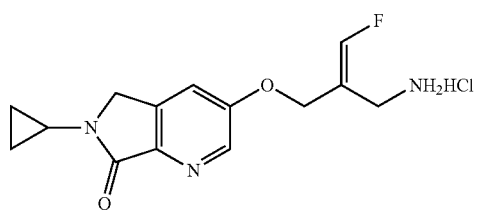

Intermediate (E)-tert-butyl (2-(((6-cyclopropyl-7-oxo-6,7-dihydro-5H-pyrrolo[3,4-b]pyridin-3-yl)oxy)methyl)-3-fluoroallyl)carbamate (213 mg. 0.564 mmol, 1.0 eq) was dissolved in ethanol (4 mL). Hydrogen chloride ethanol solution (1.0 mL) was added. The mixture was stirred for 3 hours. A solid was separated out. Suction filtration was performed. The filter cake was washed with a small amount of ethanol, and dried to obtain a product (90 mg, yield: 50.8%).

$^1$H NMR (400 MHz, DMSO-d) δ(ppm): 8.39-8.42 (m, 4H), 7.66-7.67 (d, 1H), 7.36 (d, J=84 Hz, 1H), 4.80-4.81 (d, 2H), 4.36 (s, 2H), 3.60-3.61 (d, 2H), 2.88-2.94 (m, 1H), 0.77-0.87 (m, 4H).

Molecular formula: C$_{14}$H$_{16}$FN$_3$O$_2$ Molecular weight: 277.3 LC-MS (Pos, m/z)=278.2 [M+H]4.

Example 23: Synthesis of (Z)-3-((2-(aminomethyl)-3-fluoroallyl)oxy)-6-cyclopropyl-5,6-dihydro-7H-pyrrolo[3,4-b]pyridin-7-one (compound 28) hydrochloride

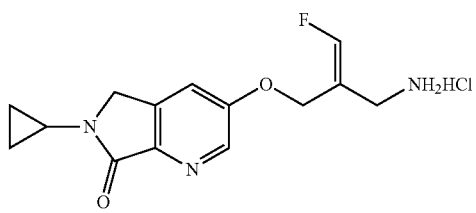

Step 1: Synthesis of (Z)-tert-butyl (2-(((6-cyclopropyl-7-oxo-6,7-dihydro-5H-pyrrolo[3,4-b]pyridin-3-yl)oxy)methyl)-3-fluoroallyl)carbamate

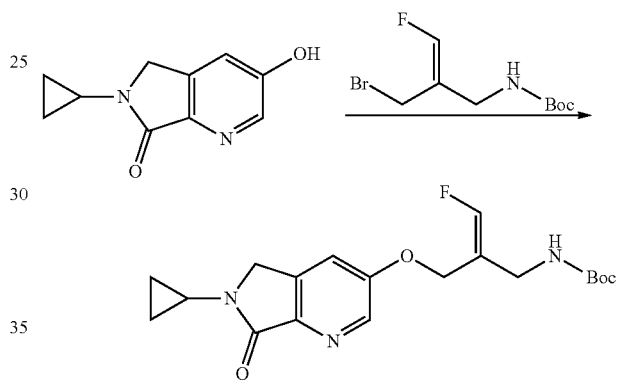

6-cyclopropyl-3-hydroxy-5,6-dihydro-7H-pyrrolo[3,4-b]pyridin-7-one (140.0 mg, 0.74 mmol, 1.0 eq) and (Z)-tert-butyl (2-(bromomethyl)-3-fluoroallyl)carbamate (197.0 mg. 0.74 mmol, 1.0 eq) were dissolved in DMF. K$_2$CO$_3$ (153.0 mg, 1.11 mmol, 1.5 eq) was added. The mixture was stirred at room temperature for 12 hours. After the completion of the reaction indicated by TLC detection, water (10 mL) and EA (10 mL) were added. The mixture was stirred. The liquid separation was performed. The aqueous phase was extracted once with EA (10 mL). The organic phases were combined, washed with water for three times, dried, and concentrated to obtain a crude product, which was purified by preparative thin layer chromatography (PE:EA=1:1) to obtain a product (200 mg, yield: 71.6%).

Step 2: Synthesis of (Z)-3-((2-(aminomethyl)-3-fluoroallyl)oxy)-6-cyclopropyl-5,6-dihydro-7H-pyrrolo[3,4-b]pyridin-7-one hydrochloride

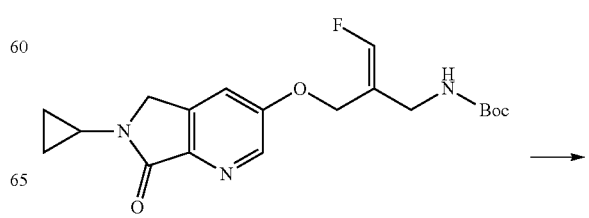

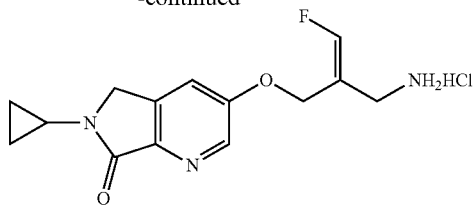

(Z)-tert-butyl (2-(((6-cyclopropyl-7-oxo-6,7-dihydro-5H-pyrrolo[3,4-b]pyridin-3-yl)oxy)methyl)-3-fluoroalkyl)carbamate (200.0 mg, 0.53 mmol, 1.0 eq) was dissolved in EtOH. A solution of hydrogen chloride in ethanol (2 mL) was added. The mixture was stirred at room temperature for 12 hours. A solid was separated out. Suction filtration was performed to obtain a product (50.3 mg, yield: 30.2%).

$^1$H NMR (400 MHz, DMSO-d) δ(ppm): 8.43 (s, 1H), 8.22 (s, 3H), 7.65-7.66 (d, 1H), 7.26 (d, J=84 Hz, 1H), 4.87 (m, 2H), 4.36 (m, 2H), 3.56 (m, 2H) 2.91-2.95 (m, 1H), 0.79-0.84 (m, 4H).

Molecular formula: $C_{14}H_{16}FN_3O_2$ Molecular weight: 277.30 LC-MS (Pos, n/z)=278.22 $[M+H]^+$.

Example 24: Synthesis of (Z)-5-((2-(aminomethyl)-3-fluoroallyl)oxy)-2-cyclopropylisoindolin-1-one (compound 29) hydrochloride

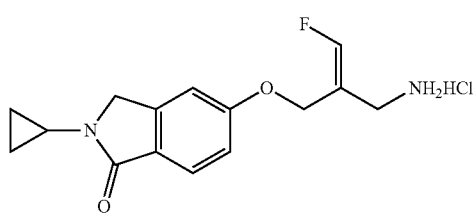

Step 1: Synthesis of (Z)-tert-butyl (3-fluoro-2-(((1-oxoisoindolin-5-yl)oxy)methyl)allyl)carbamate

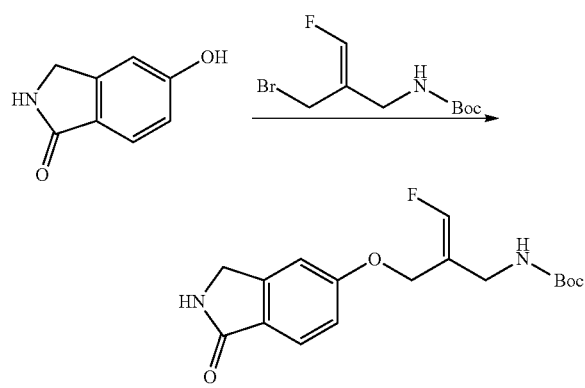

5-hydroxyisoindolin-1-one (130 mg, 0.872 mmol, 1.0 eq) and (Z)-tert-butyl (2-(bromomethyl)-3-fluoroallyl)carbamate (234 mg, 0.873 mmol, 1.0 eq) were dissolved in DMF (3 mL). $K_2CO_3$ (181 mg, 1.310 mmol, 1.5 eq) was added. The reaction was performed under being stirred at room temperature overnight. After the completion of the reaction indicated by TLC detection, water was added. The mixture was extracted with EA. The organic phase was washed with water, dried over anhydrous sodium sulfate, and concentrated to obtain a crude product, which was separated by preparative thin layer chromatography (PE:EA=1:1) to obtain a product (407 mg crude product, directly used in the next step reaction).

Step 2: Synthesis of (Z)-tert-butyl (2-(((2-cyclopropyl-1-oxoisoindolin-5-yl)oxy)methyl)-3-fluoroallyl-carbamate

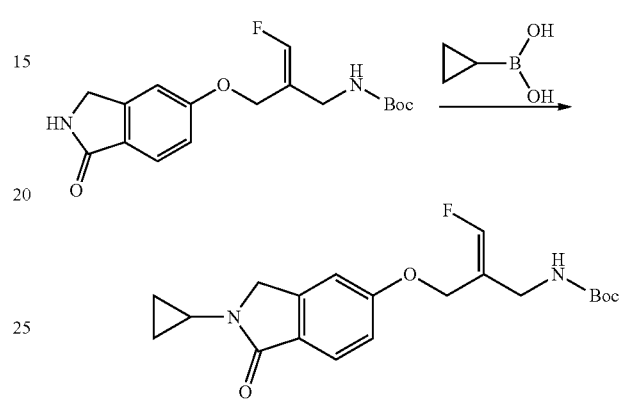

Intermediate (Z)-tert-butyl (3-fluoro-2-(((1-oxoisoindolin-5-yl)oxy)methyl)allyl)carbamate (407 mg crude product) was dissolved in THF (10 mL). Cyclopropyl boric acid (72 mg, 0.84 mmol), triethylamine (329 mg, 3.25 mmol), pyridine (412 mg, 5.21 mmol) and copper acetate (236 mg, 1.18 mmol) were added. The reaction was performed at 70° C. for 5 days, during which cyclopropylboric acid (72 mg×3) was supplemented. The reaction liquid was cooled. An aqueous saturated sodium bicarbonate solution was added. The mixture was stirred and extracted with EA. The liquid separation was performed. The organic phase was dried over anhydrous sodium sulfate, and concentrated to obtain a crude product, which was separated by preparative thin layer chromatography (PE:EA=1:1) to obtain a product (181 mg, two-step yield: 55.2%).

Step 3: Synthesis of (Z)-5-((2-(aminomethyl)-3-fluoroallyl)oxy)-2-cyclopropylisoindolin-1-one hydrochloride

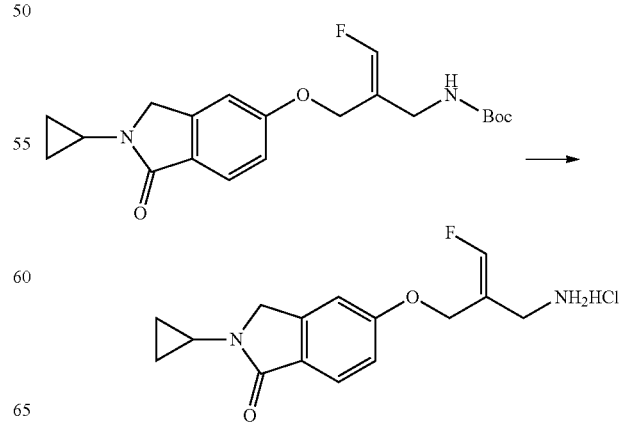

Intermediate (Z)-tert-butyl (2-(((2-cyclopropyl-1-oxoisoindolin-5-yl)oxy)methyl)-3-fluoroallylcarbamate (300 mg, 0.797 mmol, 1.0 eq) was dissolved in DCM (4 mL). Hydrogen chloride ethanol solution (0.5 mL) was added. The mixture was stirred for 12 hours. A solid was separated out. A small amount of MTBE was added. Suction filtration was performed. The filter cake was dried to obtain a product (160 mg, yield: 64.2%).

$^1$H NMR (400 MHz, DMSO-d$_6$) δ(ppm): 8.48 (brs, 3H), 7.55-7.57 (d, J=8.4 Hz, 1H), 7.26 (d, J82 Hz, 1H), 7.16 (s, 1H), 7.06-7.09 (m, 1H), 4.33 (s, 2H), 3.52 (s, 2H), 2.87-2.89 (m, 1H), 1.01-1.11 (m, 2H), 0.79-0.81 (m, 4).

Molecular formula: CH$_{15}$H$_{17}$FN$_2$O$_2$ Molecular weight: 276.31 LC-MS (Pos, m/z)=277.2 [M+H]$^+$.

Example 25: Synthesis of (E)-5-((2-(aminomethyl)-3-fluoroallyl)oxy)-2-cyclopropyl isoindolin-1,3-dione (compound 30) hydrochloride

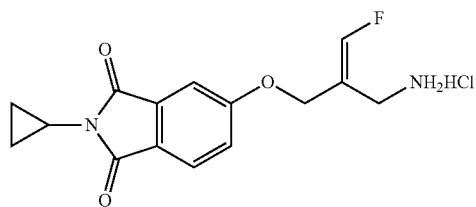

Flow chart:

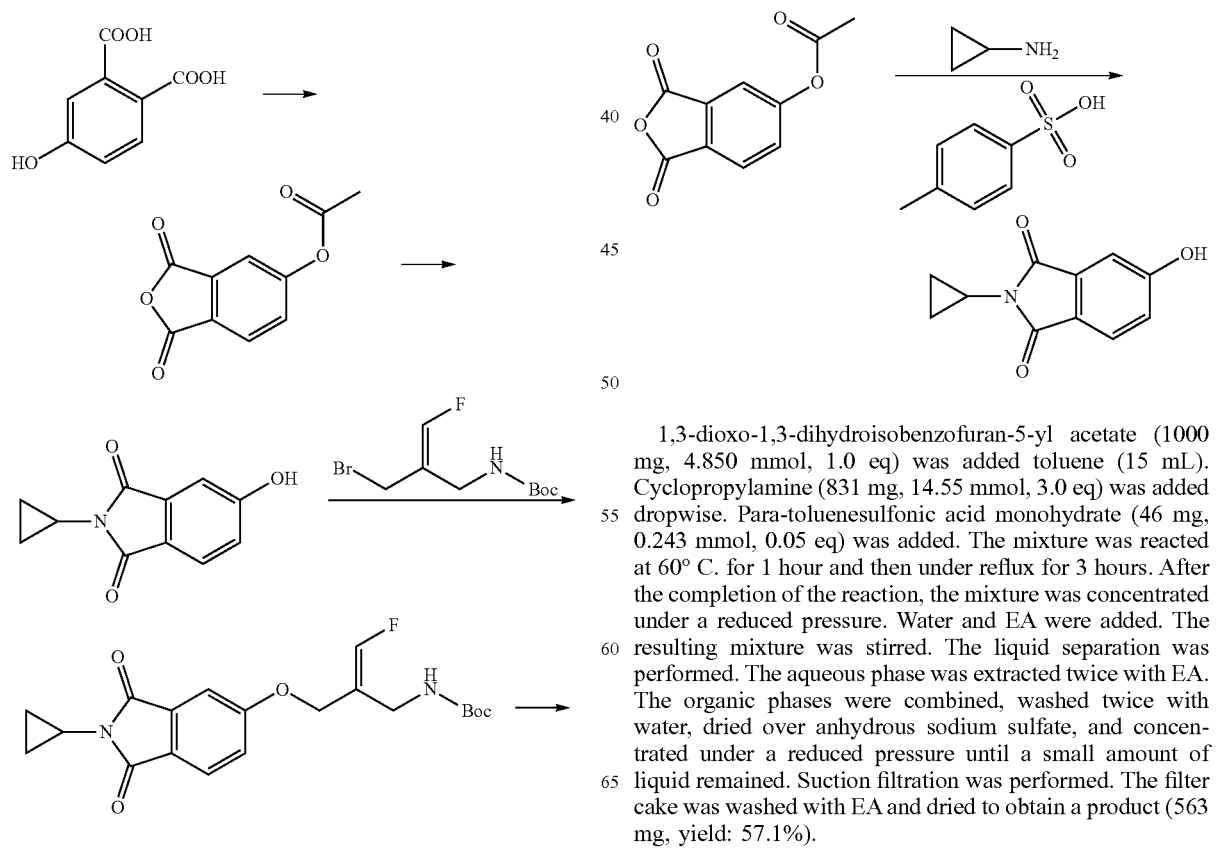

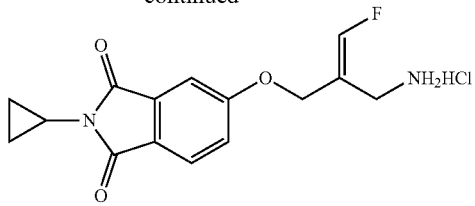

4-hydroxyphthalic acid (5 g, 27.5 mmol, 1.0 eq) and acetic anhydride (23 mL) were mixed. Under the nitrogen protection, the mixture was kept under reflux overnight, and then concentrated under a reduced pressure to remove acetic anhydride to obtain a solid. The solid was washed with PE. Suction filtration was performed to obtain a light brown solid product (4.8 g, yield: 84.8%), which was directly used in the next step reaction without purification.

Step 2: Synthesis of 2-cyclopropyl-5-hydroxyisoindolin-1,3-dione

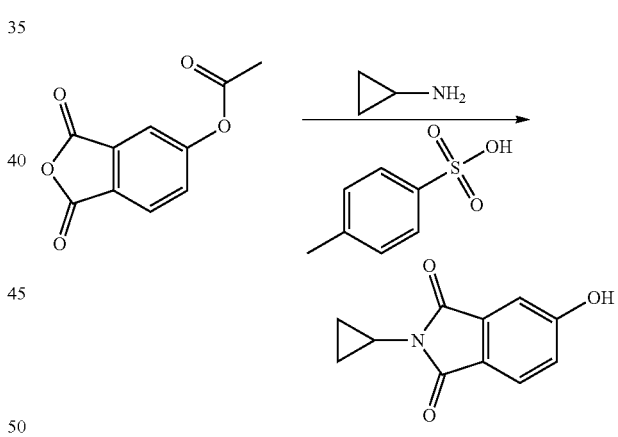

1,3-dioxo-1,3-dihydroisobenzofuran-5-yl acetate (1000 mg, 4.850 mmol, 1.0 eq) was added toluene (15 mL). Cyclopropylamine (831 mg, 14.55 mmol, 3.0 eq) was added dropwise. Para-toluenesulfonic acid monohydrate (46 mg, 0.243 mmol, 0.05 eq) was added. The mixture was reacted at 60° C. for 1 hour and then under reflux for 3 hours. After the completion of the reaction, the mixture was concentrated under a reduced pressure. Water and EA were added. The resulting mixture was stirred. The liquid separation was performed. The aqueous phase was extracted twice with EA. The organic phases were combined, washed twice with water, dried over anhydrous sodium sulfate, and concentrated under a reduced pressure until a small amount of liquid remained. Suction filtration was performed. The filter cake was washed with EA and dried to obtain a product (563 mg, yield: 57.1%).

Step 3: Synthesis of (h)-tert-butyl (2-(((2-cyclopropyl-1,3-dioxoisoindolin-5-yl)oxy)methyl)-3-fluoroallylcarbamate

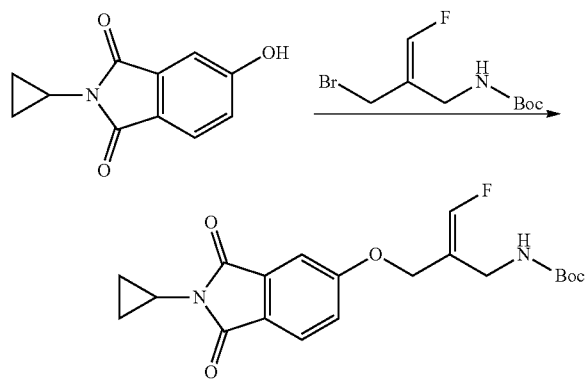

A raw material 2-cyclopropyl-5-hydroxyisoindolin-1,3-dione (150 mg, 0.738 mmol, 1.0 eq) and (E)-tert-butyl (2-(bromomethyl)-3-fluoroallyl)carbamate (198 mg, 0.738 mmol, 1.0 eq) were dissolved in DMF (4 mL). K$_2$CO$_3$ (153 mg, 1.107 mmol, 1.5 eq) was added. The reaction was performed under being stirred at room temperature overnight. After the completion of the reaction indicated by TLC detection, water was added. The mixture was extracted with EA. The organic phase was washed with water, dried over anhydrous sodium sulfate, and concentrated to obtain a crude product, which was separated by preparative thin layer chromatography (PE:EA=1:1) to obtain a product (249 mg, yield: 86.5%).

Step 4: Synthesis of (E)-5-((2-(aminomethyl)-3-fluoroallyl)oxy)-2-cyclopropyl isoindolin-1,3-dione hydrochloride

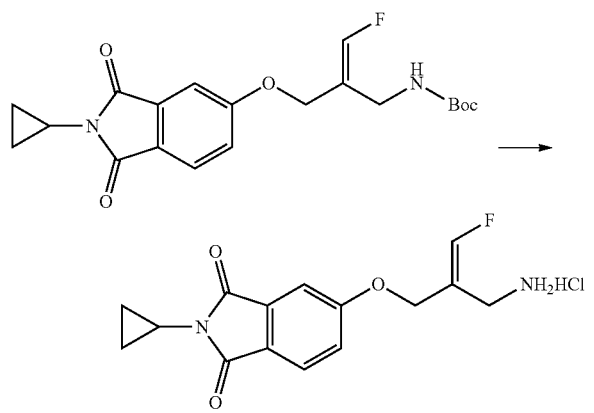

Intermediate (E)-tert-butyl (2-(((2-cyclopropyl-1,3-dioxoisoindolin-5-yl)oxy)methyl)-3-fluoroallylcarbamate (249 mg, 0.638 mmol, 1.0 eq) was dissolved in ethanol (4 mL). Hydrogen chloride ethanol solution (2 mL) was added. The mixture was stirred for 12 hours. A solid was separated out. Suction filtration was performed. The filter cake was washed with MTBE and dried to obtain a white solid product (133 mg, yield: 63.9%).

$^1$H NMR (400 MHz, DMSO-d$_6$) δ(ppm): 8.38 (brs, 3H), 7.77-7.79 (d, J=8.2 Hz, 1H), 7.42 (s, 1H), 7.35 (d, J=82 Hz, 1H), 7.35-7.38 (m, 1H), 4.83-4.84 (d, 2H), 3.61 (s, 2H), 2.62-2.67 (m, 1H), 0.85-0.91 (m, 4H).

Molecular formula: C$_{15}$H$_{15}$FN$_2$O$_3$ Molecular weight: 290.29 LC-MS (Pos, m/z)=291.1[M+H]$^+$.

Example 26: Synthesis of (Z)-5-((2-(aminomethyl)-3-fluoroallyl)oxy)-2-cyclopropylisoindolin-1,3-dione (compound 31) hydrochloride

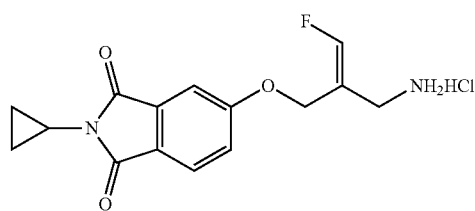

Step 1: Synthesis of (Z)-tert-butyl (2-(((2-cyclopropyl-1,3-dioxoisoindolin-5-yl)oxy)methyl)-3-fluoroallyl)carbamate

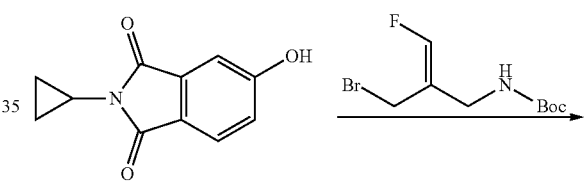

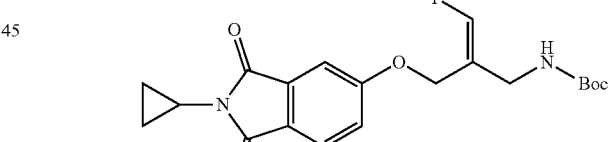

2-cyclopropyl-5-hydroxyisoindolin-1,3-dione (150.0 mg, 0.74 mmol, 1.0 eq) and (Z)-tert-butyl (2-(bromomethyl)-3-fluoroallyl)carbamate (238.6 trig, 0.89 mmol, 1.2 eq) were dissolved in DMF. K$_2$CO$_3$ (153.4 mg, 1.11 mmol, 1.5 eq) was added. The mixture was stirred at room temperature for 6 hours. After the completion of the reaction indicated by TLC detection, water (10 mL) and EA (10 mL) were added. The mixture was stirred. The liquid separation was performed. The aqueous phase was extracted with EA (10 mL). The organic phases were combined, and washed with water for three times. The organic phase was dried and concentrated to obtain a crude product, which was purified by preparative thin layer chromatography (PE:EA=1:1) to obtain a product (206 mg yield: 71.3%).

Step 2: Synthesis of (Z)-5-((2-(aminomethyl)-3-fluoroally)oxy)-2-cyclopropylisoindolin-1,3-dione hydrochloride

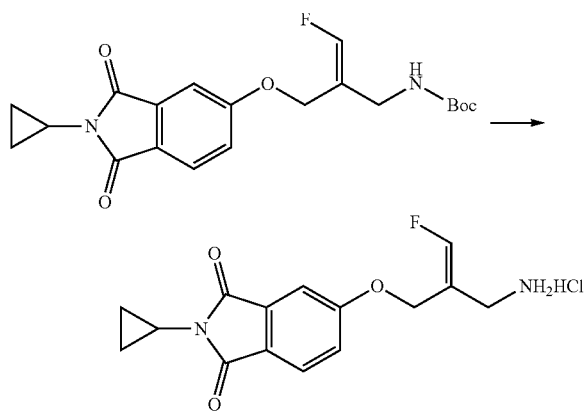

(Z)-tert-butyl (2-(((2-cyclopropyl-1,3-dioxoisoindolin-5-yl)oxy)methyl)-3-fluoroallyl)carbamate (206 mg, 0.53 mmol, 1.0 eq) was dissolved in EtOH. A solution of hydrogen chloride in ethanol (2 mL) was added. The mixture was stirred at room temperature for 4 hours. A solid was separated out. Suction filtration was performed to obtain a product (81.73 mg, yield: 47.2%).

$^1$H NMR (400 MHz, DMSO-$d_6$) δ(ppm): 8.23 (s, 3H), 7.74-7.79 (m, 1H), 7.31-7.44 (m, 2), 7.25 (m, J=84 Hz, 1H) 4.92 (m, 2H), 3.55 (s, 2H), 2.60-2.67 (m, 1H), 0.84-0.94 (m, 4H).

Molecular formula: $C_{15}H_{15}FN_2O_3$ Molecular weight: 290.29 LC-MS (Pos, m/z)=291.11 [M+H]$^+$.

Example 27: Synthesis of (Z)-6-((2-(aminomethyl)-3-fluoroallyl)oxy)-2-cyclopropyl-3,4-dihydro-2,7-naphthyridine-1(2H)-one (compound 32) trifluoroacetate

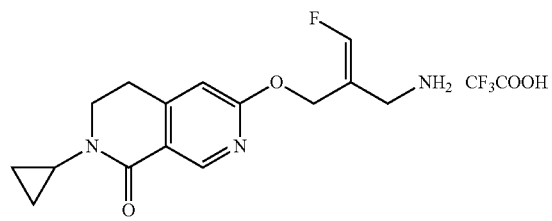 [SMILES: NC/C(=C/F)COc1cc2c(cn1)C(=O)N(C1CC1)CC2 ; "CF3COOH"]

Step 1: Synthesis of (Z)-tert-butyl (2-(((7-cyclopropyl-8-oxo-5,6,7,8-tetrahydro-2,7-naphthyridine-3-yl)oxy)methyl)-3-fluoroallyl)carbamate

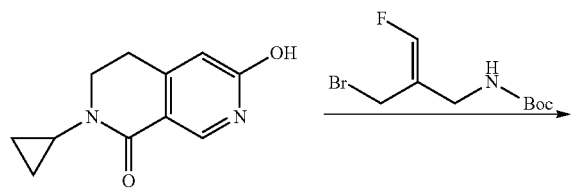

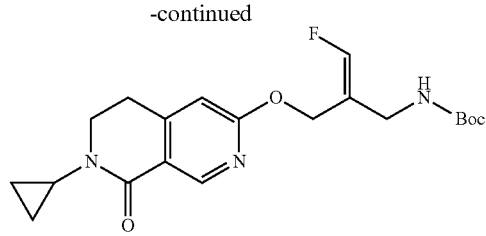

2-cyclopropyl-6-hydroxy-3,4-dihydro-2,7-naphthyridin-1(2H)-one (200 mg, 0.979 mmol, 1.0 eq) and (Z)-tert-butyl (2-(bromomethyl)-3-fluoroallyl)carbamate (315 mg, 1.175 mmol, 1.2 eq) were dissolved in toluene (4 mL). $Ag_2CO_3$ (351 mg, 1.273 mmol, 1.3 eq) was added. The mixture was stirred at 60° C. for 2 hours. After the completion of the reaction indicated by TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by preparative thin layer chromatography (PE:EA=1:1) to obtain a product (110 mg, yield: 28.7%).

Step 2: Synthesis of (Z)-6-((2-(aminomethyl)-3-fluoroallyl)oxy)-2-cyclopropyl-3,4-dihydro-2,7-naphthyridine-1(2H)-one trifluoroacetate

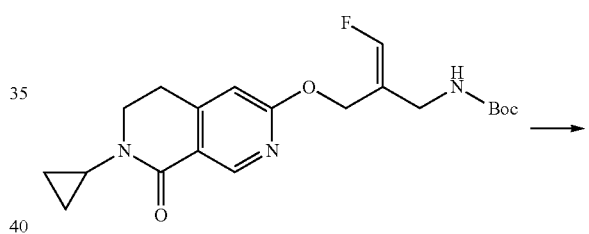

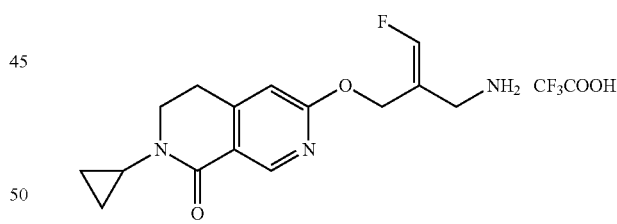

Intermediate (Z)-tert-butyl (2-(((7-cyclopropyl-8-oxo-5,6,7,8-tetrahydro-2,7-naphthyridine-3-yl)oxy)methyl)-3-fluoroallyl)carbamate (110 mg, 0.281 mmol, 1.0 eq) was dissolved in DCM (4 mL). $CF_3COOH$ (0.5 mL) was added. The mixture was stirred for 12 hours and concentrated to obtain a crude product, which was purified by preparative thin layer chromatography (DCM:MeOH=10:1) to obtain a product (83.5 mg, yield: 73.3%).

$^1$H NMR (400 MHz, DMSO-$d_6$) δ(ppm): 8.61 (s, 1H), 7.96 (brs, 3H), 7.09-7.29 (d, J=82 Hz, 1H), 6.78 (s, 1H), 4.98-4.99 (d, 2H), 3.55 (d, 2H), 3.45-3.54 (t, 2H), 2.91-2.94 (t, 2H), 2.79-2.85 (m, 1H), 0.70-0.86 (m, 4H).

Molecular formula: $C_{15}H_{18}FN_3O_2$ Molecular weight: 291.33 LC-MS (Pos, m/z)=292.2 [M+H]$^+$.

Example 28: Synthesis of (Z)-6-((2-(aminomethyl)-3-fluoroallyl)oxy)-2-cyclopropyl-1,2-dihydro-3H-pyrrolo-[3,4-c]pyridin-3-one (compound) 3 trifluoroacetate

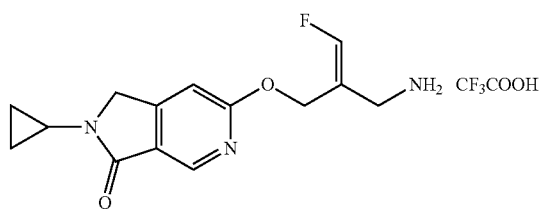 [SMILES: NC/C(=C/F)COc1cc2c(cn1)C(=O)N(C1CC1)C2 ; "CF3COOH"]

Step 1: Synthesis of (Z)-tert-butyl (2-(((2-cyclopropyl-3-oxo-2,3-dihydro-1H-pyrrolo[3,4-c]pyridin-6-yl)oxy)methyl)-3-fluoroallyl)carbamate

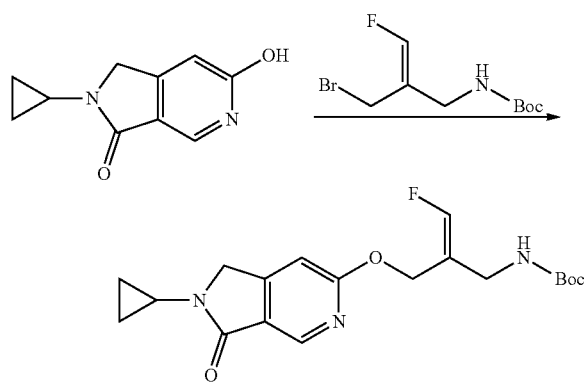

Intermediate 2-cyclopropyl-6-hydroxy-1,2-dihydro-3H-pyrrolo-[3,4-c]pyridin-3-one (500.0 mg, 2.63 mmol, 1.0 eq) and (Z)-tert-butyl (2-(bromomethyl)-3-fluoroallyl)carbamate (705.2 mg, 2.63 mmol, 1.0 eq) were dissolved in toluene. Ag$_2$CO$_3$ (1.089 g, 3.95 mmol, 1.5 eq) was added. The mixture was stirred at 60° C. for 4 hours. After the completion of the reaction indicated by TLC detection, a mixed solvent of DCM and MeOH (10:1, 50 mL) was added. The mixture was stirred. Suction filtration was performed. The filter cake was washed with MeOH (10 mL). The filtrate was concentrated to obtain a crude product, which was purified by silica gel column chromatography (PE:EA=5:1-1:1) to obtain a product (500 mg, yield 50.4%).

Step 2: Synthesis of (Z)-6-((2-(aminomethyl)-3-fluoroallyl)oxy)-2-cyclopropyl-1,2-dihydro-3H-pyrrolo-[3,4-c]pyridin-3-one trifluoroacetate

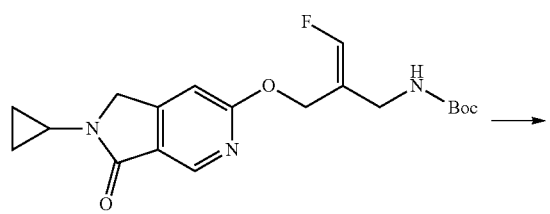

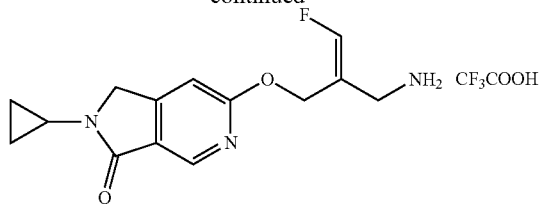

Intermediate (Z)-tert-butyl (2-(((2-cyclopropyl-3-oxo-2,3-dihydro-1H-pyrrolo[3,4-c]pyridin-6-yl)oxy)methyl)-3-fluoroallyl)carbamate (500 mg, 1.32 mmol, 1.0 eq) was dissolved in DCM. CF$_3$COOH (5 mL) was added. The mixture was stirred for 12 hours and concentrated to obtain a crude product, which was firstly purified by silica gel column chromatography (DM:MeOH=50:1-10:1), and then lyophilized to obtain a product (350 mg, yield 67.8%/).

$^1$H NMR (400 MHz, DMSO-d$_6$) δ(ppm): 8.50 (s, 1H), 8.08 (s, 3H), 7.21 (d, J=84 Hz, 1H), 7.03 (s, 1H), 5.01 (d, 2H), 4.42 (s, 2H), 3.57 (s, 2H), 2.86-2.91 (m, 1H), 0.78-0.83 (m, 4H).

Molecular formula: C$_{14}$H$_{16}$FN$_3$O$_2$ Molecular weight: 277.30 LC-MS (Pos, m/z)=278.19 [M+H]$^+$.

Example 29: Synthesis of (Z)-6-((2-(aminomethyl)-3-fluoroallyl)oxy)-2-cyclopropyl-3,4-dihydroisoquinolin-1(2H)-one (compound 34) hydrochloride

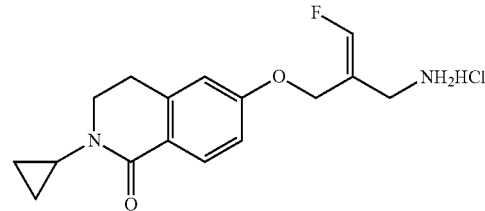

Step 1: Synthesis of (Z)-tert-butyl (2-(((2-cyclopropyl-1-oxo-1,2,3,4-tetrahydroisoquinolin-6-yl)oxy)methyl)-3-fluoroallyl)carbamate

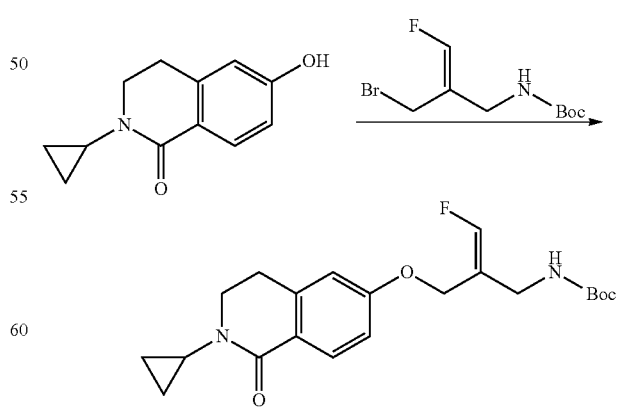

2-cyclopropyl-6-hydroxy-3,4-dihydroisoquinolin-1(2H)-one (200.0 mg, 0.98 mmol, 1.0 eq) and (Z)-tert-butyl (2-(bromomethyl)-3-fluoroallyl)carbamate (316.7 mg, 1.18 mmol, 1.2 eq) were dissolved in DMF. K$_2$CO$_3$ (204.0 mg, 1.48 mmol, 1.5 eq) was added. The mixture was stirred at room temperature for 6 hours. After the completion of the reaction indicated by TLC detection, water (10 mL) and EA (10 mL) were added. The mixture was stirred. The liquid separation was performed. The aqueous phase was extracted with EA (10 mL). The organic phases were combined, and washed with water for three times. The organic phase was dried and concentrated to obtain a crude product, which was purified by preparative thin layer chromatography (PE: EA=1:1) to obtain a product (350 mg, yield: 91.1%).

Step 2: Synthesis of (Z)-6-((2-(aminomethyl)-3-fluoroallyl)oxy)-2-cyclopropyl-3,4-dihydroisoquinolin-1(2H-1)-one hydrochloride

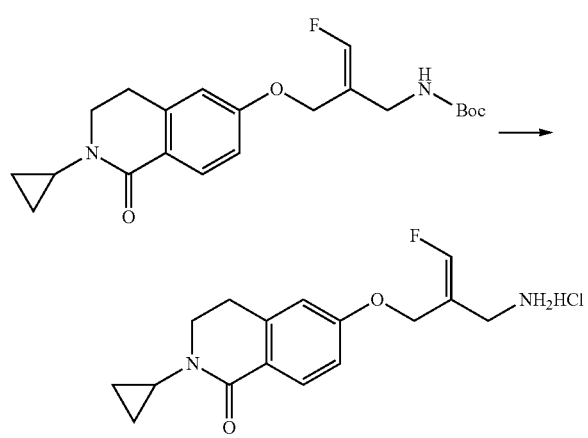

Intermediate (Z)-tert-butyl (2-(((2-cyclopropyl-1-oxo-1,2,3,4-tetrahydroisoquinolin-6-yl)oxy)methyl)-3-fluoroallyl) carbamate (350 mg, 0.89 mmol, 1.0 eq) was dissolved in EtOH. A solution of hydrogen chloride in ethanol (2 mL) was added. The mixture was stirred at room temperature for 4 hours, and concentrated. DCM (3 mL) and MTBE (5 mL) were added, and the resulting mixture was concentrated. A solid was separated out. Suction filtration was performed to obtain a product (206 mg, yield: 70.8%).

$^1$H NMR (400 MHz, DMSO-d$_6$) δ(ppm): 8.27 (s, 31), 7.81-7.83 (d, 1H), 7.23 (d, J=84 Hz, 1H), 6.90-6.96 (n, 2H), 4.78-4.79 (d, 2H), 3.43-3.52 (m, 41), 2.83-2.90 (m, 2H), 2.77-2.83 (m, 1H), 0.63-0.78 (m, 4H).

Molecular formula: C$_{16}$H$_{19}$FN$_2$O$_2$ Molecular weight: 290.34 LC-MS (Pos, m/z)=291.23 [M+H]$^+$.

Example 30: Synthesis of (E)-6-((2-(aminomethyl)-3-fluoroallyl)oxy)-2-cyclopropyl-1,2-dihydro-3H-pyrrolo-[3,4-c]pyridin-3-one (compound 21) hydrochloride

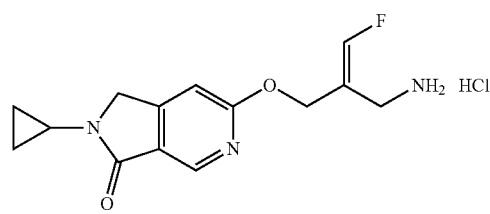 [SMILES: NC/C(=C\F)COc1cc2c(cn1)C(=O)N(C1CC1)C2 ; Cl]

Step 1: Synthesis of (E)-6-((2-(aminoethyl)-3-fluoroallyl)oxy)-2-cyclopropyl-1,2-dihydro-3H-pyrrolo-[3,4-c]pyridin-3-one hydrochloride

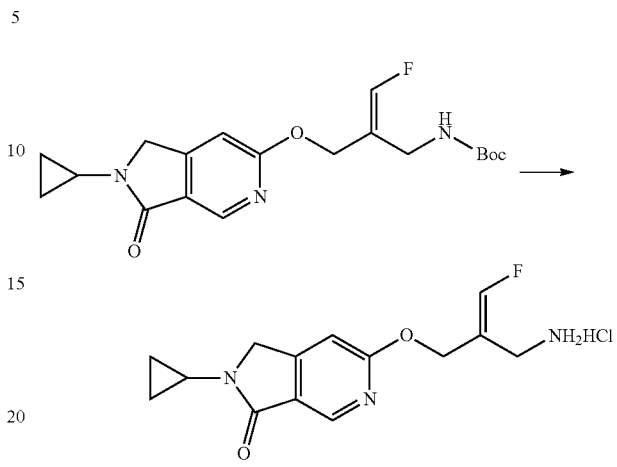

(E)-tert-butyl (2-((2-cyclopropyl-3-oxo-2,3-dihydro-1H-pyrrolo[3,4-c]pyridin-6-yl)oxy)methyl)-3-fluoroallyl)carbamate (59.0 mug, 0.16 mmol, 1.0 eq) was dissolved in EtOH. Hydrogen chloride ethanol solution (0.5 mL) was added. The mixture was stirred for 5 hours and concentrated. MTBE was added. A solid was separated out. Suction filtration was performed to obtain a product (E)-6-((2-(aminomethyl)-3-fluoroallyl)oxy)-2-cyclopropyl-1,2-dihydro-3H-pyrrolo-[3,4-c]pyridin-3-one hydrochloride (13.6 mg, yield: 28.4%).

$^1$H NMR (400 MHz, DMSO-d$_6$) δ(ppm): 8.49 (s, 1H), 8.37 (s, 3H), 7.34 (d, J=84 Hz, 1H), 7.04 (m, 1H), 4.93 (s, 2H), 4.42 (s, 2H), 3.60 (m, 2), 2.89 (m, 1H), 0.78-0.82 (m, 4H).

Molecular formula: C$_{14}$H$_{16}$FN$_3$O$_2$ Molecular weight: 277.30 LC-MS (Pos, m/z)=278.16 [M+H]$^+$.

Example 31: Synthesis of (E)-6-((2-(aminomethyl)-3-fluoroallyl)oxy)-2-cyclopropyl-3,4-dihydroisoquinolin-1(2H)-one (Compound 5)

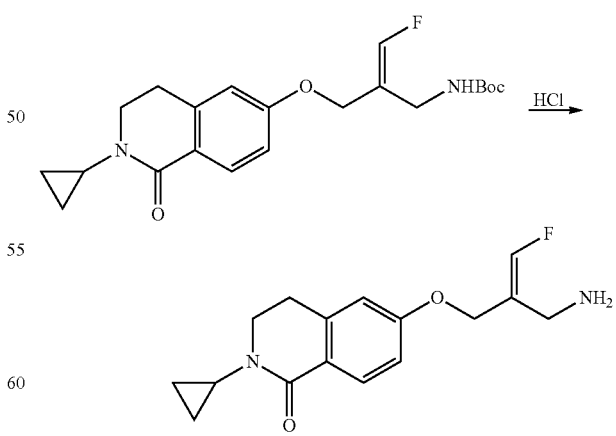

(E)-tert-butyl (2-(((2-cyclopropyl-1-oxo-1,2,3,4-tetrahydroisoquinolin-6-yl)oxy)methyl)-3-fluoroallyl)carbamate (29.5 mg, 0.0756 mmol, 1 eq), which was obtained in Step (1) of Example 6, was dissolved in ethanol (2 mL). Hydrogen chloride ethanol solution (2 mL) was added. The mixture was reacted at room temperature for 3 hours. After the completion of the reaction indicated by LC-MS detection, the solution was directly concentrated. An aqueous saturated sodium bicarbonate solution (2 mL) was added. The mixture was extracted with dichoromethane/methanol (10/1) (5 mL×4). The organic phases were combined, dried over anhydrous sodium sulfate, and filtered. The filtrate was concentrated under a reduced pressure to obtain a crude product, which was purified by silica gel column chromatography (DCM:MeOH=10:1) to obtain a product (12 mg, yield: 49%).

$^1$HNMR (400 MHz, DMSO-d$_6$) δ(ppm): 7.79-7.81 (d, 1H), 6.98 (d, J=88 Hz, 1H), 6.90-6.93 (dd, 1H), 6.88 (s, 1H), 4.60-4.61 (d, 2H), 3.42-3.46 (t, 2I), 3.31 (s, 2H), 2.87-290 (t, 2H), 2.77-2.83 (m, 1H), 1.56 (brs, 2H), 0.75-0.78 (m, 2H), 0.66-0.72 (m, 2H)

Molecular formula: C$_{16}$H$_{19}$FN$_2$O$_2$ Molecular weight: 290.14 LC-MS (Pos, m/z)=291.2[M+H]$^+$.

Example 32: Synthesis of (Z)-2-((2-(aminomethyl)-3-fluoroallyl)oxy)-6-cyclopropyl-7,8-dihydro-1,6-naphthyridin-5(6H-one (compound 23)

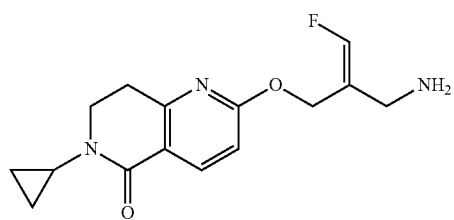 [SMILES: NC/C(=C/F)COc1ccc2c(n1)CCN(C1CC1)C2=O]

Step 1: Synthesis of (Z)-2-((2-(aminomethyl)-3-fluoroallyl)oxy)-6-cyclopropyl-7,8-dihydro-1,6-naphthyridin-5(6H)-one

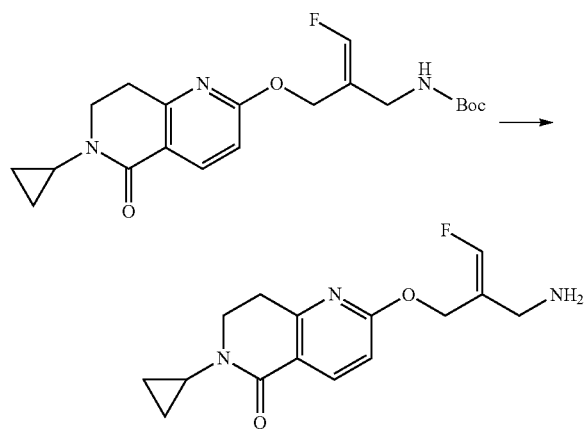

A raw material tert-butyl (2-(((6-cyclopropyl-5-oxo-5,6,7,8-tetrahydro-1,6-naphthyridin-2-yl)oxy)methyl)-3-fluoroallyl)carbamate (280.0 mg, 0.72 mmol, 1.0 eq) was dissolved in DCM. CF$_3$COOH (2 mL) was added. The mixture was stirred for 12 hours and concentrated to obtain a crude product, which was firstly purified by preparative thin layer chromatography (DCM:MeOH=10:1) to obtain a cis-trans mixture (224.0 mg), which then was separated by preparative thin layer chromatography (DCM:Et$_3$N=98.5:1.5). Water (2 mL) was added. The resulting mixture was extracted with DCM:MeOH (10:1, 30 mL) to obtain a product (6.19 mg, yield: 2.95%).

$^1$H NMR (400 MHz, DMSO-d$_6$) δ(ppm): 8.10-8.13 (m, 1H), 7.20 (d, J=84 Hz, 1H), 6.82-6.84 (m, 1H), 4.98-4.99 (d, 2H), 3.52-3.56 (m, 4H), 2.96-2.99 (m, 2H), 2.79-2.82 (m, 1H), 0.77-0.79 (m, 2H), 0.68-0.69 (m, 2H).

Molecular formula: C$_{15}$H$_{18}$FN$_3$O$_2$ Molecular weight: 291.33 LC-MS (Pos, m/z)=292.25 [M+H]$^+$ In the following biological examples of the present invention, the dosage was converted to be based on the compound in free form.

Biological Example 1: Determination of the Inhibition Activity of the Compound on rhVAP-1 and MAO-A/B Test substances: the compounds of the present invention shown in Table 1 and prepared according to the methods of the examples 1. Inhibition Activity of the Compounds on the rhVAP-1 Enzyme (1) Instrument, consumable and reagent Multifunctional microplate reader (MD, FlexStation 3), black bottom-impermeable 96-well plate (Corning), rhVAP-1 (PeproTech)

(2) Preparation of Compound Concentration Gradient Solutions

An appropriate amount of the test compound was dissolved in DMSO to 10 mM and stored. Before the experiment, an appropriate amount of 10 mM test compound mother liquor was diluted to 10 μM solution with DMSO. Then 3-fold gradient dilution with DMSO was performed, and 10 concentration gradients were formed.

(3) Preparation of Enzyme Solutions

An appropriate amount of protein diluent was added to the rhVAP-1 powder to obtain 1 mg/mL of the mother liquor for storage. Before the experiment, the dilution with PBS provided a 4×concentration of the enzyme solution.

(4) Preparation of 2×Concentration Substrate Mixed Solution

An appropriate amount of benzylamine was added to PBS and dissolved to obtain 200 mM of the benzylamine solution. 2 mM Amplex Red mother liquor and 500 U/mL HRP mother liquor were added. The dilution with PBS provided 2×concentration substrate mixed solution.

(5) Test Method

First, 10 μL of compound solutions of different concentrations, 25 μL of 4×rhVAP-1 enzyme solution and 15 μL of PBS were added to a 96-well plate, evenly mixed by oscillation, and incubated at 37° C. for 30 minutes. Then 50 μL of 2×substrate mixed solution was added to each well, and immediately the detection was performed with the microplate reader in a condition of an exciting light at 565 nm, an emitting light at 590 nm, the fluorescence intensity for detecting each well of 5 minutes/run, and a total detection time of 25 minutes. The inhibition rate was calculated according to the following formula:

$$V(RFU/min)=(Ft(RFU)-F0(RFU))/(Time(min))$$

Inhibition rate (%)=100%−Vcmpd(RFU/min)/V max (RFU/min)×100%

V: the fluorescence change rate; Ft: fluorescence reading at the time point t; F0: fluorescence reading at the time point 0; Time: time period t; Vcmpd: the fluorescence change rate of the test compound; Vmax: the Max well fluorescence change rate.

(6) Fitted Dose-Effect Curve

The log values of the concentrations were taken as the X-axis and the percent inhibition rates were taken as the Y-axis, and the dose-effect curve was fitted using the log (inhibitor) vs. response-Variable slope of the analytical software GraphPad Prism 5 to obtain the $IC_{50}$ value of each compound for enzyme activity.

2. Selectivity of the Compounds for MAO-A/B Enzymes (1) Instrument, Consumable and Reagent Microplate reader (Perkin Elmer, Envision), 384 well plates (Perkin Elmer), centrifuge (Eppendorf), MAO-Glo™ (Promega), MAO-A (Active Motif) and MAO-B (Active Motif).

(2) Preparation of Compound Concentration Gradient Solutions

An appropriate amount of the test compound was dissolved in DMSO to 10 mM and stored. Before the experiment, an appropriate amount of 10 mM test compound mother liquor was diluted to 100 μM solution with DMSO. Then 4-fold gradient dilution with DMSO was performed, and 6 concentration gradients were formed.

(3) Preparation of Enzyme Solutions

The MAO-A/B mother liquor was diluted to 2×concentration enzyme solution with the assay buffer solution for the MAO-A/B.

(4) Preparation of 2×Concentration Substrate Mixed Solution

The mother liquor of the MAO-A/B substrate mixed solution was diluted to 2×concentration substrate mixed solution with the assay buffer solution for the MAO-A/B.

(5) Test Method 200 nL of compound solutions of different concentrations or solvent
and 10 μL of 2×MAO-A/B enzyme solution were added to a 384-well plate, evenly mixed by oscillation, and incubated at 37° C. for 60 minutes. Then 10 μL of 2×substrate mixed solution was added to each well, and immediately the detection was performed with the microplate reader in a condition of an exciting light at 535 nm, an emitting light at 587 nm, the fluorescence intensity for detecting each well of 5 minutes/run, and a total detection time of 25 minutes.

The inhibition rate was calculated according to the following formula:

$$V(RFU/\text{min}) = (Ft(RFU) - F0(RFU))/(\text{Time(min)})$$

Inhibition rate (%) = 100% − Vcmpd(RFU/min)/V max (RFU/min) × 100%

V: the fluorescence change rate; Ft: fluorescence reading at the time point t; F0: fluorescence reading at the time point 0; Time: time period t; Vcmpd: the fluorescence change rate of the test compound; Vmax: the Max well fluorescence change rate.

(6) Fitted Dose-Effect Curve

The log values of the concentrations were taken as the X-axis and the percent inhibition rates were taken as the Y-axis, and the dose-effect curve was fitted using the log (inhibitor) vs. response-Variable slope of the analytical software GraphPad Prism 5 to obtain the $IC_{50}$ value of each compound for enzyme activity.

3. Test Results

TABLE 1

| Test Compound | rhVAP-1 Enzyme $IC_{50}$ (nM) | MAO-B $IC_{50}$ (nM) | MAO-A $IC_{50}$ (nM) |
|---|---|---|---|
| Trifluoroacetate of Compound 4 | 59 | — | — |
| Hydrochloride of Compound 5 | 18 | 6300 | 1300 |
| Hydrochloride of Compound 8 | 30 | >100000 | — |
| Hydrochloride of Compound 16 | 24 | 2800 | — |
| Hydrochloride of Compound 19 | 21 | — | — |
| Hydrochloride of Compound 21 | 21 | 14000 | >100000 |
| Trifluoroacetate of Compound 23 | 14 | 19000 | 10000 |
| Trifluoroacetate of Compound 24 | 24 | 37000 | — |
| Trifluoroacetate of Compound 25 | 25 | 13000 | — |
| Trifluoroacetate of Compound 26 | 51 | 8800 | — |
| Hydrochloride of Compound 27 | 16 | 38000 | — |
| Hydrochloride of Compound 28 | 14 | 20000 | — |
| Hydrochloride of Compound 29 | 25 | 4100 | — |
| Hydrochloride of Compound 30 | 32 | 5800 | — |
| Hydrochloride of Compound 31 | 11 | — | — |
| Trifluoroacetate of Compound 32 | 11 | 6600 | — |
| Trifluoroacetate of Compound 33 | 14 | 8600 | — |
| Hydrochloride of Compound 34 | 6 | 8400 | — |

"—" represented "not tested".

As can be seen from the above table, the compounds of the present invention showed excellent inhibition activity on rhVAP-1 enzyme, which indicated that they can be applied to the prevention and/or treatment of diseases associated with elevated expression or increased activity of VAP-1 enzyme. Also, the compounds of the present invention exhibited excellent specific selectivity for SSAO/VAP-1 enzyme over monoamine oxidase (MAO).

Biological Example 2: In Vitro Stability Test of the Compound of the Present Invention in the Dog Plasma Preparation of the Working Solution:

Test compound: about 2 mg of test compound was prepared with DMSO into a 5 mM stock solution, then diluted with DMSO to 1 mM solution, and finally diluted with water to 50 μM test compound working solution for use.

Termination solution: about 2 mg of tolbutamide compound was firstly prepared with DMSO into a 1 mg/mL stock solution, finally diluted with acetonitrile to 100 ng/mL termination solution, and stored at 4° C. for later use.

Test Steps:

(1) Frozen Beagle dog plasma was pre-incubated and thawed in a 37° C. water bath constant temperature oscillator for use.

(2) 10 μL of test compound (10 μM) was added to 490M (Beagle dog plasma, final concentration of the test substance was 0.2 μM, two duplicate samples.

(3) The sample was evenly mixed in vortex and incubated in a 37° C. water bath constant temperature oscillator.

(4) At the corresponding time points (T=0 h, 0.5 h, 1 h, 2 h; sample at 0 h was not incubated), 400 μL of the termination solution was added to 40 μL of the reaction solution obtained by reacting the test compound of step (2) and the components in the blood plasma, and the resulting mixture was evenly mixed and frozen at −80° C. for storage.

(5) After the incubation experiment was completed, the samples in the sample tubes at different time points are thawed, evenly mixed and centrifuged at 12000 rpm for 5 minutes in a 4° C. centrifuge.

(6) 150 μL of water was added into a 96-well sample plate, and 50 μL of the supernatant was added into the sample well. The resulting mixture was evenly mixed, and then the LC-MS/MS sample analysis was performed.

Data Analysis:

Calculation formula is as follows: retention rate (%)=$C_{Tn}/C_{T0}$ wherein, $C_{Tn}$ is the measurement concentration of the compound in the final solution after each incubation time point, n=0.5 h, 1 h, 2 h; $C_{T0}$ is the measurement concentration of the compound in the final solution at the initial incubation.

Results:

TABLE 2 plasma stability for the compound of the present invention (2 hours)

| Compound | Retention Rate |
| --- | --- |
| Hydrochloride of Compound 5 | 98.6% |

As can be seen from Table 2, the compound of the present invention showed an excellent plasma stability.

Biological Example 3: Stability Test of the Compounds of the Present Invention in Human Liver Microsome The composition of the incubation system:

| Substance to be added | Initial Concentration | Proportion (%) | Concentration |
| --- | --- | --- | --- |
| Phosphate buffer | 100 mM | 50 | 50 mM |
| MgCl$_2$ | 20 mM | 5 | 1 mM |
| liver microsome | 20 mg protein/mL | 2.5 | 0.5 mg protein/mL |
| Water needed to be supplemented | — | 22.5 | — |
| Compound | 10 μM | 10 | 1 μM |
| β-NADPH | 10 mM | 10 | 1 mM |

Test Steps:

(1) The liver microsome (20 mg protein/mL) was removed from the −80° C. refrigerator, pre-incubated in a 37° C. water bath constant temperature oscillator for 3 minutes, and thawed for use.

(2) A mixed solution of the incubation system (excluding compound and β-NADPH) according to the above "composition of the incubation system" for the test was prepared, and pre-incubated in a 37° C. water bath constant temperature oscillator for 2 minutes.

(3) Control group (excluding β-NADPH): 30 μL of water and 30 μL of compound working solution (concentration: 10 μM) were added to 240 μL of the mixed solution of the incubation system of step (2), and vortexed for 30 seconds to mix well. The total reaction volume was 300 μL. A duplicate sample was prepared. The sample was incubated in a 37° water bath constant temperature oscillator. The timing began and the sampling time points were set at 0 minute and 60 minutes.

(4) Sample group: 70 μL β-NADPH solution (10 mM) and 70 μL compound working solution (concentration: 10 μM) were added to 560 μL of the mixed solution in step (2). The total reaction volume was 700 μL. The resulting mixture was vortexed for 30 seconds to mix well. A duplicate sample was prepared. The sample was incubated in a 37° C. water bath constant temperature oscillator. The timing began and the sampling time points were set at 0 minute, 5 minutes, 10 minutes, 20 minutes, 30 minutes, and 60 minutes after timing.

(5) After vortexing for 3 minutes, the sample was centrifuged at 12000 rpm for 5 minutes.

(6) 150 μL of water was added to 50 μL of the supernatant. The resulting mixture was evenly mixed in vortex, and the sample LC/MS/MS analysis was performed.

(7) Data analysis and calculation provided the clearance $Cl_H$ and the result was shown in Table 3.

Results

TABLE 3

Stability test of the compounds of the present invention in human liver microsome

| Compound | $Cl_H$ (mL/min/kg) |
| --- | --- |
| Hydrochloride of Compound 5 | 4.63 |
| Hydrochloride of Compound 16 | 0.18 |
| Hydrochloride of Compound 19 | →0 |
| Hydrochloride of Compound 21 | 4.95 |
| Compound 22 | 2.94 |
| Compound 23 | 4.63 |
| Trifluoroacetate of Compound 24 | →0 |
| Hydrochloride of Compound 28 | →0 |
| Hydrochloride of Compound 29 | 4.18 |

As can be seen from table 3, the results of liver clearance of the compounds of the present invention were excellent, which indicated that the compounds of the present invention had excellent metabolic stability in vivo.

Biological example 4: Time-dependent inhibition assay for the rhVAP-1 enzyme

After incubation of the test substances at corresponding time intervals according to Table 4, the activity was measured at each time point in the same manner as in the rhVAP-1 enzymatic test method of biological example 1.

Specifically, 10 μL of compound solutions of different concentrations or solvent, 25 μL of 4×rhVAP-1 enzyme solution and 15 μL of PBS were added to a 96-well plate, evenly mixed by oscillation, and incubated at 37° C. for 0 minutes, 3 minutes, 6 minutes, 9 minutes and 12 minutes. Then 50 μL of 2×substrate mixed solution was added to each well, and immediately the detection was performed with the microplate reader in a condition of an exciting light at 565 nm, an emitting light at 590 nm, the fluorescence intensity for detecting each well of 5 minutes/run, and a total detection time of 25 minutes.

TABLE 4

Determination of the activity of the compound of the present invention at different time points

| Test Compound | IC$_{50}$(nM) | | | | |
|---|---|---|---|---|---|
| | 0 minute | 3 minutes | 6 minutes | 9 minutes | 12 minutes |
| Trifluoroacetate of Compound 23 | 205.9 | 18.58 | 15.19 | 13.99 | 12.55 |

The experiment result showed that the compound of the present invention was combined with the rhVAP-1 enzyme more quickly and had stronger affinity at 0 minute, thereby being beneficial to exert the inhibition effect more quickly. The IC$_{50}$ value gradually decreased with the increasing pre-incubation time and then stabilized. The compound of the present invention was shown to have potential irreversible inhibition activity on the rhVAP-1 enzyme and be time-dependent.

INDUSTRIAL APPLICABILITY

The haloallylamine compound of the present invention can be used for preventing and/or treating the SSAO/VAP-1 protein-related or SSAO/VAP-1 protein-mediated disease, and the compound of the present invention exhibits an excellent specific selectivity for the SSAO/VAP-1 enzyme.

The invention claimed is:

1. A compound represented by formula I, a pharmaceutically acceptable salt or a stereoisomer thereof:

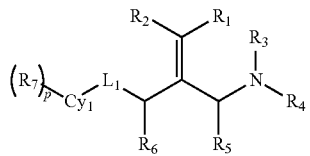

I wherein, $R_1$ and $R_2$ are each independently selected from hydrogen and halogen, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is a bond, or —CR'R"—, —N—, —O—, —S—, —SO$_2$—, S(O), —SONR'—, —SO$_2$NR'—, or —NR'CONR', R' and R" are each independently selected from hydrogen or $C_{1-6}$ alkyl;

$C_{y1}$ is the following formula i optionally substituted with a substituent:

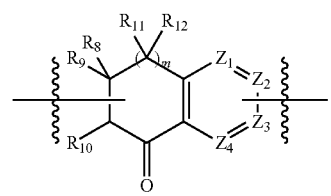

i wherein, $Z_1$, $Z_2$, $Z_3$ and $Z_4$ are each independently selected from CH or N, $R_8$ and $R_9$ are each independently selected from hydrogen, hydroxy, amino, carboxyl, cyano, nitro, halogen atom, $C_{1-6}$alkyl, $C_{1-6}$alkoxyl, $C_{1-6}$alkoxylC$_{1-6}$alkoxyl, $C_{1-6}$alkylamino, (C$_{1-6}$alkyl)$_2$amino, $C_{1-6}$alkylcarbonylamino, $C_{1-6}$alkylsulfonylamino, haloC$_{1-6}$alkyl, haloC$_{1-6}$alkoxyl, $C_{1-6}$alkylsulfonyl, $C_{1-6}$alkylthio, 3-8-membered cycloalkyl, aryl, 4-6-membered heterocyclyl, or 5-10-membered heteroaryl, or, optionally $R_8$ and $R_9$ form a 3-6 membered cycloalkyl with the atom to which they are attached, $R_{10}$ is selected from hydrogen, hydroxy, cyano, halogen atom, $C_{1-6}$alkyl, $C_{1-6}$alkoxyl, $C_{1-6}$alkoxylC$_{1-6}$alkoxyl, $C_{1-6}$alkylamino, (C$_{1-6}$alkyl)$_2$amino, $C_{1-6}$alkylcarbonylamino, $C_{1-6}$alkylsulfonylamino, haloC$_{1-6}$alkyl, haloC$_{1-6}$alkoxyl, $C_{1-6}$alkylsulfonyl, $C_{1-6}$alkylthio, 3-8-membered cycloalkyl, aryl, 4-6-membered heterocyclyl, or 5-10-membered heteroaryl, $R_{11}$ and $R_{12}$ are each hydrogen, m is 0 or 1;

p is 1, $R_7$ is each independently selected from hydrogen, hydroxy, amino, carboxyl, cyano, nitro, halogen atom, $C_{1-6}$alkyl,

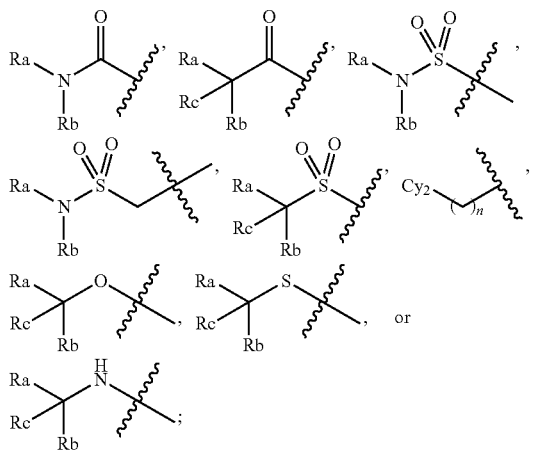

$R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 3-12-membered heterocyclyl optionally substituted with a substituent, or 5-10-membered heteroaryl optionally substituted with a substituent, or, optionally $R_a$ and $R_b$ form a 3-8 membered ring with the atom to which they are attached; $C_{y2}$ is aryl optionally substituted with a substituent, 3-12-membered heterocyclyl optionally substituted with a substituent, or 5-10-membered heteroaryl optionally substituted with a substituent, n is an integral number of 0-4; said substituents are each independently selected from hydroxy, amino, carboxyl, cyano, nitro, halogen atom, $C_{1-6}$alkyl, $C_{1-6}$alkoxyl, $C_{1-6}$alkoxylC$_{1-6}$alkoxyl, $C_{1-6}$alkylamino, (C$_{1-6}$alkyl)$_2$amino, $C_{1-6}$alkylcarbonylamino, $C_{1-6}$alkylsulfonylamino, 3-8-membered cycloalkyl, aryl, 4-6-membered heterocyclyl, or 5-10-membered heteroaryl.

2. The compound according to claim 1, a pharmaceutically acceptable salt or a stereoisomer thereof, wherein, in the formula I, $L_1$ is a bond, —CR'R''—, —N—, —O—, or —S—;

$R_7$ is each independently selected from hydrogen, hydroxy, amino, carboxyl, cyano, nitro, halogen atom, $C_{1-6}$alkyl,

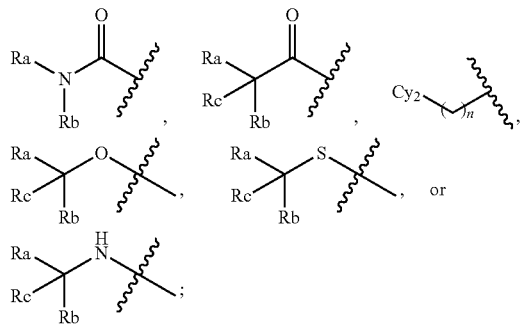

$R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 4-6-membered heterocyclyl optionally substituted with a substituent or 5-6-membered heteroaryl optionally substituted with a substituent, or, optionally $R_a$ and $R_b$ form a 4-6-membered ring with the atom to which they are attached; $C_{y2}$ is phenyl optionally substituted with a substituent, 4-6-membered heterocyclyl optionally substituted with a substituent, or 5-6-membered heteroaryl optionally substituted with a substituent, n is an integral number of 0-3; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, ($C_{1-6}$alkyl)$_2$amino, $C_{1-6}$alkylcarbonylamino, $C_{1-6}$alkylsulfonylamino, 3-8-membered cycloalkyl, phenyl, 4-6-membered heterocyclyl, or 5-6-membered heteroaryl.

3. The compound according to claim 1, a pharmaceutically acceptable salt or a stereoisomer thereof, wherein the compound has a structure represented by the following formula II:

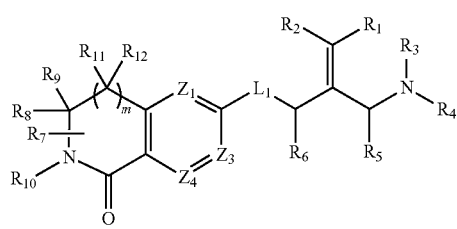

wherein, $R_1$ and $R_2$ are each independently selected from hydrogen, fluorine, chlorine, or bromine, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is —CR'R''—, —O— or —S—, R' and R'' are each independently selected from hydrogen or $C_{1-6}$ alkyl;

$Z_1$, $Z_3$ and $Z_4$ are each independently selected from CH or N;

$R_8$ and $R_9$ are each independently selected from hydrogen, hydroxy, amino, carboxyl, cyano, nitro, halogen atom or $C_{1-6}$alkyl, or, optionally $R_8$ and $R_9$ form a 3-6 membered cycloalkyl with the atom to which they are attached;

$R_{11}$ and $R_{12}$ are each hydrogen;

$R_{10}$ is selected from hydrogen, hydroxy, cyano, halogen atom, or $C_{1-6}$alkyl, m is 0 or 1; and $R_7$ is selected from hydrogen, hydroxy, amino, carboxyl, cyano, nitro, halogen atom or $C_{1-6}$alkyl.

4. The compound according to claim 1, a pharmaceutically acceptable salt or a stereoisomer thereof, wherein, in the formula i $R_8$, $R_9$, $R_{11}$ and $R_{12}$ are each independently selected from hydrogen, hydroxy, amino, carboxyl, cyano, nitro, halogen atom, $C_{1-6}$alkyl, $C_{1-6}$alkoxyl, $C_{1-6}$alkoxyl $C_{1-6}$alkoxyl, $C_{1-6}$alkylamino, ($C_{1-6}$alkyl)$_2$amino, $C_{1-6}$alkylcarbonylamino, $C_{1-6}$alkylsulfonylamino, haloC$_{1-6}$alkyl, haloC$_{1-6}$alkoxyl, $C_{1-6}$alkylsulfonyl, $C_{1-6}$alkylthio, 3-8-membered cycloalkyl, aryl, 4-6-membered heterocyclyl, or 5-10-membered heteroaryl, or, optionally at least one pair of $R_8$ and $R_9$, and $R_{11}$ and $R_{12}$ form a 3-6 membered cycloalkyl with the atom to which they are attached, or, optionally either $R_8$ or $R_9$, and, either $R_{11}$ or $R_{12}$ form a 3-6 membered ring with the atoms to which they are attached; or, optionally the atom(s) on $C_{y1}$ form a 4-7-membered ring together with the atoms in $R_6$ and $L_1$; or, optionally at least one pair of $R_8$ and $R_9$, and $R_{11}$ and $R_{12}$ form an oxo group;

$R_7$ is each independently selected from hydrogen, hydroxy, amino, carboxyl, cyano, nitro, halogen atom, $C_{1-6}$alkyl,

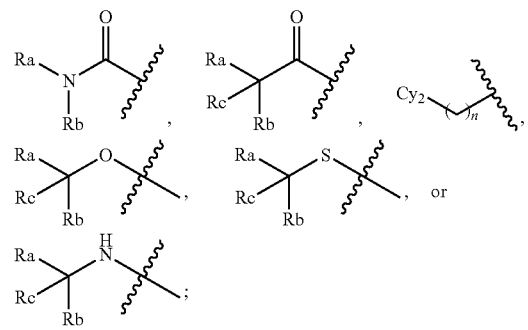

$R_a$, $R_b$ and $R_c$ are each independently selected from hydrogen, $C_{1-6}$alkyl optionally substituted with a substituent, $C_{2-6}$alkenyl optionally substituted with a substituent, $C_{2-6}$alkynyl optionally substituted with a substituent, 3-8-membered cycloalkyl optionally substituted with a substituent, aryl optionally substituted with a substituent, 4-6-membered heterocyclyl optionally substituted with a substituent or 5-6-membered heteroaryl optionally substituted with a substituent, or, optionally $R_a$ and $R_b$ form a 4-6-membered ring with the atom to which they are attached; $C_{y2}$ is phenyl optionally substituted with a substituent, 4-6-membered heterocyclyl optionally substituted with a substituent, or 5-6-membered heteroaryl optionally substituted with a substituent, n is an integral number of 0-3; said substituents are each independently selected from hydroxy, amino, carboxyl, cyano, nitro, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, 3-8-membered cycloalkyl, phenyl, 4-6-membered heterocyclyl, or 5-6-membered heteroaryl, in the formula i, when at least one of $Z_1$, $Z_2$, $Z_3$ and $Z_4$ is N, and they are not N at the same time, the ring formed by $Z_1$, $Z_2$, $Z_3$ and $Z_4$ is bonded to the $L_1$ group, in the formula i, when the ring formed by $Z_1$, $Z_2$, $Z_3$ and $Z_4$ is bonded to the $L_1$ group, and m is 0, $R_{10}$ is selected from hydroxy, cyano, halogen atom, $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-8-membered cycloalkyl, aryl, 4-6-membered heterocyclyl or 5-10-membered heteroaryl, in the formula i, when the ring formed by $Z_1$, $Z_2$, $Z_3$ and $Z_4$ is bonded to the $L_1$ group, and m is 1, $R_{10}$ is selected from hydroxy, cyano, halogen atom, branched $C_{1-6}$alkyl, $C_{1-6}$alkoxyl, $C_{1-6}$alkoxyl$C_{1-6}$alkoxyl, $C_{1-6}$alkylamino, $(C_{1-6}$alkyl$)_2$amino, $C_{1-6}$alkylcarbonylamino, $C_{1-6}$alkylsulfonylamino, halo$C_{1-6}$alkyl, halo$C_{1-6}$alkoxyl, $C_{1-6}$alkylsulfonyl, $C_{1-6}$alkylthio, 3-membered cycloalkyl or 4-membered cycloalkyl.

5. The compound according to claim 1, a pharmaceutically acceptable salt or a stereoisomer thereof, wherein the compound has a structure represented by the following formula II:

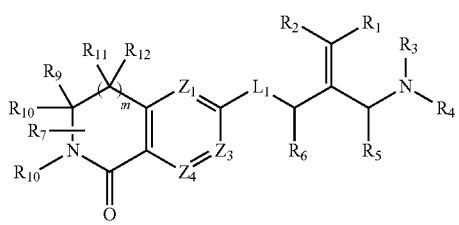

wherein, $R_1$ and $R_2$ are each independently selected from hydrogen, fluorine, chlorine, or bromine, and $R_1$ and $R_2$ are not hydrogen at the same time;

$R_3$ and $R_4$ are each independently selected from hydrogen or $C_{1-6}$ alkyl;

$R_5$ and $R_6$ are each independently selected from hydrogen or $C_{1-6}$ alkyl;

$L_1$ is a bond, —CR'R"—, —O— and —S—, R' and R" are each independently selected from hydrogen or $C_{1-6}$ alkyl;

$Z_1$, $Z_3$ and $Z_4$ are each independently selected from CH or N;

$R_8$, $R_9$, $R_{11}$ and $R_{12}$ are each independently selected from hydrogen, hydroxy, amino, carboxyl, cyano, nitro, halogen atom or $C_{1-6}$alkyl, or, optionally at least one pair of $R_8$ and $R_9$, and $R_{11}$ and $R_{12}$ form a 3-6 membered cycloalkyl with the atom to which they are attached; or, optionally either $R_8$ or $R_9$, and, either $R_{11}$ or $R_{12}$ form a 3-6 membered cycloalkyl with the atoms to which they are attached; or optionally $R_8$ and $R_9$ together form an oxo group;

$R_{10}$ is selected from hydrogen, hydroxy, cyano, halogen atom, $C_{1-6}$alkyl or 3-6-membered cycloalkyl, m is 0 or 1;

$R_7$ is selected from hydrogen, hydroxy, amino, carboxyl, cyano, nitro, halogen atom or $C_{1-6}$alkyl, and at least one of $Z_1$, $Z_3$ and $Z_4$ is N, and wherein, in the compound represented by formula II, in case that m in the left ring carrying a carbonyl is 0, $R_{10}$ is selected from hydroxy, cyano, halogen atom, $C_{1-6}$alkyl or 3-6-membered cycloalkyl, preferably $R_{10}$ is selected from branched $C_{1-6}$alkyl, 3-membered cycloalkyl or 4-membered cycloalkyl, or in the compound represented by formula II, in case that m in the left ring carrying a carbonyl is 1, $R_{10}$ is selected from hydroxy, cyano, halogen atom, branched $C_{1-6}$alkyl, 3-membered cycloalkyl or 4-membered cycloalkyl, preferably $R_{10}$ is selected from branched $C_{1-6}$alkyl, 3-membered cycloalkyl or 4-membered cycloalkyl.

6. The compound according to claim 5, a pharmaceutically acceptable salt or a stereoisomer thereof:

wherein, $R_1$ and $R_2$ are each independently selected from hydrogen, or fluorine, and $R_1$ and $R_2$ are not hydrogen at the same time;

$R_3$ and $R_4$ are each independently selected from hydrogen or $C_{1-6}$ alkyl;

$R_5$ and $R_6$ each are hydrogen;

$L_1$ is —CR'R"— or —O—, R' and R" are each independently selected from hydrogen or $C_{1-6}$ alkyl;

$Z_1$, $Z_3$ and $Z_4$ are each independently selected from CH or N;

$R_8$, $R_9$, $R_{11}$ and $R_{12}$ are each independently selected from hydrogen or $C_{1-6}$alkyl, or, optionally $R_8$ or $R_9$, with the atom to which they are attached, form cyclopropane, cyclobutane, cyclopentane; or optionally $R_8$ and $R_9$ together form an oxo group;

$R_{10}$ is selected from branched $C_{1-6}$alkyl, 3-membered cycloalkyl or 4-membered cycloalkyl;

m is 0 or 1; and $R_7$ is hydrogen.

7. The compound according to claim 4, a pharmaceutically acceptable salt or a stereoisomer thereof, wherein, in the formula i, when the ring formed by $Z_1$, $Z_2$, $Z_3$ and $Z_4$ is bonded to the $L_1$ group, and m is 0, $R_{10}$ is selected from hydroxy, cyano, halogen atom, branched $C_{1-6}$alkyl, 3-membered cycloalkyl or 4-membered cycloalkyl.

8. The compound according to claim 4, a pharmaceutically acceptable salt or a stereoisomer thereof, wherein in the formula i, when the ring formed by $Z_1$, $Z_2$, $Z_3$ and $Z_4$ is bonded to the $L_1$ group, and m is 1, $R_{10}$ is selected from hydroxy, cyano, halogen atom, branched $C_{1-6}$alkyl, 3-membered cycloalkyl or 4-membered cycloalkyl.

9. A compound, a pharmaceutically acceptable salt or a stereoisomer thereof, wherein said compound is selected from:

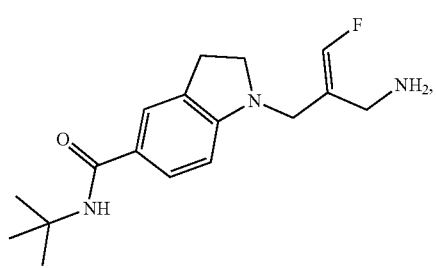

99
-continued
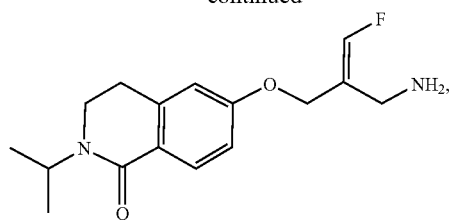
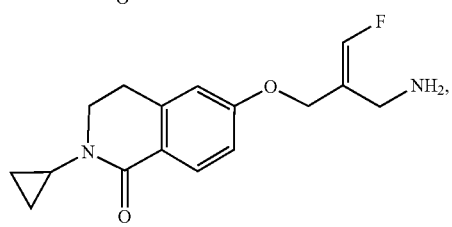
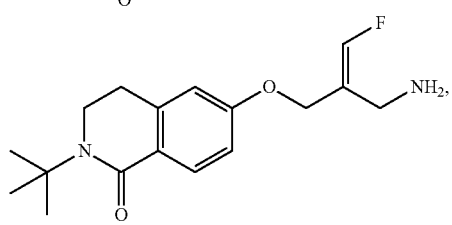
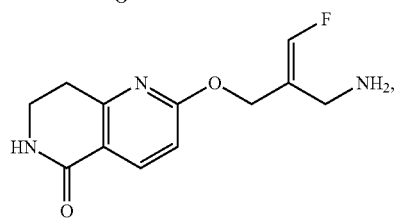
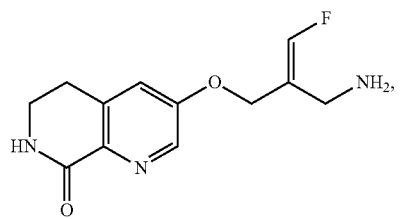
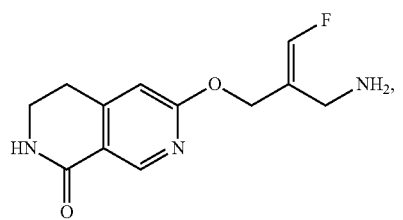
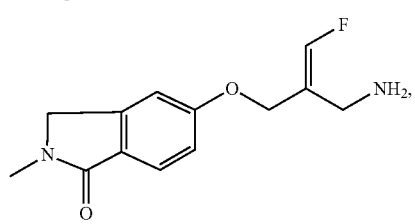
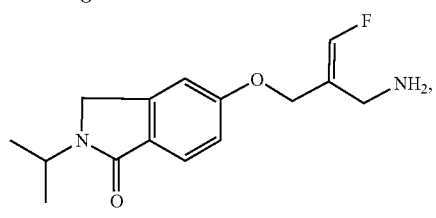
100
-continued
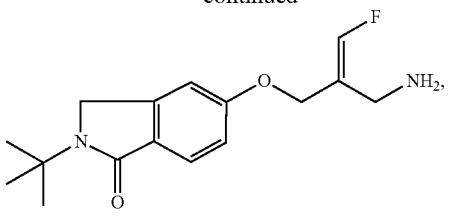
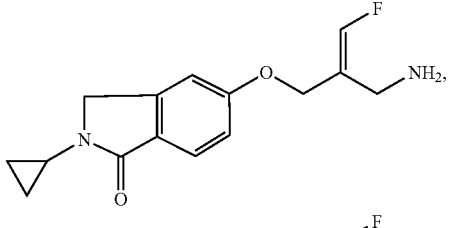
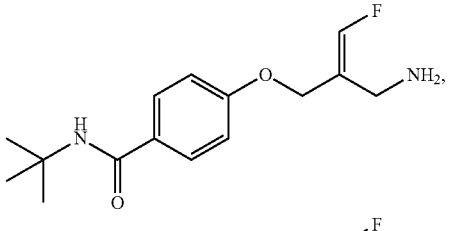
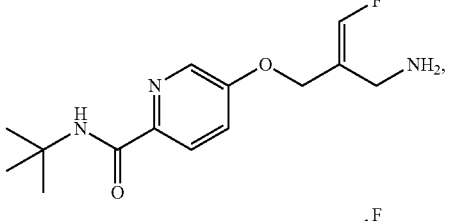
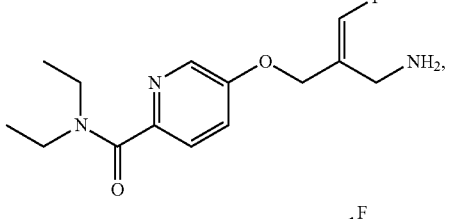
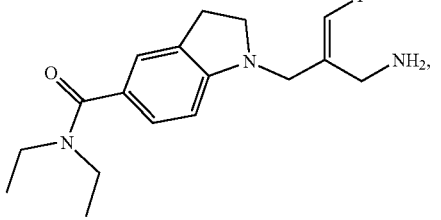
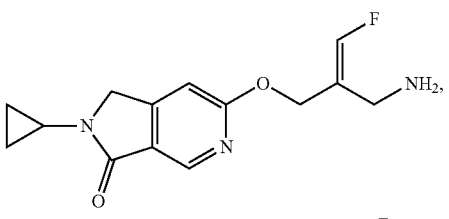
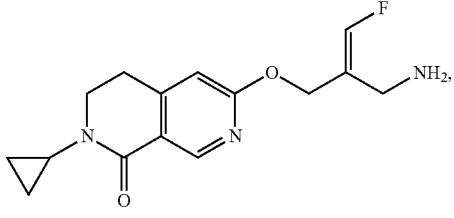

-continued

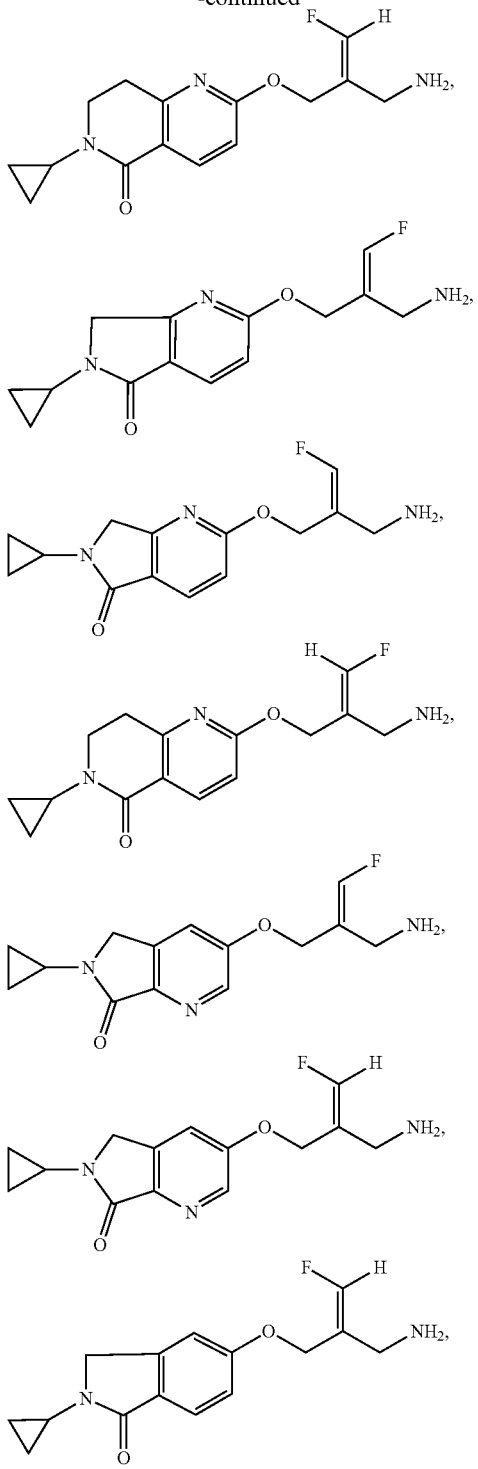

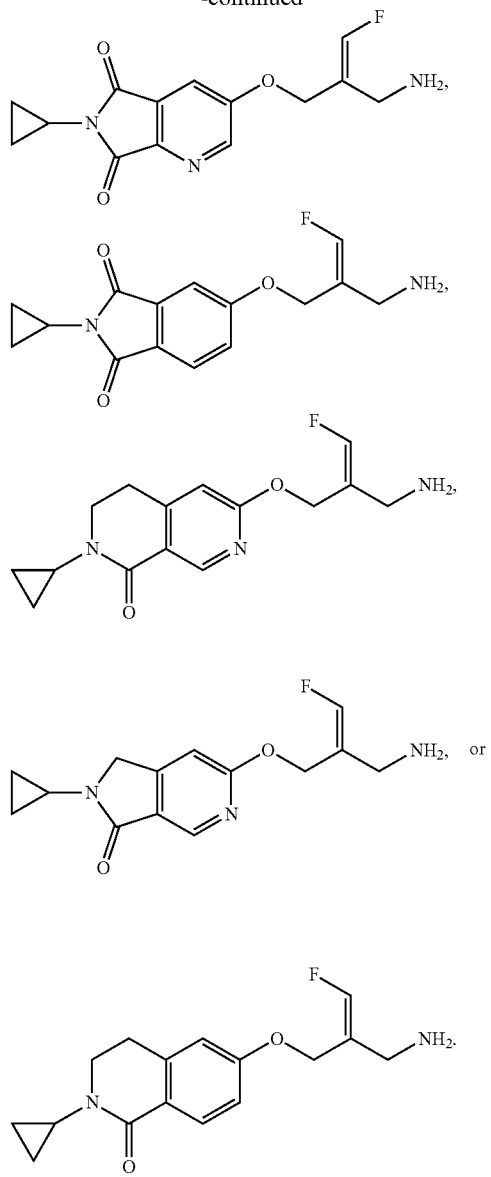

10. A pharmaceutical composition containing the compound according to claim 1, a pharmaceutically acceptable salt or a stereoisomer thereof, which optionally contains one or more pharmaceutically acceptable supports.

11. A pharmaceutical composition containing the compound according to claim 9 a pharmaceutically acceptable salt or a stereoisomer thereof, which optionally contains one or more pharmaceutically acceptable supports.

* * * * *